United States Patent
Hinks et al.

(10) Patent No.: US 12,157,713 B2
(45) Date of Patent: Dec. 3, 2024

(54) CONJUGATED OLIGOELECTROLYTES AS ANTIMICROBIAL AGENTS

(71) Applicants: Nanyang Technological University, Singapore (SG); National University of Singapore, Singapore (SG)

(72) Inventors: Jamie Hinks, Singapore (SG); Cheng Zhou, Singapore (SG); Guillermo C. Bazan, Singapore (SG)

(73) Assignees: Nanyang Technological University, Singapore (SG); National University of Singapore, Singapore (SG)

( * ) Notice: Subject to any disclaimer, the term of this patent is extended or adjusted under 35 U.S.C. 154(b) by 918 days.

(21) Appl. No.: 17/048,356

(22) PCT Filed: Apr. 25, 2019

(86) PCT No.: PCT/SG2019/050230
§ 371 (c)(1),
(2) Date: Oct. 16, 2020

(87) PCT Pub. No.: WO2019/209182
PCT Pub. Date: Oct. 31, 2019

(65) Prior Publication Data
US 2021/0147340 A1   May 20, 2021

Related U.S. Application Data

(60) Provisional application No. 62/662,422, filed on Apr. 25, 2018.

(51) Int. Cl.
| | | |
|---|---|---|
| C07C 217/64 | (2006.01) | |
| A01N 33/12 | (2006.01) | |
| A61K 8/41 | (2006.01) | |
| A61P 31/04 | (2006.01) | |
| A61Q 19/10 | (2006.01) | |

(52) U.S. Cl.
CPC ............ *C07C 217/64* (2013.01); *A01N 33/12* (2013.01); *A61K 8/416* (2013.01); *A61P 31/04* (2018.01); *A61Q 19/10* (2013.01)

(58) Field of Classification Search
CPC ....... C07C 217/64; A61P 31/04; A01N 33/12; A61K 8/416; A61Q 19/10
USPC ........................................................ 514/643
See application file for complete search history.

(56) References Cited

FOREIGN PATENT DOCUMENTS

| | | |
|---|---|---|
| CN | 104224775 A | 12/2014 |
| GB | 726260 A | 3/1955 |
| WO | 2005056499 A2 | 6/2005 |

OTHER PUBLICATIONS

O'Connell et al.; Combating Multidrug-Resistant Bacteria: Current Strategies for the Discovery of Novel Antibacterials; Angew. Chem. Int. Ed. 2013, 52, 10706-10733.
Lewis, K.; Platforms for antibiotic discovery; Nat. Rev. Drug Discov. 2013, 12, 371-387.
Chellat et al.; Targeting Antibiotic Resistance; Angew. Chem. Int. Ed. 2016, 55, 6600-6626.
Liu et al.; A Biosurfactant-Inspired Heptapeptide with Improved Specificity to Kill MRSA; Angew. Chem. 2017, 129, 1508-1512.
Fredersdorf et al.; Conformational Analysis of an Antibacterial Cyclodepsipeptide Active against *Mycobacterium tuberculosis* by a Combined ROE and RDC Analysis; Chem. Eur. J. 2017, 23, 5729-5735.
Wang et al.; Membrane activity of antimicrobial phenylene ethynylene based polymers and oligomers; Soft Matter 2012, 8, 8547-8558.
Takahashi et al.; Synthetic Random Copolymers as a Molecular Platform To Mimic Host-Defense Antimicrobial Peptides; Bioconjugate Chem. 2017, 28, 1340-1350.
Liu et al.; Highly potent antimicrobial polyionenes with rapid killing kinetics, skin biocompatibility and in vivo bactericidal activity; Biomaterials 2017, 127, 36-48.
Liu et al.; Nontoxic Membrane-Active Antimicrobial; Arylamide Oligomers; Angew. Chem. Int. Ed. 2004, 43, 1158-1162.

(Continued)

*Primary Examiner* — Kristin A Vajda
(74) *Attorney, Agent, or Firm* — Patterson + Sheridan, LLP

(57) ABSTRACT

Disclosed herein are compounds of formula I, where said compounds displays antibacterial properties. Also disclosed herein is the use of said compounds to treat microbial infection. The compounds of formula I have the following structure: where n, m, p, q, X, $R^1$ to $R^{11}$ are as defined herein.

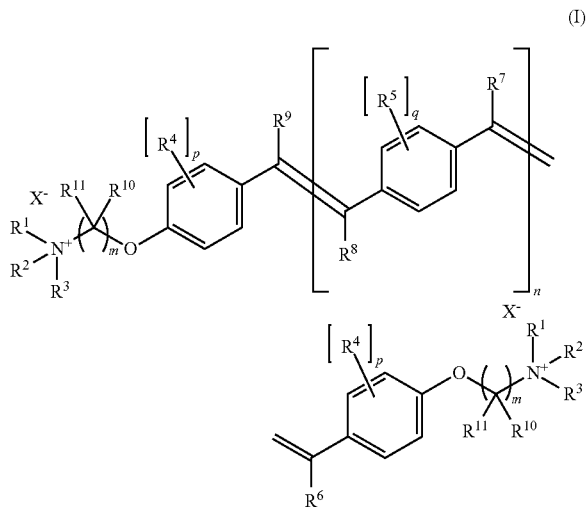

16 Claims, 9 Drawing Sheets

(56) References Cited

OTHER PUBLICATIONS

Stokes et al.; Pentamidine sensitizes Gram-negative pathogens to antibiotics and overcomes acquired colistin resistance; Nat. Microbiol. 2017, 2, 17028.
Colak et al.; Hydrophilic Modifications of an Amphiphilic Polynorbornene and the Effects on its Hemolytic and Antibacterial Activity; Biomacromolecules, 2009, 10, 353-359.
Suer et al.; Antimicrobial activities of phosphonium containing Polynorbornenes; RSC Adv. 2016, 6, 86151-86157.
Kuroda et al.; The Role of Hydrophobicity in the Antimicrobial and Hemolytic Activities of Polymethacrylate Derivatives; Chem. Eur. J. 2009, 15, 1123-1133.
Tejero et al.; High Efficiency Antimicrobial Thiazolium and Triazolium Side-Chain Polymethacrylates Obtained by Controlled Alkylation of the Corresponding Azole Derivatives; Biomacromolecules 2015, 16, 1844-1854.
Garner et al.; Modification of the Optoelectronic Properties of Membranes via Insertion of Amphiphilic Phenylenevinylene Oligoelectrolytes; J. Am. Chem. Soc. 2010, 132, 10042-10052.
Hinks et al.; Modeling Cell Membrane Perturbation by Molecules Designed for Transmembrane Electron Transfer; Langmuir 2014, 30, 2429-2440.
Hinks et al.; Oligopolyphenylenevinylene-Conjugated Oligoelectrolyte Membrane Insertion Molecules Selectively Disrupt Cell Envelopes of Gram-Positive Bacteria; Appl. Environ. Microbiol. 2015, 81, 1949-1958.
Ortony et al.; Self-Assembly of an Optically Active Conjugated Oligoelectrolyte; J. Am. Chem. Soc. 2011, 133, 8380-8387.
Kato et al.; A Luminescent Oligo (p-phenylenevinylene) Wrapped with Amylose; Chemistry Letters, 2009, 38, 1192-1193.
Diehnelt, C. W.; Peptide array based discovery of synthetic antimicrobial peptides; Front. Microbiol. 2013, 4, 402.
Baskin et al.; Oligopolyphenylenevinylene-Conjugated Oligoelectrolyte Membrane Insertion Molecules Selectively Disrupt Cell Envelopes of Gram-Positive Bacteria; Bioorg. Med. Chem. Lett. 2012, 22, 1402-1407.
Campos et al.; Capsule Polysaccharide Mediates Bacterial Resistance to Antimicrobial Peptides; Infect. Immun. 2004, 72, 7107-7114.
Whitfield et al.; Structure, assembly and regulation of expression of capsules in *Escherichia coli*; Mol. Microbiol. 1999, 31, 1307-1319.
Anderson et al.; Polysaccharide Capsule and Sialic Acid-Mediated Regulation Promote; Biofilm-Like Intracellular Bacterial Communities during Cystitis; Infect. Immun. 2010, 78, 963-975.
Falagas et al.; Colistin: The Revival of Polymyxins for the Management of Multidrug-Resistant Gram-Negative Bacterial Infections; Clin. Infect. Dis. 2005, 40, 1333-1341.
Tran et al.; Daptomycin-Resistant Enterococcus faecalis Diverts the Antibiotic Molecule from the Division Septum and Remodels Cell Membrane Phospholipids; mBio 2013, 4, e00281-00213.
Keogh et al.; Enterococcal Metabolite Cues Facilitate Interspecies Niche Modulation and Polymicrobial Infection; Cell Host Microbe, 2016, 20, 493-503.
Navas et al.; Composition dependence of vesicle morphology and mixing properties in a bacterial model membrane system; BBA. Biomembranes 2005, 1716, 40-48.
Gabriel et al.; Infectious Disease: Connecting Innate Immunity to Biocidal Polymers; Mater. Sci. Eng. R Rep. 2007, 57, 28-64.
Strandberg et al.; Hydrophobic mismatch of mobile transmembrane helices: Merging theory and experiments; BBA. Biomembranes 2012, 1818, 1242-1249.
Scherber et al.; Membrane phase behavior of *Escherichia coli* during desiccation, rehydration, and growth recovery; BBA. Biomembranes 2009, 1788, 2427-2435.
Yan et al.; Influence of molecular structure on the antimicrobial function of phenylenevinylene conjugated oligoelectrolytes; Chem. Sci. 2016, 7, 5714-5722.
The China National Intellectual Property Administration CN First Office Action and Search Report for related Application No. 2019800412604_dated Nov. 30, 2022.
Chapman, C. W. et al., The In Vitro Antibacterial Action of Dialkylamino-alkyl Ethers of Stilbestrol and Hexylresocinol. Journal of the American Pharmaceutical Association. Mar. 1, 1947, vol. 36, No. 3, pp. 78-82; [Retrieved on Jun. 18, 2019] <DOI: 10.1002/JPS.3030360306> see p. 78 last paragraph.
International Search Report and Written Opinion in related application PCT/SG2019/050230 dated Jul. 11, 2019.
Yan et al.; Influence of Molecular Structure on the Antimicrobial Function of Phenylenevinylene conjugared Oligoelectrolytes; Chem. Sci., 2016, 7, 5714.
Zhou et al.; Informed Molecular Design of Conjugated Oligoelectrolytes To Increase Cell Affinity and Antimicrobial Activity; Angew. Chem. Int. Ed. 2018, 57, 8069 -8072.

CONJUGATED OLIGOELECTROLYTES AS ANTIMICROBIAL AGENTS

FIELD OF INVENTION

This invention relates to conjugated oligoelectrolytes and their use as antimicrobial agents towards a wide spectrum of infective agents, including bacteria, fungi and viruses, as well as compositions containing said compounds.

BACKGROUND

The listing or discussion of a prior-published document in this specification should not necessarily be taken as an acknowledgement that the document is part of the state of the art or is common general knowledge.

The emergence and spread of difficult-to-treat multidrug resistant pathogens is a matter of great concern to the world's healthcare systems, research communities, clinicians, government agencies and general population at large. This global threat is currently addressed by a thin pipeline of emerging drugs and has therefore prompted an urgent need for new class of antimicrobial agents. In view of this, the World Health Organization (WHO) maintains a list of bacteria for which new antibiotics or antibacterial agents are urgently needed.

The list was drawn up in a bid to guide and promote research and development of new antibiotics as part of the WHO's efforts to address growing global resistance to antimicrobial medicines.

A class of antibacterial drugs is antimicrobial peptides (AMPs) which are regarded as promising candidates for treating multidrug-resistant bacteria. However, only a few AMPs have been approved clinically, and this is largely due to their high preparation costs, and their non-ideal chemical, proteolytic and physical stability. In addition, the structural complexity of AMPs makes them challenging to turn into medicines.

On the other hand, synthetic membrane-inserting AMP mimics have been developed that capture some of the essential functions of AMPs, while overcoming certain limitations. Examples of these include arylamide oligomers, polynorbornenes, polymethacrylates and an emerging class of compounds referred to as conjugated oligoelectrolytes (COEs). Typically, COEs contain a hydrophobic conjugated backbone structure and terminal polar pendant-groups and have the potential to inhibit microbial growth, presumably by inserting into and disrupting microbial membranes.

Given the above, there remains a need for new antimicrobial agents that demonstrate high antimicrobial activity towards a broad spectrum of microorganisms, and at the same time exhibit low toxicity towards mammalian cells and are easy and cheap to produce in large quantity. Such antimicrobial agents can potentially be used as pharmaceutical products for bacterial infections, or can be advantageously incorporated into cleaning or cosmetic agents (such as soaps, detergents and shampoo) for personal care and/or hygiene products and bioicides.

SUMMARY OF INVENTION

Aspects and embodiments of the current invention are provided in the following numbered clauses.

1. A compound of formula I:

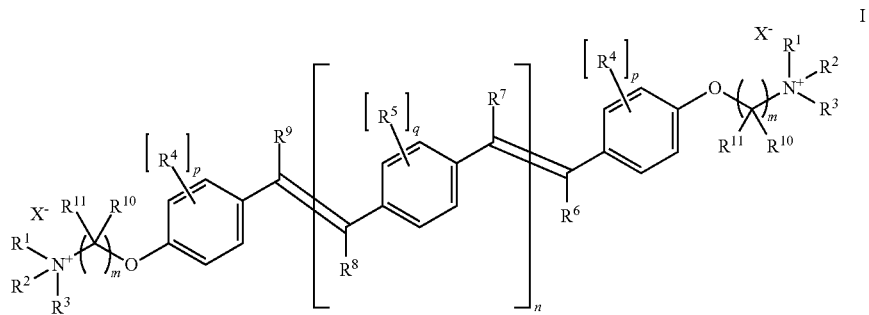

wherein:
n is 0 to 4;
m, at each occurrence, independently represents is 1 to 12;
p and q, at each occurrence, independently represents 0 to 4;
$R^1$, at each occurrence, independently represents a $C_{1-12}$ alkyl group, a $-(CH_2)_o-NR^{1'}R^{2'}$ group or a $-(CH_2)_{o'}-N^+R^{1'}R^{2'}R^{3'}$ group, the latter group's charge being balanced by an $X^-$;
each $R^{1'}$, $R^2$, $R^3$, $R^{2'}$ and $R^{3'}$ are independently a $C_{1-12}$ alkyl group;
and o' are 1 to 12;
$R^4$ to $R^9$, at each occurrence, independently represents:
(a) H;
(b) halo;
(c) CN;
(d) $C_{1-6}$ alkyl, $C_{2-6}$ alkenyl, $C_{2-6}$ alkynyl (which latter three groups are unsubstituted or substituted by one or more substituents selected from F, Cl, Br (e.g. Cl, F, such as F), nitro, CN, $C_{1-6}$ alkyl, $C_{2-6}$ alkenyl, $C_{2-6}$ alkynyl (which latter three groups are unsubstituted or substituted by one or more substituents selected from OH, =O, F, C, Br (e.g. Cl, F, such as F), $C_{1-4}$ alkyl and $C_{1-4}$ alkoxy), $Cy^1$ (which $Cy^1$ group is unsubstituted or is substituted by one or more substituents selected from F, Cl, Br (e.g. Cl, F, such as F), nitro, CN, $C_{1-6}$ alkyl, $C_{2-6}$ alkenyl, $C_{2-6}$ alkynyl (which latter three groups are optionally substituted by one or more substituents selected from OH, =O, F, Cl, Br (e.g. Cl, F, such as F), $C_{1-4}$ alkyl and $C_{1-4}$ alkoxy), $OR^{12a}$, $S(O)_rR^{12b}$, $S(O)_2NR^{12c}R^{12d}$, $NR^{12e}S(O)_2R^{12f}$, $NR^{12g}R^{12h}$, aryl and Het$^1$);
(e) $Cy^2$ (which $Cy^2$ group is unsubstituted or is substituted by one or more substituents selected from F, Cl, Br (e.g. Cl, F, such as F), nitro, CN, $C_{1-6}$ alkyl, $C_{2-6}$ alkenyl, $C_{2-6}$ alkynyl (which latter three groups are optionally substituted by one or more substituents selected from OH, =O, F, C, Br (e.g. Cl, F, such as F), $C_{1-4}$ alkyl and $C_{1-4}$ alkoxy), $OR^{13a}$, $S(O)_rR^{13b}$, $S(O)_2NR^{13c}R^{13d}$, $NR^{13e}S(O)_2R^{13f}$, $NR^{13g}R^{13h}$, aryl and $Het^2$), (f) $Het^a$ (which $Het^a$ group is unsubstituted or substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, F, C, Br (e.g. Cl, F, such as F), $C_{1-4}$ alkyl and $C_{1-4}$ alkoxy), $OR^{14a}$, $S(O)_rR^{14b}$, $S(O)_2NR^{14c}R^{14d}$, $NR^{14e}S(O)_2R^{14f}$, $NR^{14g}R^{14h}$, aryl and $Het^3$);

(g) $OR^{15a}$;

(h) $S(O)_rR^{15b}$;

(i) $S(O)_2NR^{15c}R^{15d}$;

(j) $NR^{15e}S(O)_2R^{15f}$; and (k) $NR^{15g}R^{15h}$;

$R^{10}$ and $R^{11}$, at each occurrence, independently represents:

(i) H;

(ii) F, Cl or Br;

(iii) CN;

(iv) $C_{1-6}$ alkyl, $C_{2-6}$ alkenyl, $C_{2-6}$ alkynyl (which latter three groups are unsubstituted or substituted by one or more substituents selected from F, Cl, Br (e.g. Cl, F, such as F), nitro, CN, $C_{1-6}$ alkyl, $C_{2-6}$ alkenyl, $C_{2-6}$ alkynyl (which latter three groups are unsubstituted or substituted by one or more substituents selected from OH, =O, F, C, Br (e.g. Cl, F, such as F), $C_{1-4}$ alkyl and $C_{1-4}$ alkoxy), $Cy^{1'}$ (which $Cy^{1'}$ group is unsubstituted or is substituted by one or more substituents selected from F, Cl, Br (e.g. Cl, F, such as F), nitro, CN, $C_{1-6}$ alkyl, $C_{2-6}$ alkenyl, $C_{2-6}$ alkynyl (which latter three groups are optionally substituted by one or more substituents selected from OH, =O, F, C, Br (e.g. Cl, F, such as F), $C_{1-4}$ alkyl and $C_{1-4}$ alkoxy), $OR^{12a'}$, $S(O)_rR^{12b'}$, $S(O)_2NR^{12c'}R^{12d'}$, $NR^{12e'}S(O)_2R^{12f'}$, $NR^{12'}R^{12h'}$, aryl and $Het^{1'}$);

(v) $Cy^{2'}$ (which $Cy^{2'}$ group is unsubstituted or is substituted by one or more substituents selected from F, Cl, Br (e.g. Cl, F, such as F), nitro, CN, $C_{1-6}$ alkyl, $C_{2-6}$ alkenyl, $C_{2-6}$ alkynyl (which latter three groups are optionally substituted by one or more substituents selected from OH, =O, F, C, Br (e.g. Cl, F, such as F), $C_{1-4}$ alkyl and $C_{1-4}$ alkoxy), $OR^{13a'}$, $S(O)R^{13b'}$, $S(O)_2NR^{13c'}R^{13d'}$, $NR^{13e'}S(O)_2R^{13f'}$, $NR^{13'}R^{13h'}$, aryl and $Het^{2'}$), (vi) $Het^{a'}$ (which $Het^{a'}$ group is unsubstituted or substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, F, C, Br (e.g. Cl, F, such as F), $C_{1-4}$ alkyl and $C_{1-4}$ alkoxy), $OR^{a'}$, $S(O)R^{14b'}$, $S(O)_2NR^{14c'}R^{14d'}$, $NR^{14e'}S(O)_2R^{14f'}$, $NR^{4g'}R^{14h'}$, aryl and $Het^{3'}$);

(vii) $OR^{15a'}$;

(viii) $S(O)_rR^{15b'}$;

(ix) $S(O)_2NR^{15c'}R^{15d'}$;

(x) $NR^{15e'}S(O)_2R^{15f'}$;

(xi) $NR^{15g'}R^{15h'}$;

$R^{12a}$ to $R^{12h}$, $R^{13a}$ to $R^{13h}$, $R^{14a}$ to $R^{14h}$, $R^{15a}$ to $R^{15h}$, $R^{12a'}$ to $R^{12h'}$, $R^{13'}$ to $R^{13h'}$, $R^{14a'}$ to $R^{14'}$, $R^{15a'}$ to $R^{15'}$, independently represent, at each occurrence, H, $C_{1-6}$ alkyl, $C_{2-6}$ alkenyl, $C_{2-6}$ alkynyl (which latter three groups are optionally substituted by one or more substituents selected from F, Cl, Br (e.g. Cl, F, such as F), nitro, =O, $C(O)OC_{1-4}$ alkyl, CN, $C_{1-6}$ alkyl, $C_{2-6}$ alkenyl, $C_{2-6}$ alkynyl, $C_{3-6}$ cycloalkyl (which latter three groups are optionally substituted by one or more substituents selected from OH, =O, F, C, Br (e.g. Cl, F, such as F), $C_{1-4}$ alkyl and $C_{1-4}$ alkoxy), $OR^{16}$, $S(O)R^{16b}$, $S(O)_2NR^{16c}R^{16d}$, $NR^{16e}S(O)_2R^{16f}$, $NR^{16g}R^{16h}$, aryl and $Het^4$), $C_{3-10}$ cycloalkyl, or $C_{4-10}$ cycloalkenyl (which latter two groups are optionally substituted by one or more substituents selected from F, C, Br (e.g. Cl, F, such as F), OH, =O, $C_{1-6}$ alkyl and $C_{1-6}$ alkoxy) or $Het^b$;

$R^{16a}$ to $R^{16h}$ independently represent at each occurrence, H, $C_{1-4}$ alkyl, $C_{2-4}$ alkenyl, $C_{2-4}$ alkynyl which latter three groups are optionally substituted by one or more substituents selected from F, Cl, Br (e.g. Cl, F, such as F), nitro, CN, $C_{1-4}$ alkyl, $C_{2-4}$ alkenyl, $C_{2-4}$ alkynyl (which latter three groups are optionally substituted by one or more substituents selected from OH, =O, F, C, Br (e.g. Cl, F, such as F), $C_{1-4}$ alkyl and $C_{1-4}$ alkoxy), $C_{3-6}$ cycloalkyl, or $C_{1-6}$ cycloalkenyl (which latter two groups are optionally substituted by one or more substituents selected from F, Cl, Br (e.g. Cl, F, such as F), OH, =O, $C_{1-4}$ alkyl and $C_{1-4}$ alkoxy), $Het^1$ to $Het^4$, $Het^{1'}$ to $Het^{3'}$, $Het^a$, $Het^b$ and $Het^{a'}$ independently represent a 4- to 14-membered heterocyclic groups containing one or more heteroatoms selected from O, S and N, which heterocyclic groups may comprise one, two or three rings and may be substituted by one or more substituents selected from =O, or more particularly, halo, $C_{1-6}$ alkyl, which latter group is optionally substituted by one or more substituents selected from F, C, Br (e.g. Cl, F, such as F), $-OR^{7a}$, $-NR^{17b}R^{7c}$, $-C(O)OR^{17d}$ and $-C(O)NR^{17e}R^{17f}$;

$R^{17a}$ to $R^{17f}$ independently represent at each occurrence, H, $C_{1-4}$ alkyl, $C_{2-4}$ alkenyl, $C_{2-4}$ alkynyl which latter three groups are optionally substituted by one or more substituents selected from F, Cl, Br (e.g. Cl, F, such as F), nitro, CN, $C_{1-4}$ alkyl, $C_{2-4}$ alkenyl, $C_{2-4}$ alkynyl (which latter three groups are optionally substituted by one or more substituents selected from OH, =O, F, C, Br (e.g. Cl, F, such as F), $C_{1-4}$ alkyl and $C_{1-4}$ alkoxy), $C_{1-6}$ cycloalkyl, or $C_{4-6}$ cycloalkenyl (which latter two groups are optionally substituted by one or more substituents selected from F, Cl, Br (e.g. Cl, F, such as F), OH, =O, $C_{1-4}$ alkyl and $C_{1-4}$ alkoxy), $Cy^1$, $Cy^2$, $Cy^{1'}$ and $Cy^{2'}$, at each occurrence, independently represents a 3- to 10-membered aromatic, fully saturated or partially unsaturated carbocyclic ring;

each r independently represents 0, 1 or 2; and each $X^-$ is a pharmaceutically acceptable anion, or pharmaceutically acceptable salts and solvates thereof.

2. The compound according to Clause 1, wherein p and q are 0 and each of $R^6$ to $R^{11}$ is H.

3. The compound according to Clause 1 or Clause 2, wherein:

n is 0 or 1; and/or m is 4 to 8.

4. The compound according to any one of the preceding clauses, wherein o, when present, is 2 to 4, such as 2.

5. The compound according to any one of the preceding clauses, wherein o', when present, is 2 to 4, such as 2.

6. The compound according to any one of the preceding clauses, wherein each of $R^1$ to $R^3$ is methyl.

7. The compound according to any one of Clauses 1 to 5, wherein $R^1$ is a $-(CH_2)_o-NR^{1'}R^{2'}$ or a $-(CH_2)_o-N^+R^{1'}R^{2'}R^{3'}$ group, optionally wherein $R^2$ and $R^3$ are methyl.

8. The compound according to any one of Clauses 1 to 5 and 7, wherein $R^1$ is a a $-(CH_2)_o-N^+R^{1'}R^{2'}R^{3'}$ group.

9. The compound according to any one of Clauses 1 to 5 and 7 to 8, wherein when $R^1$ is a $-(CH_2)_o-NR^{1'}R^{2'}$ group or a $-(CH_2)_o-N^+R^{1'}R^{2'}R^{3'}$ group, each $R^{1'}$, $R^{2'}$ and $R^{3'}$ is a $C_1$ to $C_4$ alkyl, such as a methyl group.

10. The compound according to any one of Clauses 1 to 5 and 7 to 9, wherein:
n is 0 or 1;
m is 4, 6 or 8;
each $R^1$ is a —$(CH_2)_o$—$NR^{1'}R^{2'}$ group or a —$(CH_2)_o$—$N^+R^{1'}R^{2'}R^{3'}$ group, the latter group's charge being balanced by an $X^-$;
each $R^{1'}$, $R^2$, $R^3$, $R^{2'}$ and $R^{3'}$ are independently a $C_{1-4}$ alkyl group; and
o and o' are 2 to 3.

11. The compound according to any one of the preceding clauses, wherein the compound of formula I is selected from the group consisting of:

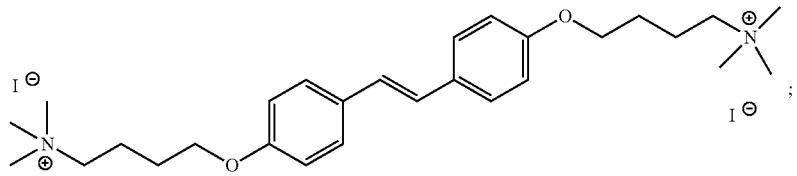

COE-D4

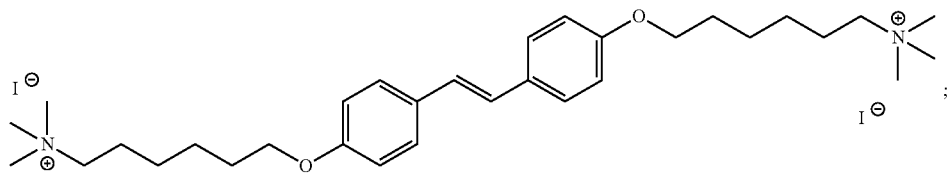

COE-D6

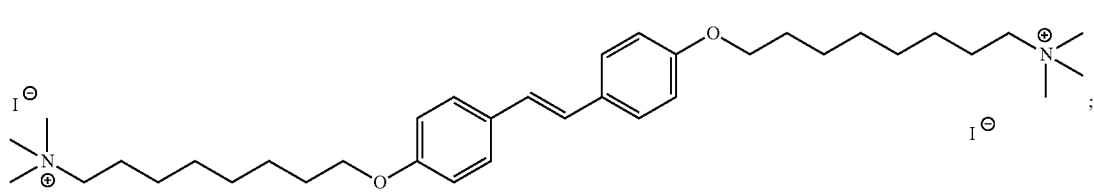

COE-D8

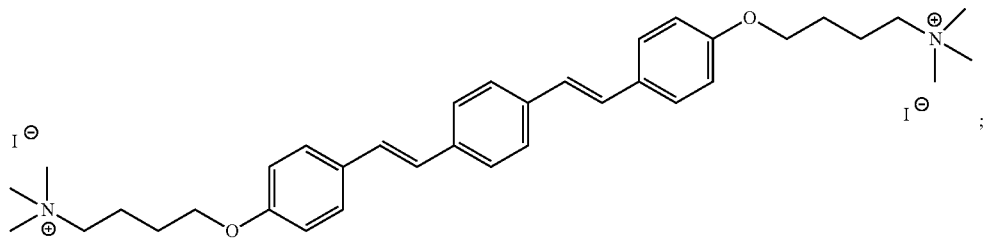

COE-T4

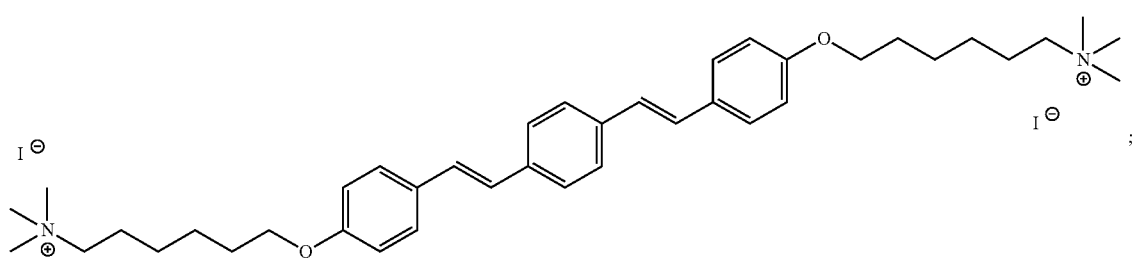

COE-T6

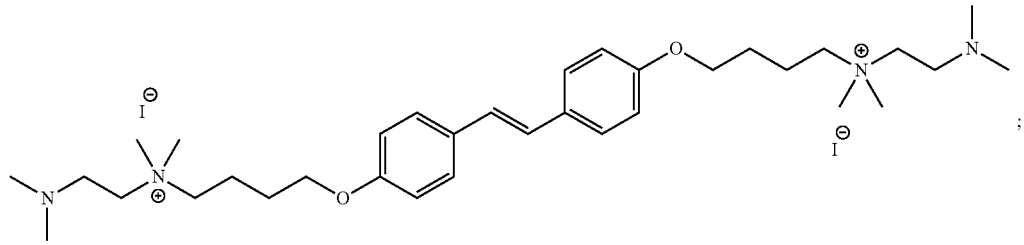

COE-D42N

-continued
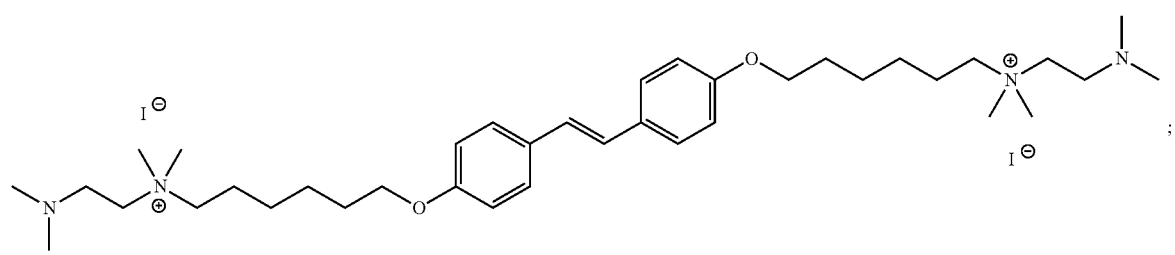
COE-D62N
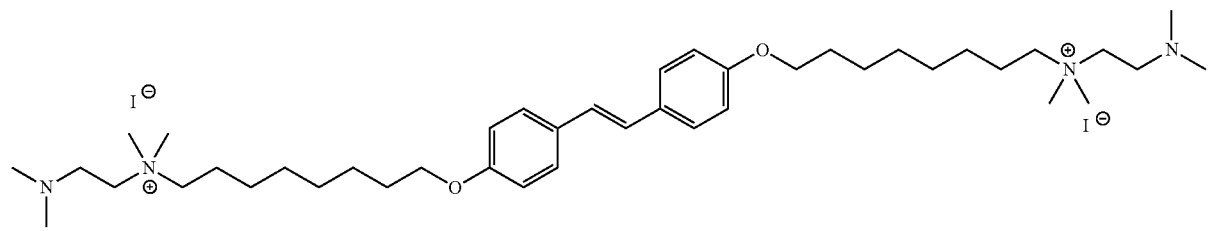
COE-D82N
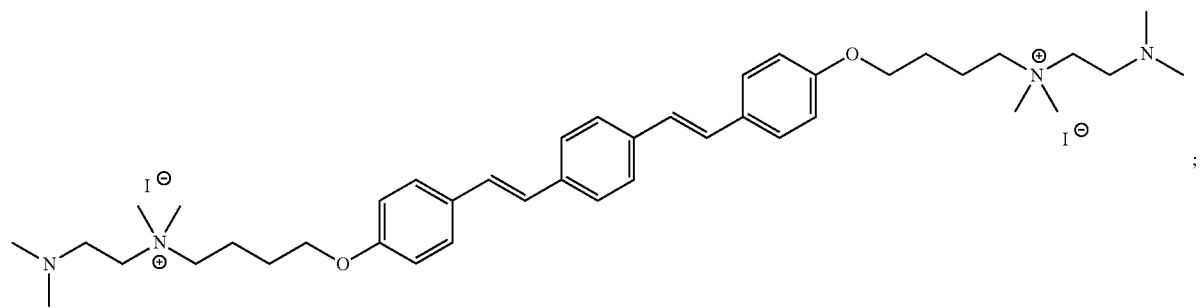
COE-T42N
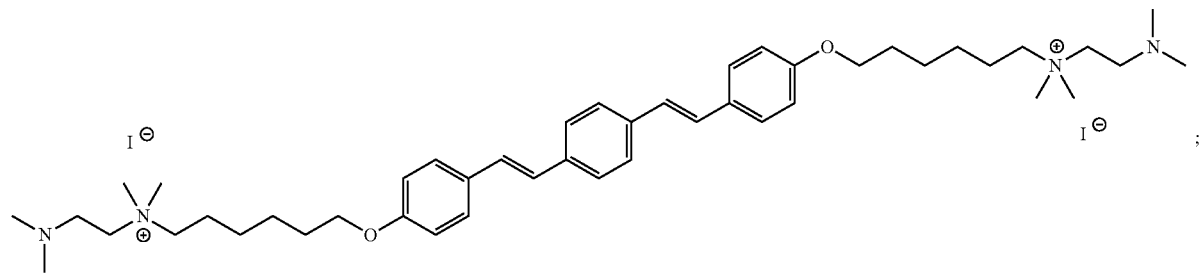
COE-T62N
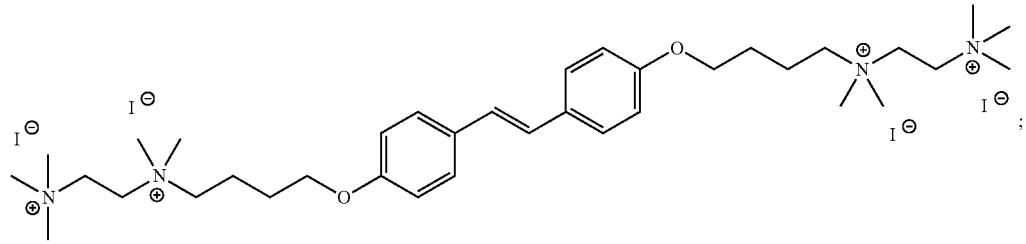
COE-D42

-continued
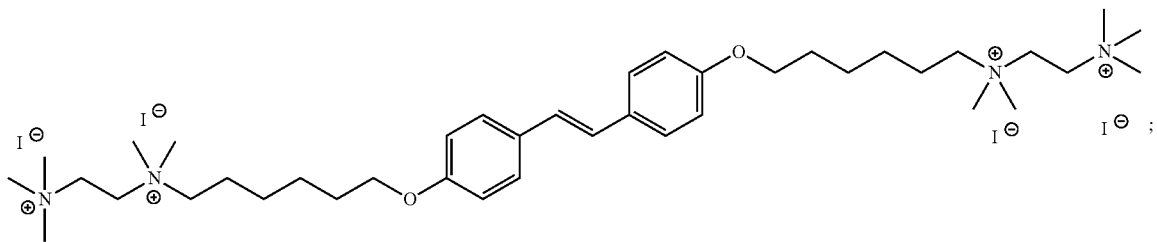
COE-D62
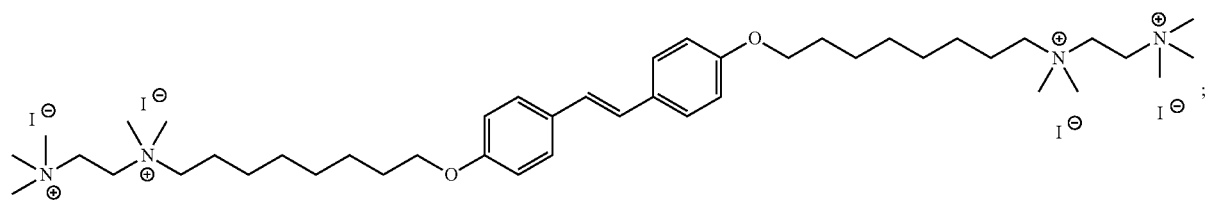
COE-D82
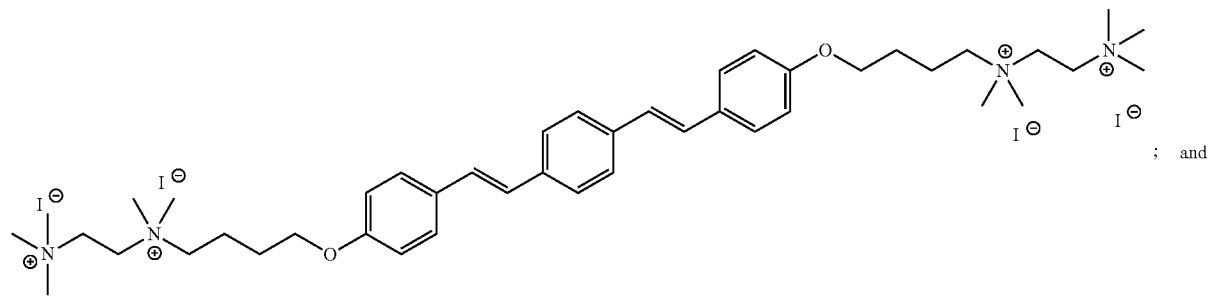
COE-T42
; and
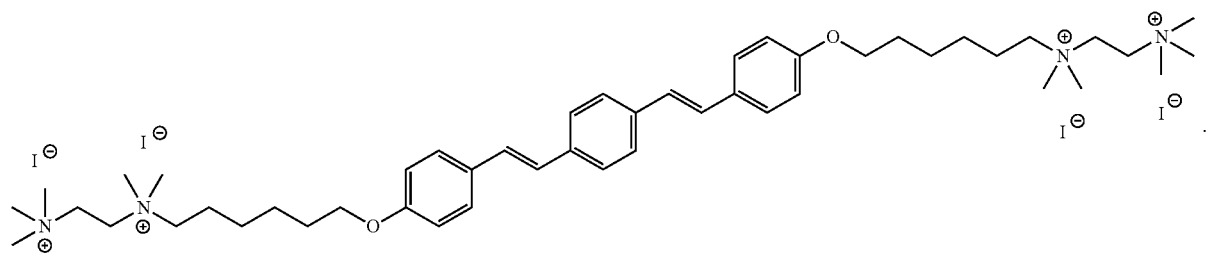
COE-T62
12. The compound according to Clause 11, wherein the compound of formula I is selected from the group consisting of:
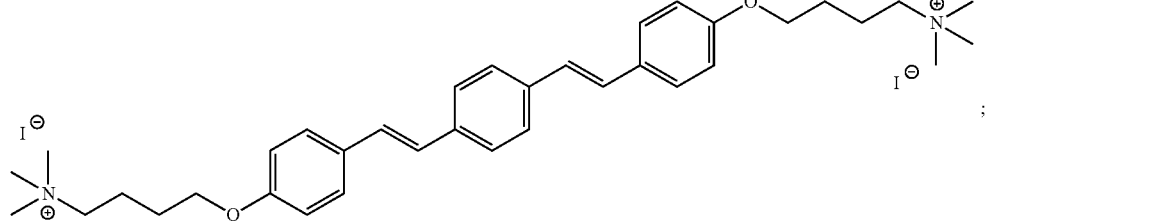
COE-T4
;

-continued
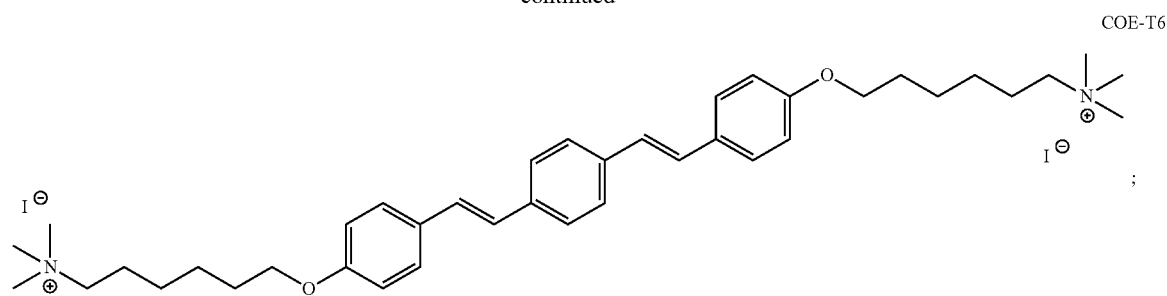
COE-T6
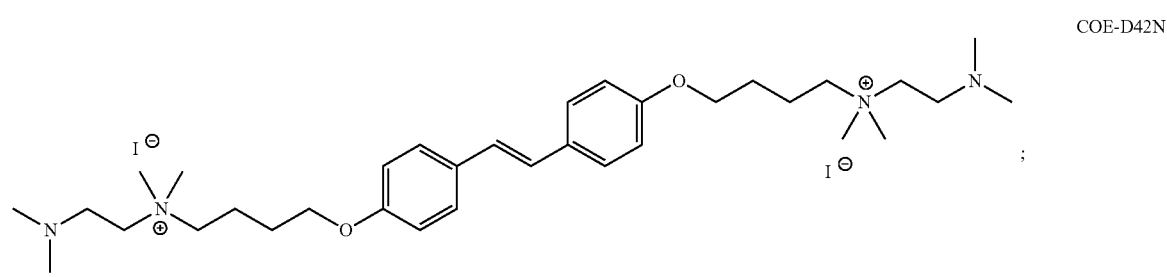
COE-D42N
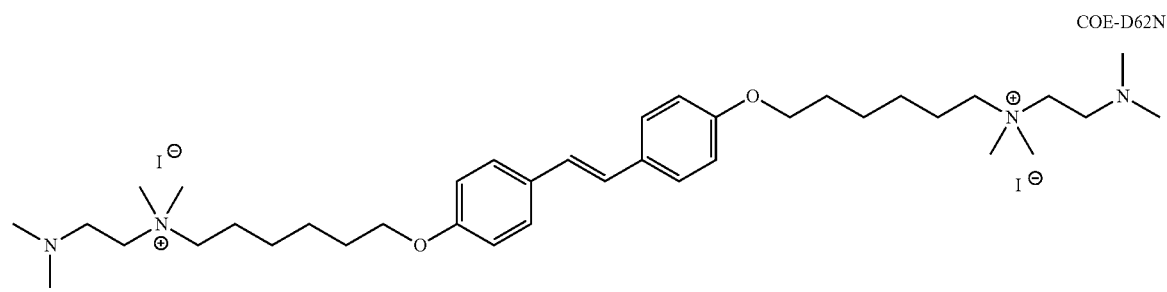
COE-D62N
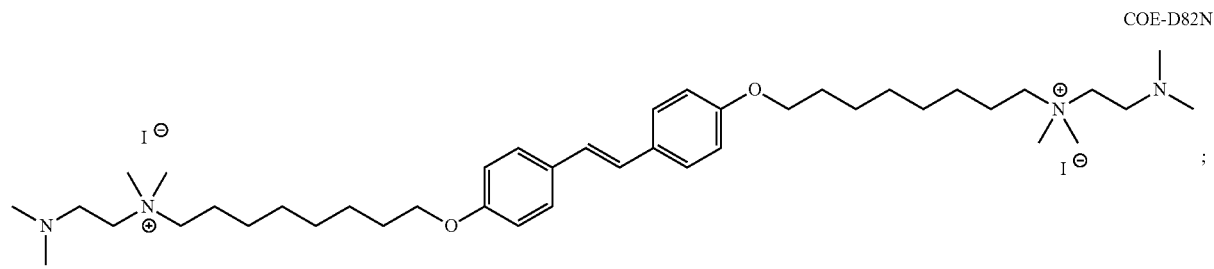
COE-D82N
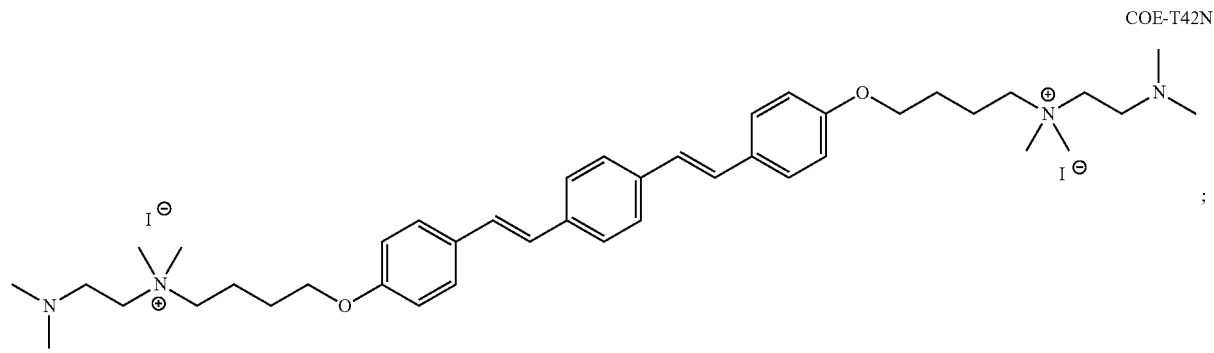
COE-T42N -continued
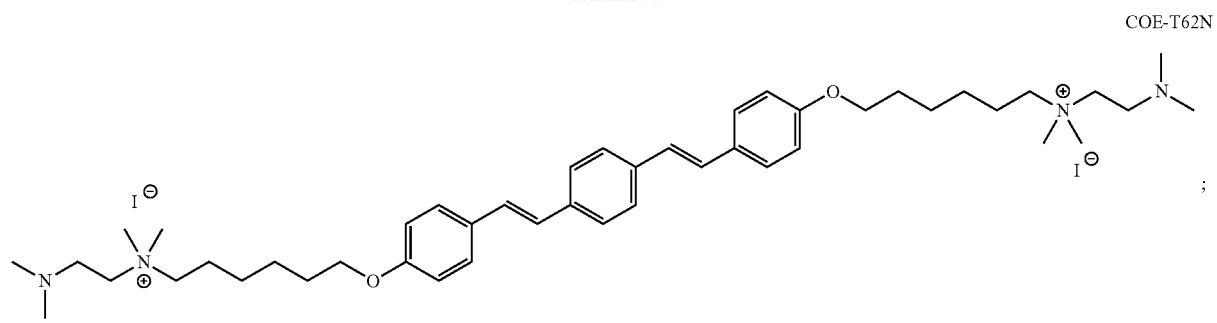
COE-T62N
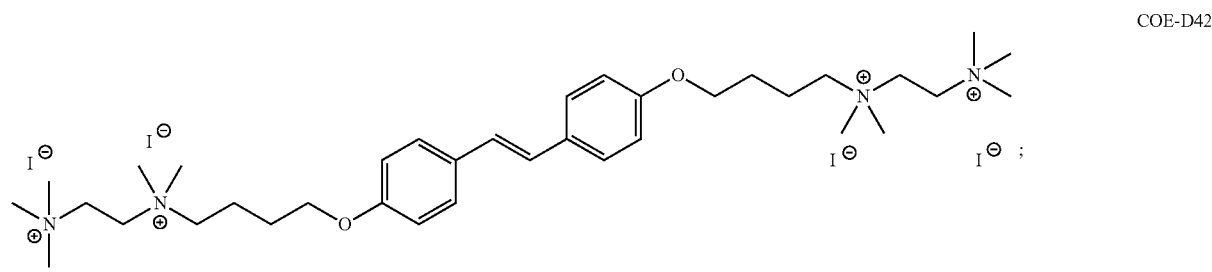
COE-D42
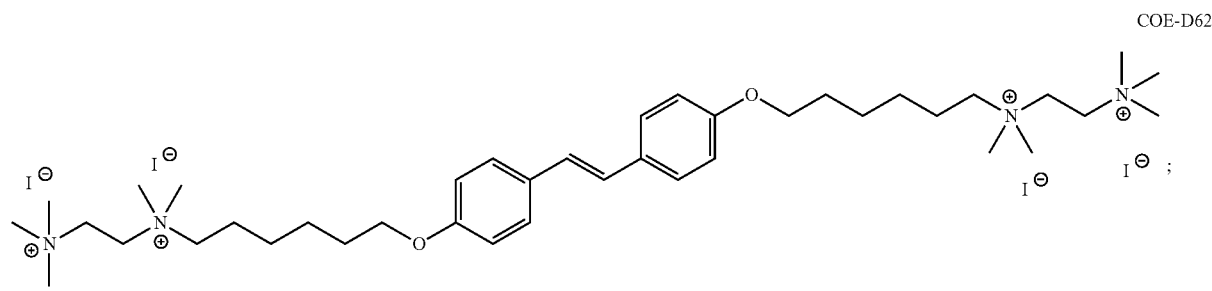
COE-D62
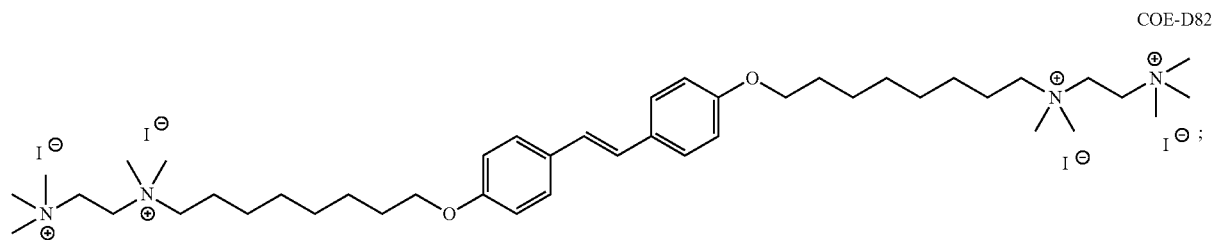
COE-D82
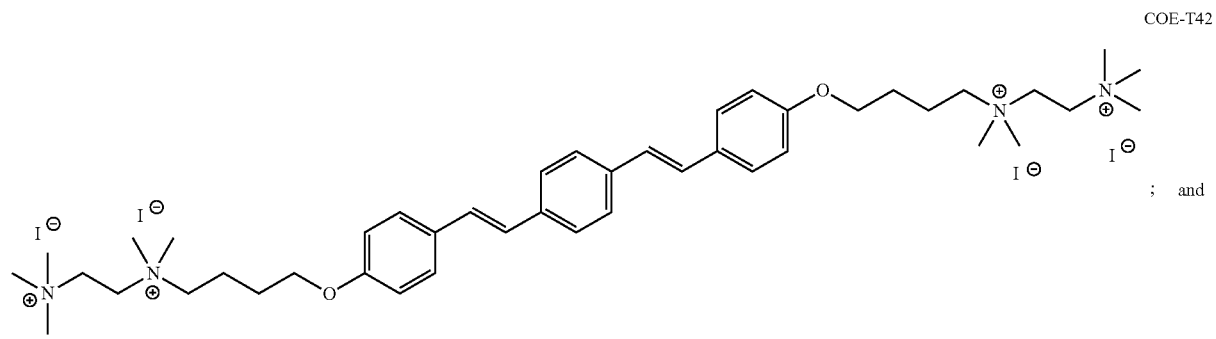
COE-T42
; and COE-T62
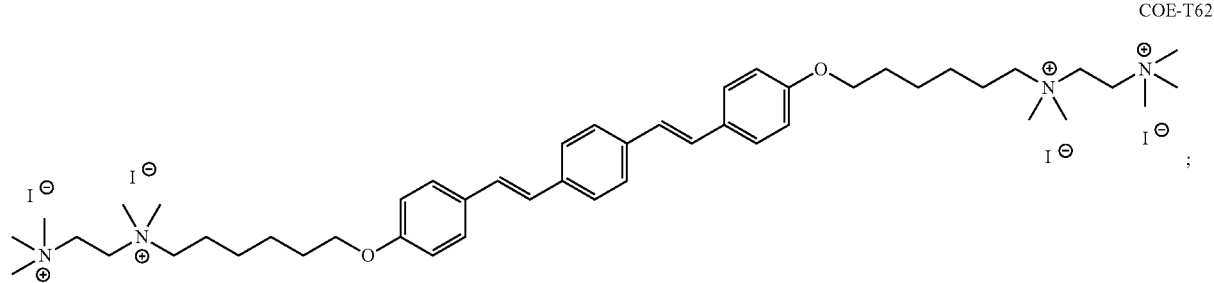
13. The compound according to Clause 12, wherein the compound of formula I is selected from the group consisting of:
COE-D42N
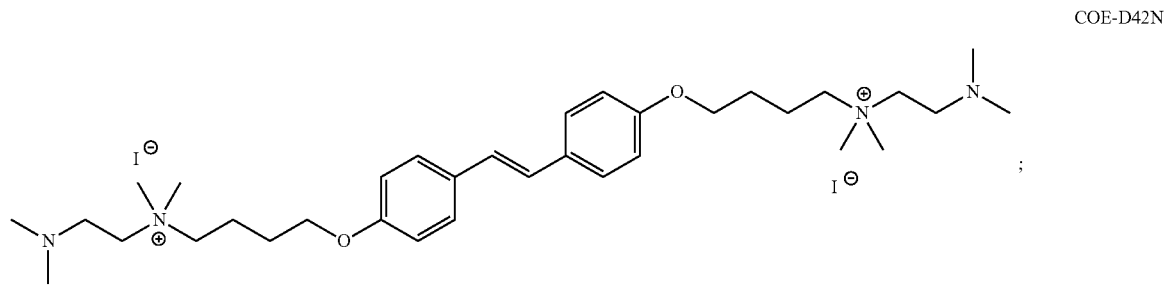
COE-D62N
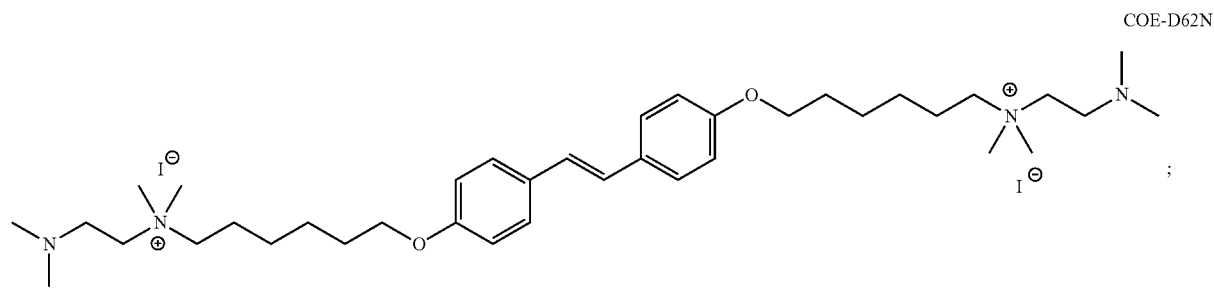
COE-D82N
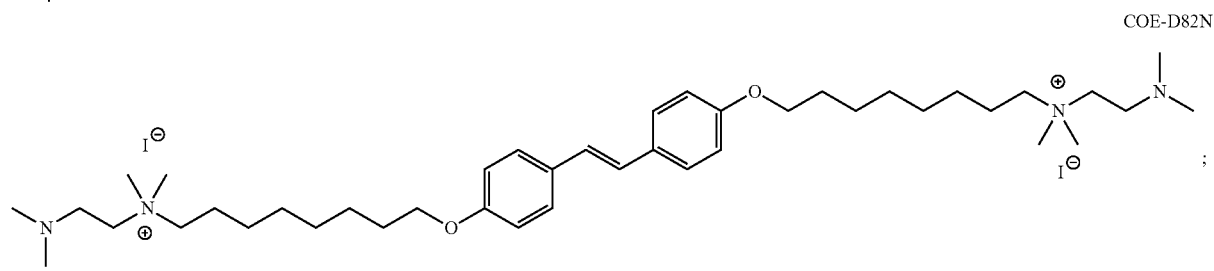
COE-T42N
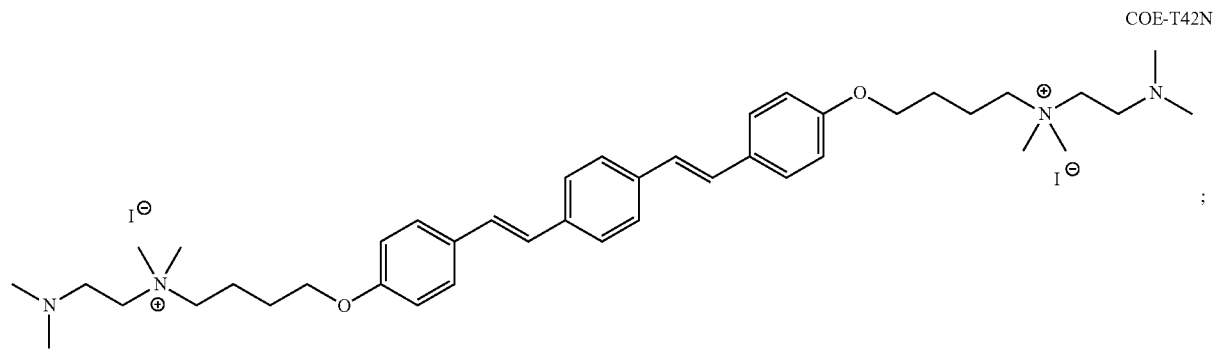

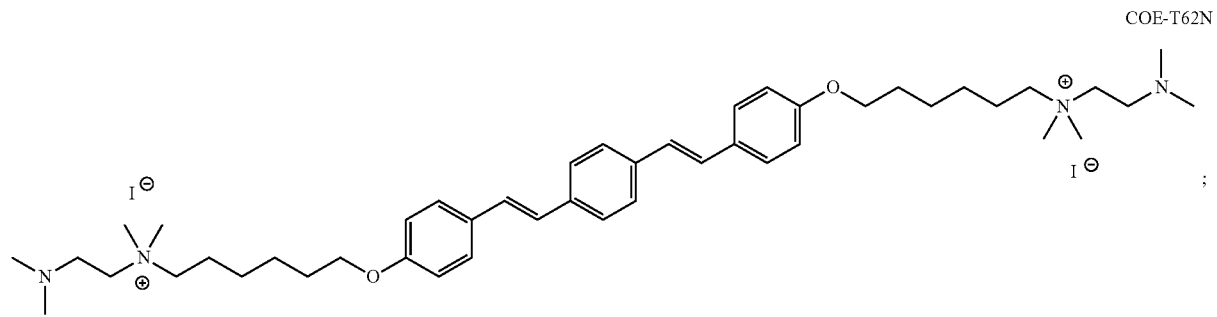
COE-T62N
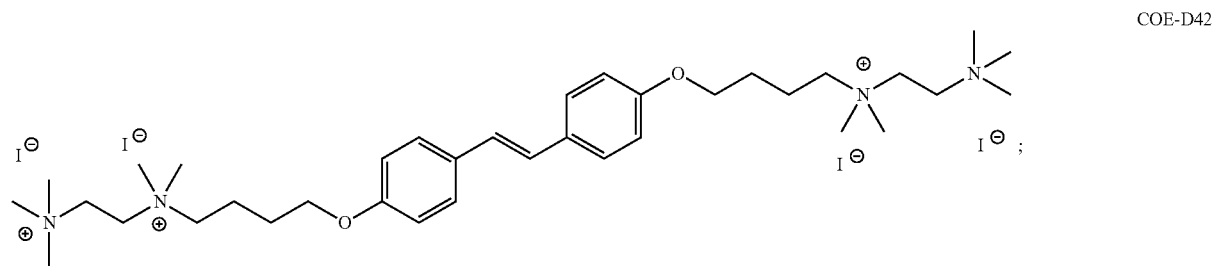
COE-D42
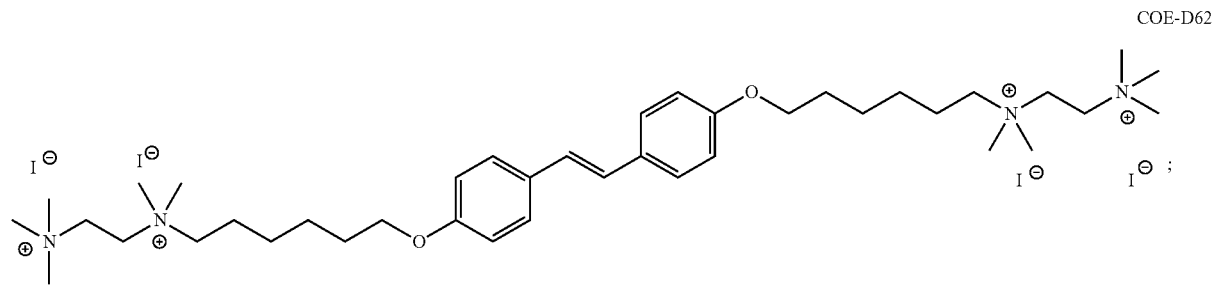
COE-D62
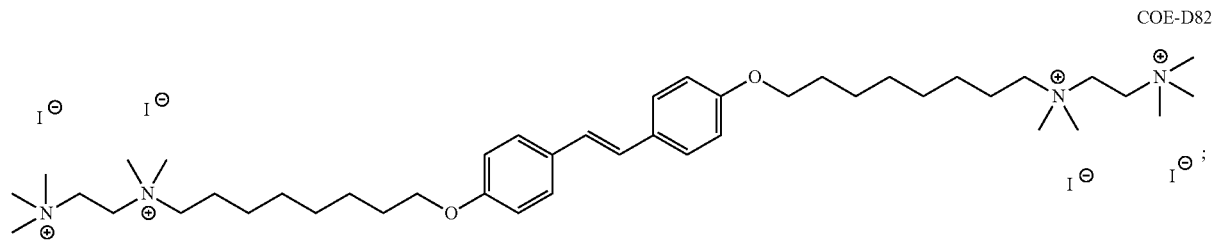
COE-D82
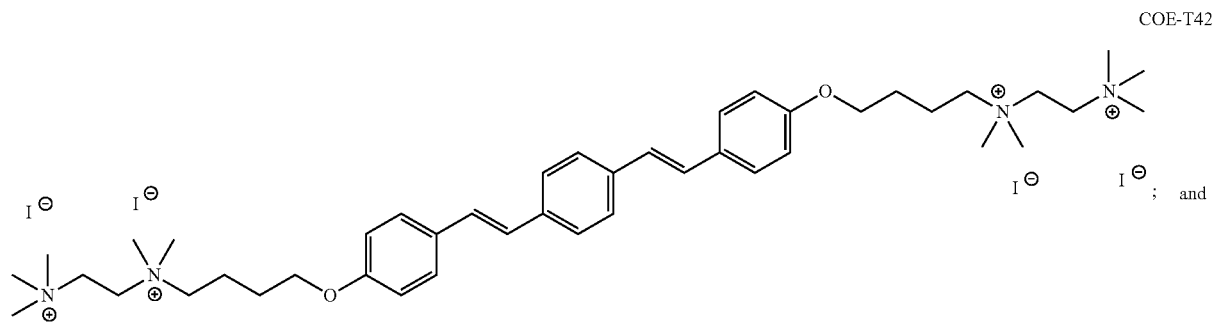
COE-T42
; and COE-T62
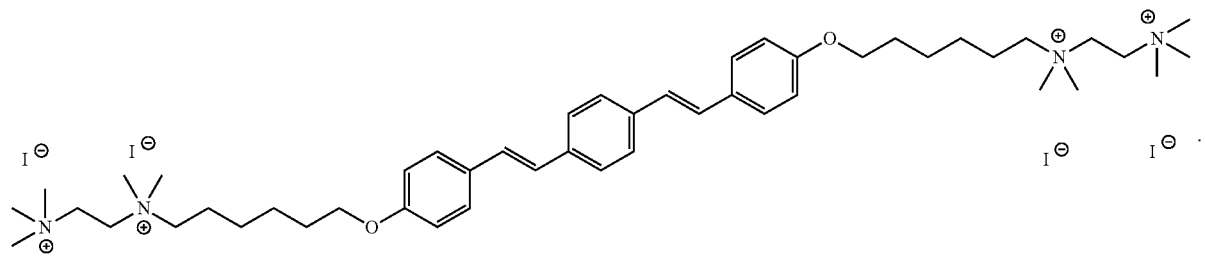
14. The compound according to Clause 13, wherein the compound of formula I is selected from the group consisting of:
COE-D42
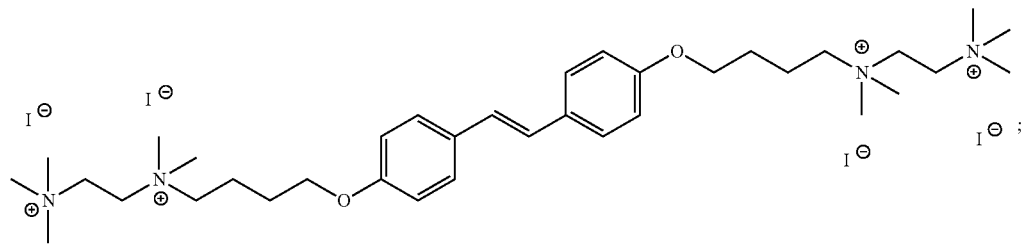
COE-D62
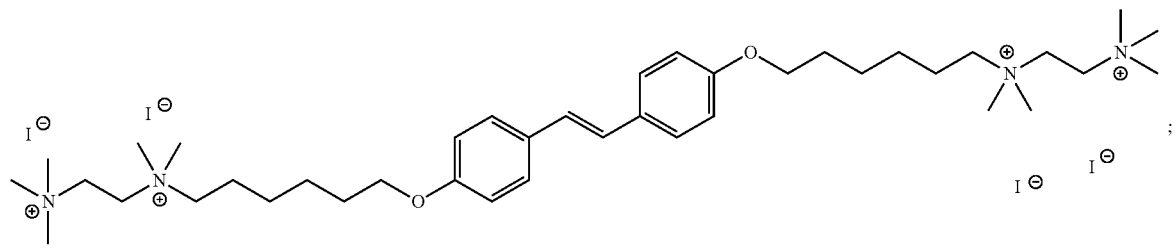
COE-D82
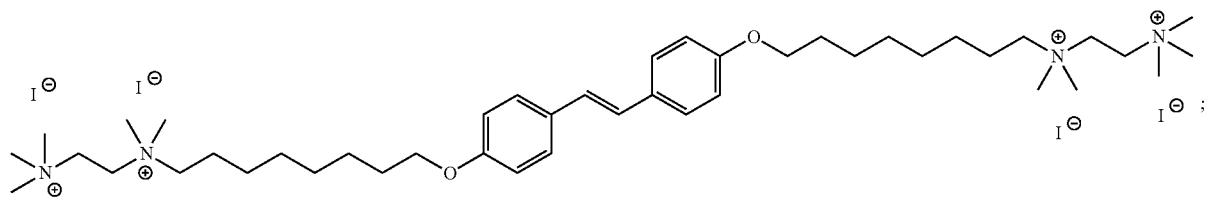
COE-T42
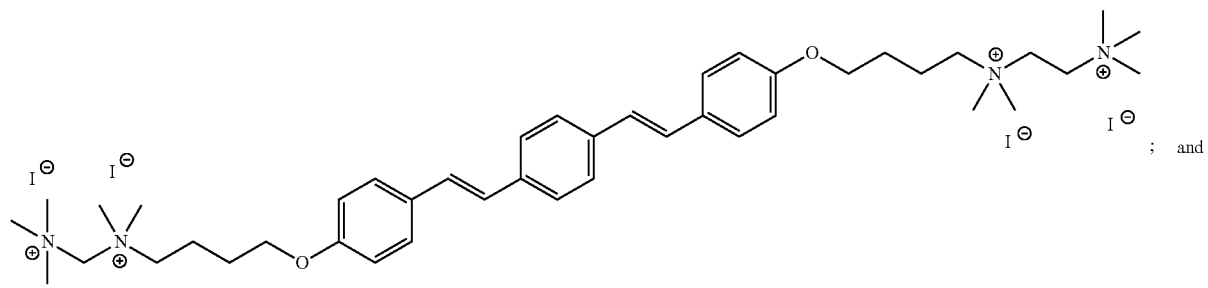
; and -continued

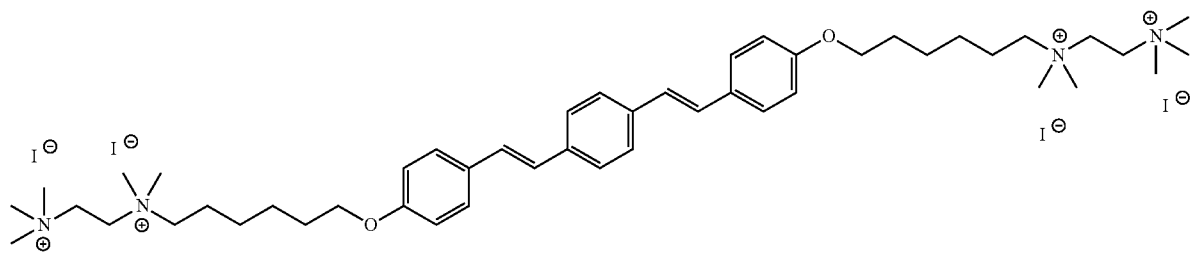

COE-T62

15. The compound according to any one of Clauses 1 to 10, wherein each X⁻ is a halide selected from the group consisting of Br⁻, Cl⁻, F⁻ and I⁻, optionally wherein each X⁻ is I⁻.

16. A pharmaceutical formulation comprising a compound of formula I as defined in any one of Clauses 1 to 15 and one or more of a pharmaceutically acceptable adjuvant, diluent or carrier.

17. A compound of formula I or a solvate thereof as defined in any one of Clauses 1 to 15 or a pharmaceutical formulation as defined in Clause 16 for use in medicine.

18. Use of a compound of formula I or a salt or solvate thereof as defined in any one of Clauses 1 to 15 or a pharmaceutical formulation as defined in Clause 16 for use in the preparation of a medicament to treat an infection, optionally wherein the infection is a microbial infection.

19. A method of treating an infection, the method including the step of administering a therapeutically effective amount of a compound of formula I or a salt or solvate thereof as defined in any one of Clauses 1 to 15 or a pharmaceutical formulation as defined in Clause 16 to a subject in need thereof, optionally wherein the infection is a microbial infection.

20. A compound of formula I or a salt or solvate thereof as defined in any one of Clauses 1 to 15 or a pharmaceutical formulation as defined in Clause 16 for use in the treatment of an infection, optionally wherein the infection is a microbial infection.

21. The use according to Clause 18, the method according to Clause 19 or the compound for use according to Clause 20, wherein the compound of formula I is selected from the group consisting of:

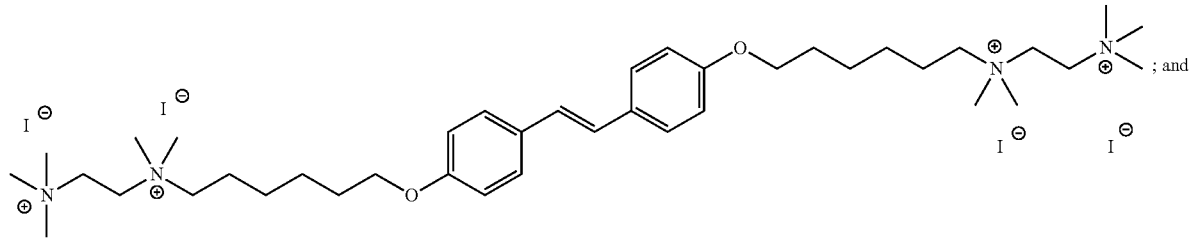

COE-D62

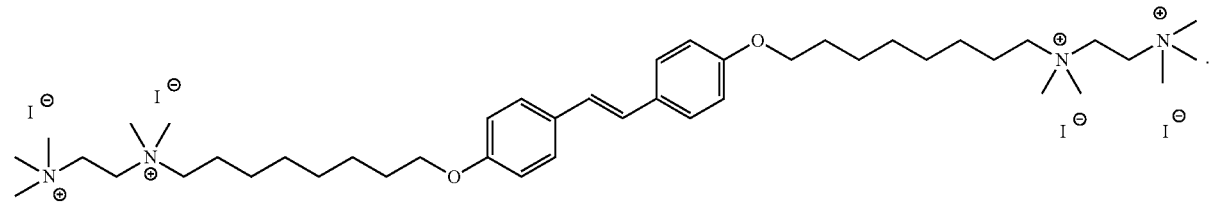

COE-D82

22. A method of removing a biofilm from a solid substrate or preventing build-up of a biofilm on a solid substrate, or killing, inhibiting, or dispersing microbes inhabiting said biofilm in a system susceptible to biofilm formation, said biofilm being formed by at least one microorganism, the method comprising the step of contacting the system with an effective amount of a compound of formula I or a salt or solvate thereof as defined in any one of Clauses 1 to 15 or a composition comprising a compound of formula I to remove the biofilm or prevent its formation.

23. A cosmetic or cleansing formulation, comprising a compound of formula I as defined in any one of Clauses 1 to 15 and one or more of an adjuvant, diluent or carrier suitable for use in a cosmetic or cleansing formulation.

BRIEF DESCRIPTION OF DRAWINGS

FIGS. 12*a* and *b* show the negative and positive controls, respectively.

DESCRIPTION

Figure 1A:
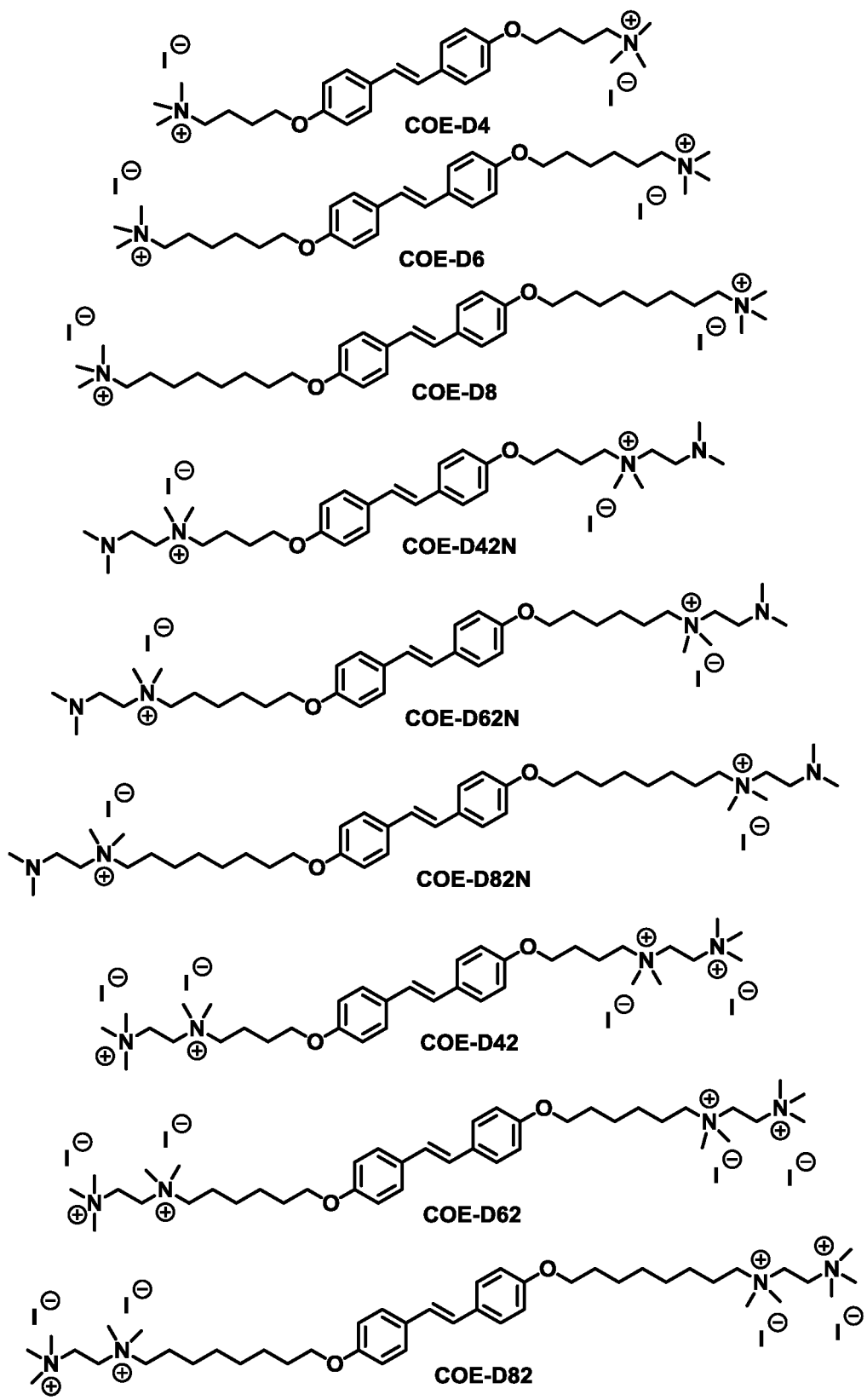
FIGS. 1A and 1B Depict the molecular structures of the conjugated oligoelectrolytes (COEs) of the current invention.

Thus, according to the first aspect of the invention, there is provided a compound of formula I:

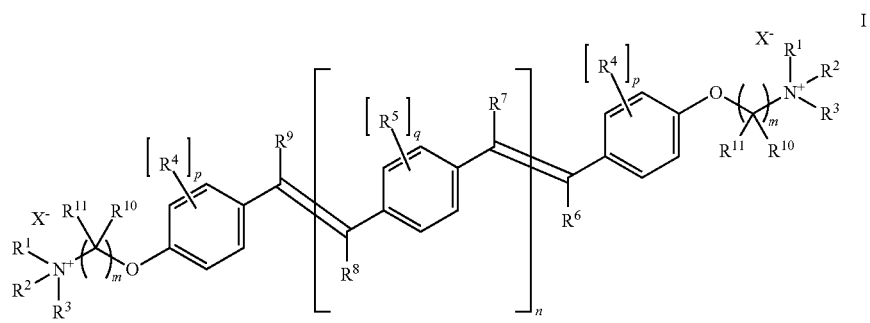

wherein:

n is 0 to 4;

m, at each occurrence, independently represents is 1 to 12;

p and q, at each occurrence, independently represents 0 to 4;

$R^1$, at each occurrence, independently represents a $C_{1-12}$ alkyl group, a —$(CH_2)_o$—$NR^{1'}R^{2'}$ group or a —$(CH_2)_{o'}$—$N^+R^{1'}R^{2'}R^{3'}$ group, the latter group's charge being balanced by an $X^-$; each $R^{1'}$, $R^2$, $R^3$, $R^{2'}$ and $R^{3'}$ are independently a $C_{1-12}$ alkyl group;

o and o' are 1 to 12;

each of $R^4$ to $R^9$, at each occurrence, independently represents:

(a) H;

(b) halo;

(c) CN;

(d) $C_{1-6}$ alkyl, $C_{2-6}$ alkenyl, $C_{2-6}$ alkynyl (which latter three groups are unsubstituted or substituted by one or more substituents selected from F, Cl, Br (e.g. Cl, F, such as F), nitro, CN, $C_{1-6}$ alkyl, $C_{2-6}$ alkenyl, $C_{2-6}$ alkynyl (which latter three groups are unsubstituted or substituted by one or more substituents selected from OH, =O, F, C, Br (e.g. Cl, F, such as F), $C_{1-4}$ alkyl and $C_{1-4}$ alkoxy), $Cy^1$ (which $Cy^1$ group is unsubstituted or is substituted by one or more substituents selected from F, Cl, Br (e.g. Cl, F, such as F), nitro, CN, $C_{1-6}$ alkyl, $C_{2-6}$ alkenyl, $C_{2-6}$ alkynyl (which latter three groups are optionally substituted by one or more substituents selected from OH, =O, F, Cl, Br (e.g. Cl, F, such as F), $C_{1-4}$ alkyl and $C_{1-4}$ alkoxy), $OR^{12a}$, $S(O)_rR^{12b}$, $S(O)_2NR^{12c}R^{12d}$, $NR^{12e}S(O)_2R^{12f}$, $NR^{12g}R^{12h}$, aryl and Het$^1$);

(e) $Cy^2$ (which $Cy^2$ group is unsubstituted or is substituted by one or more substituents selected from F, Cl, Br (e.g. Cl, F, such as F), nitro, CN, $C_{1-6}$ alkyl, $C_{2-6}$ alkenyl, C$_{2-6}$ alkynyl (which latter three groups are optionally substituted by one or more substituents selected from OH, =O, F, Cl, Br (e.g. Cl, F, such as F), C$_{1-4}$ alkyl and C$_{1-4}$ alkoxy), OR$^{13a}$, S(O)$_r$R$^{13b}$, S(O)$_2$NR$^{13c}$R$^{13d}$, NR$^{13e}$S(O)$_2$R$^{13f}$, NR$^{13g}$R$^{13h}$, aryl and Het$^2$), (f) Het$^a$ (which Het$^a$ group is unsubstituted or substituted by one or more substituents selected from halo, nitro, CN, C$_{1-6}$ alkyl, C$_{2-6}$ alkenyl, C$_{2-6}$ alkynyl (which latter three groups are optionally substituted by one or more substituents selected from OH, =O, F, C, Br (e.g. Cl, F, such as F), C$_{1-4}$ alkyl and C$_{1-4}$ alkoxy), OR$^{14a}$, S(O)$_r$R$^{14b}$, S(O)$_2$NR$^{14c}$R$^{14d}$ NR$^{14e}$S(O)$_2$R$^{14f}$, NR$^{14g}$R$^{14h}$, aryl and Het$^3$);

(g) OR$^{15a}$;
(h) S(O)$_r$R$^{15b}$;
(i) S(O)$_2$NR$^{15c}$R$^{15d}$;
(j) NR$^{15e}$S(O)$_2$R$^{15f}$; and
(1) NR$^{15g}$R$^{15h}$;

R$^{10}$ and R$^{11}$, at each occurrence, independently represents:
(i) H;
(ii) F, Cl or Br (e.g. Cl, F, such as F);
(iii) CN;
(iv) C$_{1-6}$ alkyl, C$_{2-6}$ alkenyl, C$_{2-6}$ alkynyl (which latter three groups are unsubstituted or substituted by one or more substituents selected from F, Cl, Br (e.g. Cl, F, such as F), nitro, CN, C$_{1-6}$ alkyl, C$_{2-6}$ alkenyl, C$_{2-6}$ alkynyl (which latter three groups are unsubstituted or substituted by one or more substituents selected from OH, =O, F, C, Br (e.g. Cl, F, such as F), C$_{1-4}$ alkyl and C$_{1-4}$ alkoxy), Cy$^{1'}$ (which Cy$^{1'}$ group is unsubstituted or is substituted by one or more substituents selected from F, Cl, Br (e.g. Cl, F, such as F), nitro, CN, C$_{1-6}$ alkyl, C$_{2-6}$ alkenyl, C$_{2-6}$ alkynyl (which latter three groups are optionally substituted by one or more substituents selected from OH, =O, F, C, Br (e.g. Cl, F, such as F), C$_{1-4}$ alkyl and C$_{1-4}$ alkoxy), OR$^{12a'}$, S(O)$_r$R$^{12b'}$, S(O)$_2$NR$^{12c'}$R$^{12d'}$, NR$^{12e'}$S(O)$_2$R$^{12f'}$, NR$^{12'}$R$^{12h'}$, aryl and Het$^{1'}$);

(v) Cy$^{2'}$ (which Cy$^{2'}$ group is unsubstituted or is substituted by one or more substituents selected from F, Cl, Br (e.g. Cl, F, such as F), nitro, CN, C$_{1-6}$ alkyl, C$_{2-6}$ alkenyl, C$_{2-6}$ alkynyl (which latter three groups are optionally substituted by one or more substituents selected from OH, =O, F, C, Br (e.g. Cl, F, such as F), C$_{1-4}$ alkyl and C$_{1-4}$ alkoxy), OR$^{13a'}$, S(O)$_r$R$^{13b'}$, S(O)$_2$NR$^{13c'}$R$^{13d'}$, NR$^{13e'}$S(O)$_2$R$^{13}$, NR$^{13'}$R$^{13h'}$, aryl and Het$^{2'}$), (vi) Het$^{a'}$ (which Het$^{a'}$ group is unsubstituted or substituted by one or more substituents selected from halo, nitro, CN, C$_{1-6}$ alkyl, C$_{2-6}$ alkenyl, C$_{2-6}$ alkynyl (which latter three groups are optionally substituted by one or more substituents selected from OH, =O, F, C, Br (e.g. Cl, F, such as F), C$_{1-4}$ alkyl and C$_{1-4}$ alkoxy), OR$^{14a'}$, S(O)$_r$R$^{14b'}$, S(O)$_2$NR$^{14c'}$R$^{14d'}$, NR$^{14e'}$S(O)$_2$R$^{14f'}$NR$^{14g'}$R$^{14h'}$, aryl and Het$^{3'}$);

(vii) OR$^{15a'}$;
(viii) S(O)$_r$R$^{15b'}$;
(ix) S(O)$_2$NR$^{15c'}$R$^{15d'}$;
(x) NR$^{15e'}$S(O)$_2$R$^{15f'}$;
(xi) NR$^{15g'}$R$^{15h'}$ R$^{12a}$ to R$^{12h}$, R$^{13a}$ to R$^{13h}$, R$^{14a}$ to R$^{14h}$, R$^{15a}$ to R$^{15h}$, R$^{12a'}$ to R$^{12h'}$, R$^{13'}$ to R$^{13h'}$, R$^{14a'}$ to R$^{14'}$, R$^{15a'}$ to R$^{5h'}$, independently represent, at each occurrence, H, C$_{1-6}$ alkyl, C$_{2-6}$ alkenyl, C$_{2-6}$ alkynyl (which latter three groups are optionally substituted by one or more substituents selected from F, Cl, Br (e.g. Cl, F, such as F), nitro, =O, C(O)OC$_{1-4}$ alkyl, CN, C$_{1-6}$ alkyl, C$_{2-6}$ alkenyl, C$_{2-6}$ alkynyl, C$_3$ cycloalkyl (which latter three groups are optionally substituted by one or more substituents selected from OH, =O, F, C, Br (e.g. Cl, F, such as F), C$_{1-4}$ alkyl and C$_{1-4}$ alkoxy), OR$^{16}$, S(O)R$^{16b}$, S(O)$_2$NR$^{16c}$R$^{16d}$, NR$^{16e}$S(O)$_2$R$^{16f}$, NR$^{16g}$R$^{16h}$, aryl and Het$^4$), C$_{3-10}$ cycloalkyl, or C$_{4-10}$ cycloalkenyl (which latter two groups are optionally substituted by one or more substituents selected from F, Cl, Br (e.g. Cl, F, such as F), OH, =O, C$_{1-6}$ alkyl and C$_{1-6}$ alkoxy) or Het$^b$;

R$^{16a}$ to R$^{16h}$ independently represent at each occurrence, H, C$_{1-4}$ alkyl, C$_{2-4}$ alkenyl, C$_{2-4}$ alkynyl which latter three groups are optionally substituted by one or more substituents selected from F, Cl, Br (e.g. Cl, F, such as F), nitro, CN, C$_{1-4}$ alkyl, C$_{2-4}$ alkenyl, C$_{2-4}$ alkynyl (which latter three groups are optionally substituted by one or more substituents selected from OH, =O, F, C, Br (e.g. Cl, F, such as F), C$_{1-4}$ alkyl and C$_{1-4}$ alkoxy), C$_{1-6}$ cycloalkyl, or C$_{4-6}$ cycloalkenyl (which latter two groups are optionally substituted by one or more substituents selected from F, Cl, Br (e.g. Cl, F, such as F), OH, =O, C$_{1-4}$ alkyl and C$_{1-4}$ alkoxy), Het$^1$ to Het$^4$, Het$^{1'}$ to Het$^{3'}$, Het$^a$, Het$^b$ and Het$^{a'}$ independently represent a 4- to 14-membered heterocyclic groups containing one or more heteroatoms selected from O, S and N, which heterocyclic groups may comprise one, two or three rings and may be substituted by one or more substituents selected from =O, or more particularly, halo, C$_{1-6}$ alkyl, which latter group is optionally substituted by one or more substituents selected from F, C, Br (e.g. Cl, F, such as F), —OR$^{17a}$, —NR$^{17}$R$^{17c}$, —C(O)OR$^{17d}$ and —C(O)NR$^{17e}$R$^{17f}$;

R$^{17a}$ to R$^{17f}$ independently represent at each occurrence, H, C$_{1-4}$ alkyl, C$_{2-4}$ alkenyl, C$_{2-4}$ alkynyl which latter three groups are optionally substituted by one or more substituents selected from F, Cl, Br (e.g. Cl, F, such as F), nitro, CN, C$_{1-4}$ alkyl, C$_{2-4}$ alkenyl, C$_{2-4}$ alkynyl (which latter three groups are optionally substituted by one or more substituents selected from OH, =O, F, C, Br (e.g. Cl, F, such as F), C$_{1-4}$ alkyl and C$_{1-4}$ alkoxy), C$_{3-6}$ cycloalkyl, or C$_{1-6}$ cycloalkenyl (which latter two groups are optionally substituted by one or more substituents selected from F, Cl, Br (e.g. Cl, F, such as F), OH, =O, C$_{1-4}$ alkyl and C$_{1-4}$ alkoxy), Cy$^1$, Cy$^2$, Cy$^{1'}$ and Cy$^{2'}$, at each occurrence, independently represents a 3- to 10-membered aromatic, fully saturated or partially unsaturated carbocyclic ring;

each r independently represents 0, 1 or 2; and each X$^-$ is a pharmaceutically acceptable anion, or a pharmaceutically acceptable solvate thereof.

In embodiments herein, the word "comprising" may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

References herein (in any aspect or embodiment of the invention) to compounds of formula I includes references to such compounds per se, to tautomers of such compounds, as well as to pharmaceutically acceptable salts or solvates, or pharmaceutically functional derivatives of such compounds.

Pharmaceutically acceptable anions that may be mentioned include anions derivable from acid addition salts. In the current invention, the salts may be formed simply by the reactions used to form the compounds (e.g. the use of alkyl halides to form the quaternary ammonium species). Salts may also be prepared by exchanging a counter-ion of a compound of formula I in the form of a salt with another counter-ion, for example using a suitable ion exchange resin.

The salt may be formed in the presence of a solvent or in a medium in which the resulting salt is insoluble, followed by removal of said solvent, or said medium, using standard techniques (e.g. in vacuo, by freeze-drying or by filtration).

Examples of pharmaceutically acceptable salts that may be used herein include acid addition salts derived from mineral acids and organic acids.

Examples of acid addition salts include acid addition salts formed with acetic, 2,2-dichloroacetic, adipic, alginic, aryl sulphonic acids (e.g. benzenesulphonic, naphthalene-2-sulphonic, naphthalene-1,5-disulphonic and p-toluenesulphonic), ascorbic (e.g. L-ascorbic), L-aspartic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, tartaric (e.g. (+)-L-tartaric), thiocyanic, undecylenic and valeric acids.

Particular examples of salts are salts derived from mineral acids such as hydroiodic, hydrochloric, hydrobromic, phosphoric, metaphosphoric, nitric and sulphuric acids; from organic acids, such as tartaric, acetic, citric, malic, lactic, fumaric, benzoic, glycolic, gluconic, succinic, arylsulphonic acids.

As will be appreciated, the salts formed in the compounds of formula I may only make use of the anionic portion of the acids mentioned above.

As will be appreciated herein, the compounds of formula I are inherently presented as salt forms, which may also include solvates. Thus, when "pharmaceutically acceptable salts" of the compounds of formula I are referred to herein it is intended to refer to compounds of formula I that include one or more further functional groups that are capable of forming a salt (e.g. an amino group or the like). These additional functional groups may form pharmaceutically acceptable salts with a suitable acid addition salt, as described hereinbefore.

As mentioned above, also encompassed by formula I are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGA), differential scanning calorimetry (DSC) and X-ray crystallography.

The solvates can be stoichiometric or non-stoichiometric solvates. Particularly preferred solvates are hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, IN, USA, 1999, ISBN 0-967-06710-3.

Compounds of formula I, as well as pharmaceutically acceptable salts and solvates of such compounds are, for the sake of brevity, hereinafter referred to together as the "compounds of formula I".

Compounds of formula I may contain double bonds and may thus exist as E (entgegen) and Z (zusammen) geometric isomers about each individual double bond. All such isomers and mixtures thereof are included within the scope of the invention.

Compounds of formula I may exist as regioisomers and may also exhibit tautomerism. All tautomeric forms and mixtures thereof are included within the scope of the invention.

Compounds of formula I may contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

Unless otherwise stated, the term "alkyl" refers to an unbranched or branched, cyclic, saturated or unsaturated (so forming, for example, an alkenyl or alkynyl) hydrocarbyl radical, which may be substituted or unsubstituted (with, for example, one or more halo atoms). Where the term "alkyl" refers to an acyclic group, it is preferably $C_{1-10}$ alkyl and, more preferably, $C_{1-6}$ alkyl (such as ethyl, propyl, (e.g. n-propyl or isopropyl), butyl (e.g. branched or unbranched butyl), pentyl or, more preferably, methyl). Where the term "alkyl" is a cyclic group (which may be where the group "cycloalkyl" is specified), it is preferably $C_{3-12}$ cycloalkyl and, more preferably, $C_{5-10}$ (e.g. $C_{5-7}$) cycloalkyl.

Unless otherwise stated, the term "alkylene" refers to an unbranched or branched $C_{1-10}$ (e.g. $C_{1-6}$) alkylene and, preferably $C_{1-3}$ alkylene, such as pentylene, butylene (branched or unbranched), preferably, propylene (n-propylene or isopropylene), ethylene or, more preferably, methylene (i.e. —CH$_2$—).

The term "halo", when used herein, includes references to fluoro, chloro, bromo and iodo.

Unless otherwise stated, the term "aryl" when used herein includes $C_{6-14}$ (such as $C_{6-10}$) aryl groups. Such groups may be monocyclic, bicyclic or tricyclic and have between 6 and 14 ring carbon atoms, in which at least one ring is aromatic. The point of attachment of aryl groups may be via any atom of the ring system. However, when aryl groups are bicyclic or tricyclic, they are linked to the rest of the molecule via an aromatic ring. $C_{6-14}$ aryl groups include phenyl, naphthyl and the like, such as 1,2,3,4-tetrahydronaphthyl, indanyl, indenyl and fluorenyl. Embodiments of the invention that may be mentioned include those in which aryl is phenyl.

Heterocyclic (Het$^1$ to Het$^4$, Het$^{1'}$ to Het, Het$^a$, Het$^b$ and Het$^{a'}$) groups may be fully saturated, partly unsaturated, wholly aromatic or partly aromatic in character. Values of Het to Het$^4$, Het$^{1'}$ to Het$^{3'}$, Het$^a$, Het$^b$ and Het$^{a'}$ groups that may be mentioned include acridinyl, 1-azabicyclo[2.2.2]octanyl, azetidinyl, benzimidazolyl, benzisothiazolyl, benzisoxazolyl, benzodioxanyl, benzodioxepanyl, benzodioxepinyl, benzodioxolyl, benzofuranyl, benzofurazanyl, benzo[c]isoxazolidinyl, benzomorpholinyl, 2,1,3-benzoxadiazolyl, benzoxazinyl (including 3,4-dihydro-2H-1,4-benzoxazinyl), benzoxazolidinyl, benzoxazolyl, benzopyrazolyl, benzo[e]pyrimidine, 2,1,3-benzothiadiazolyl, benzothiazolyl, benzothienyl, benzotriazolyl, carbazolyl, chromanyl, chromenyl, cinnolinyl, 2,3-dihydrobenzimidazolyl, 2,3-dihydrobenzo[6]furanyl, 1,3-dihydrobenzo[c]furanyl, 1,3-dihydro-2,1-benzisoxazolyl, 2,3-dihydropyrrolo[2,3-b]pyridinyl, dioxanyl, furanyl, furazanyl, hexahydropyrimidinyl, hydantoinyl, imidazolyl, imidazo[1,2-a]pyridinyl, imidazo[2,3-b]thiazolyl, indazolyl, indolinyl, indolyl, isobenzofuranyl, isochromanyl, isoindolinyl, isoindolyl, isoquinolinyl, isothiaziolyl, isothiochromanyl, isoxazolidinyl, isoxazolyl, maleimido, morpholinyl, naphtho[1,2-b]furanyl, naphthyridinyl (including 1,6-naphthyridinyl or, particularly, 1,5-naphthyridinyl and 1,8-naphthyridinyl), oxadiazolyl, 1,2- or 1,3-oxazinanyl, oxazolyl, oxetanyl, phenazinyl, phenothiazinyl, phthalazinyl, piperazinyl, piperidinyl, pteridinyl, purinyl, pyranyl, pyrazinyl, pyrazolyl, pyridazinyl, pyridinyl, pyrimidinyl, pyrrolidinonyl, pyrrolidinyl, pyrrolinyl, pyrrolo[2,3-b]pyridinyl, pyrrolo[5,1-b]pyridinyl, pyrrolo[2,3-c]pyridinyl, pyrrolyl, quinazolinyl, quinolinyl, quinolizinyl, quinoxalinyl, sulfolanyl, 3-sulfolenyl, 4,5,6,7-tetrahydrobenzimidazolyl, 4,5,6,7-tetrahydrobenzopyrazolyl, 5,6,7,8-tetrahydrobenzo[e]pyrimidine, tetrahydrofuranyl, tetrahydroisoquinolinyl (including 1,2,3,4-tetrahydroisoquinolinyl and 5,6,7,8-tetrahydroisoquinolinyl), tetrahydropyranyl, 3,4,5,6-tetrahydropyridinyl, 1,2,3,4-tetrahydropyrimidinyl, 3,4,5,6-tetrahydropyrimidinyl, tetrahydroquinolinyl (including 1,2,3,4-tetrahydroquinolinyl and 5,6,7,8-tetrahydroquinolinyl), tetrazolyl, thiadiazolyl, thiazolidinyl, thiazolyl, thienyl, thieno[5,1-c]pyridinyl, thiochromanyl, thiophenetyl, triazolyl, 1,3,4-triazolo[2,3-b]pyrimidinyl, xanthenyl and the like. Particular values of (Het$^1$ to Het$^3$ (e.g. Het to Het$^7$) and Het$^a$ to Het$^c$ that may be mentioned include the 4- to 10-membered heterocyclic groups from the list above. Further, values of (Het$^1$ to Het$^3$ (e.g. Het$^1$ to Het$^7$) and Het$^a$ to Het$^c$ that may be mentioned include the 5- and 8-membered (e.g. 5- to 6-membered) heterocyclic groups from the list above.

Substituents on heterocyclic (Het$^1$ to Het$^4$, Het$^{1'}$ to Het$^{3'}$, Het$^a$, Het$^b$ and Het$^{a'}$) groups may, where appropriate, be located on any atom in the ring system including a heteroatom. The point of attachment of heterocyclic (Het$^1$ to Het$^4$, Het$^{1'}$ to Het$^{3'}$, Het$^a$, Het$^b$ and Het$^{a'}$) groups may be via any atom in the ring system including (where appropriate) a heteroatom (such as a nitrogen atom), or an atom on any fused carbocyclic ring that may be present as part of the ring system. Heterocyclic (Het$^1$ to Het$^4$, Het$^{1'}$ to Het$^{3'}$, Het$^a$, Het$^b$ and Het$^{a'}$) groups may also be in the N- or S-oxidised form.

For the avoidance of doubt, in cases in which the identity of two or more substituents in a compound of formula I may be the same, the actual identities of the respective substituents are not in any way interdependent.

Embodiments of the invention that may be mentioned include those that relate to compounds of formula I in which:
(1) $R^4$ to $R^9$, at each occurrence, independently represents:
 (ia) H;
 (ib) Br, Cl, F;
 (ic) $C_{1-4}$ alkyl which is unsubstituted or substituted by one or more substituents selected from F, Cl, Br (e.g. Cl, F, such as F), nitro, CN, $C_{1-3}$ alkyl (which latter group is unsubstituted or substituted by one or more substituents selected from OH, =O, F, Cl, Br (e.g. Cl, F, such as F), $C_{1-4}$ alkyl and $C_{1-4}$ alkoxy), Cy$^1$ (which Cy$^1$ group is unsubstituted or is substituted by one or more substituents selected from F, Cl, Br (e.g. Cl, F, such as F), CN, $C_{1-3}$ alkyl (which latter group is unsubstituted or substituted by one or more substituents selected from OH, =O, F, C, Br (e.g. Cl, F, such as F), $C_{1-4}$ alkyl and $C_{1-4}$ alkoxy), OR$^{12a}$, NR$^{12g}$R$^{12h}$, aryl and Het$^1$);
 (id) Cy$^2$ (which Cy$^2$ group is unsubstituted or is substituted by one or more substituents selected from F, Cl, Br (e.g. Cl, F, such as F), CN, $C_{1-3}$ alkyl (which latter group is optionally substituted by one or more substituents selected from OH, =O, F, Cl, Br (e.g. Cl, F, such as F), $C_{1-4}$ alkyl and $C_{1-4}$ alkoxy), OR$^{13a}$, NR$^{13g}$R$^{13h}$, aryl and Het$^2$);
 (ie) Het$^a$ (which Het$^a$ group is unsubstituted or substituted by one or more substituents selected from halo, nitro, CN, $C_{1-3}$ alkyl (which latter group is optionally substituted by one or more substituents selected from OH, =O, halo, $C_{1-4}$ alkyl and $C_{1-4}$ alkoxy), OR$^{14a}$, NR$^{14g}$R$^{14h}$, aryl and Het$^3$);
 (if) OR$^{15a}$; or
 (ig) NR$^{15g}$R$^{15h}$,
 (e.g. wherein $R^4$ to $R^9$, at each occurrence, independently represents:
 (iA) H;
 (iB) Br, Cl, F;
 (iC) $C_{1-4}$ alkyl which is unsubstituted or substituted by one or more substituents selected from F, C, Br (e.g. Cl, F, such as F), $C_{1-3}$ alkyl (which latter group is unsubstituted or substituted by one or more substituents selected from OH, =O, F, Cl, Br (e.g. Cl, F, such as F), $C_{1-4}$ alkyl and $C_{1-4}$ alkoxy), OR$^{12a}$ and NR$^{12g}$R$^{12h}$)
 (iD) OR$^{15a}$; or
 (iE) NR$^{15g}$R$^{15h}$,
 such as $R^4$ to $R^9$, at each occurrence, represents H);
(II) $R^{10}$ and $R^{11}$, at each occurrence, independently represents:
 (ai) H;
 (bi) Br, Cl, F;
 (ci) $C_{1-4}$ alkyl which is unsubstituted or substituted by one or more substituents selected from F, Cl, Br (e.g. Cl, F, such as F), nitro, CN, $C_{1-3}$ alkyl (which latter group is unsubstituted or substituted by one or more substituents selected from OH, =O, F, Cl, Br (e.g. CI, F, such as F), $C_{1-4}$ alkyl and $C_{1-4}$ alkoxy), Cy$^1$ (which Cy$^1$ group is unsubstituted or is substituted by one or more substituents selected from F, Cl, Br (e.g. Cl, F, such as F), CN, $C_{1-3}$ alkyl (which latter group is unsubstituted or substituted by one or more substituents selected from OH, =O, F, C, Br (e.g. Cl, F, such as F), $C_{1-4}$ alkyl and $C_{1-4}$ alkoxy), OR$^{12a'}$, NR$^{12g'}$R$^{12h'}$, aryl and Het$^{1'}$);

(di) Cy$^{2'}$ (which Cy$^{2'}$ group is unsubstituted or is substituted by one or more substituents selected from F, Cl, Br (e.g. Cl, F, such as F), CN, C$_{1-3}$ alkyl (which latter group is optionally substituted by one or more substituents selected from OH, =O, F, Cl, Br (e.g. Cl, F, such as F), C$_{1-4}$ alkyl and C$_{1-4}$ alkoxy), OR$^{13a'}$, NR$^{13g'}$R$^{13h'}$ aryl and Het$^{2'}$);
(ei) Het$^{a'}$ (which Het$^{a'}$ group is unsubstituted or substituted by one or more substituents selected from halo, nitro, CN, C$_{1-3}$ alkyl (which latter group is optionally substituted by one or more substituents selected from OH, =O, halo, C$_{1-4}$ alkyl and C$_{1-4}$ alkoxy), OR$^{4a}$, NR$^{4g'}$R$^{14h'}$, aryl and Het$^{3'}$);
(fi) OR$^{15a'}$; or
(gi) NR$^{15g'}$R$^{15h'}$,
(e.g. wherein R$^{10}$ and R$^{11}$, at each occurrence, independently represents:
(A) H;
(B) Br, Cl, F;
(C) C$_{1-4}$ alkyl which is unsubstituted or substituted by one or more substituents selected from F, C, Br (e.g. Cl, F, such as F), C$_{1-3}$ alkyl (which latter group is unsubstituted or substituted by one or more substituents selected from OH, =O, F, Cl, Br (e.g. Cl, F, such as F), C$_{1-4}$ alkyl and C$_{1-4}$ alkoxy), OR$^{12a'}$ and NR$^{12g'}$R$^{12h'}$);
(D) OR$^{15a'}$; or
(E) NR$^{15g'}$R$^{15h'}$, such as R$^{10}$ and R$^{11}$, at each occurrence, represents H).

In embodiments of the invention where the substituents F, Cl and Br are listed herein, C and, more particularly, F may be preferred. That is, the term "F, Cl or Br" may be replaced by "Cl, F" or, more particularly, by "F" at each occurrence thereof.

In particular embodiments of the invention that may be mentioned herein, p and q are 0 and each of R$^6$ to R$^{11}$ may be H.

In yet further embodiments of the invention that may be mentioned include those that relate to compounds of formula I in which:
(AA) n is 0 or 1;
(AB) m is 4 to 8;
(AC) o, when present, is 2 to 4, such as 2;
(AD) o', when present, is 2 to 4, such as 2;
(AE) X$^-$ is a halide selected from the group consisting of Br$^-$, Cl$^-$, F$^-$ and I$^-$, optionally wherein each X$^-$ is I$^-$.

In still further embodiments of the invention:
(aA) each of R$^1$ to R$^3$ is methyl;
(aB) R$^1$ is a —(CH$_2$)$_o$—NR$^{1'}$R$^{2'}$ or a —(CH$_2$)$_o$—N$^+$R$^{1'}$R$^{2'}$R$^{3'}$ group and R$^2$ and R$^3$ are a C$_{1-12}$ alkyl group, such as a methyl group; or (aC) R$^1$ is a —(CH$_2$)$_o$—N$^+$R$^{1'}$R$^{2'}$R$^{3'}$ group and R$^2$ and R$^3$ are both methyl groups.

In embodiments of the invention where R$^1$ is a —(CH$_2$)$_o$—NR$^{1'}$R$^{2'}$ group or a —(CH$_2$)$_o$—N$^+$R$^{1'}$R$^{2'}$R$^{3'}$ group, each R$^{1'}$, R$^{2'}$ and R$^{3'}$ may be a C$_1$ to C$_4$ alkyl group, such as a methyl group.

In particular embodiments of the invention that may be disclosed herein, the compound of formula I may be one in which:
n is 0 or 1;
m is 4, 6 or 8;
each R$^1$ is a —(CH$_2$)$_o$—NR$^{1'}$R$^{2'}$ group or a —(CH$_2$)$_o$—N$^+$R$^{1'}$R$^{2'}$R$^{3'}$ group, the latter group's charge being balanced by an X$^-$;
each R$^{1'}$, R$^2$, R$^3$, R$^{2'}$ and R$^{3'}$ are independently a C$_{1-4}$ alkyl group; and
o and o' are 2 to 3.

In particular embodiments of the invention that may be disclosed herein, the compound of formula I may be one in which:
p and q are 0;
n is 0 or 1;
m is 4, 6 or 8;
each R$^1$ is a —(CH$_2$)$_o$—NR$^{1'}$R$^{2'}$ group or a —(CH$_2$)$_o$—N$^+$R$^{1'}$R$^{2'}$R$^{3'}$ group, the latter group's charge being balanced by an X$^-$;
each R$^{1'}$, R$^2$, R$^3$, R$^{2'}$ and R$^{3'}$ are independently a C$_{1-4}$ alkyl group;
each of R$^6$ to R$^{11}$ is H; and
o and o' are 2 to 3.

In certain embodiments of the invention as described above, the compound of formula I, may be a compound of formula Ia:

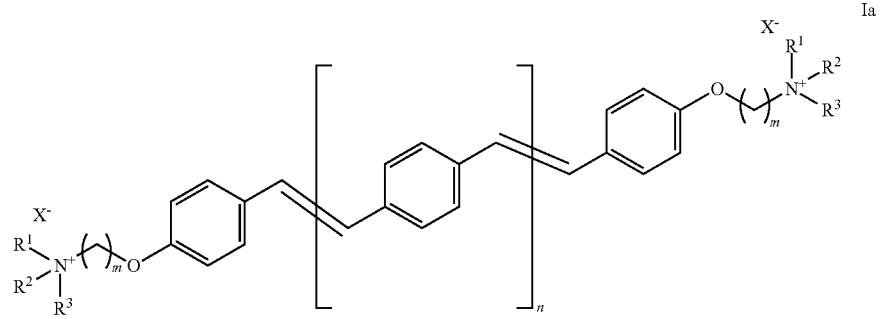

Ia

As will be appreciated, n, m, X$^-$ and R$^1$ to R$^3$ may be defined in accordance with any of the embodiments of the invention described above.

In embodiments of the invention, compounds of formula I may be ones in which:
when n is 0 and m is 4 to 8, then R$^1$ is a —(CH$_2$)$_o$—NR$^{1'}$R$^{2'}$ group or a —(CH$_2$)$_o$—N$^+$R$^{1'}$R$^{2'}$R$^{3'}$ group; and/or
when n is 0 and m is 1 to 12, then R$^1$ is a —(CH$_2$)$_o$—NR$^{1'}$R$^{2'}$ group or a —(CH$_2$)$_o$—N$^+$R$^{1'}$R$^{2'}$R$^{3'}$ group; and/or
the compound of formula I is not COE-D4, DOE-D6 or COE-D8.

Embodiments of the invention that may be mentioned include those in which the compound of formula I is a compound selected from the list:

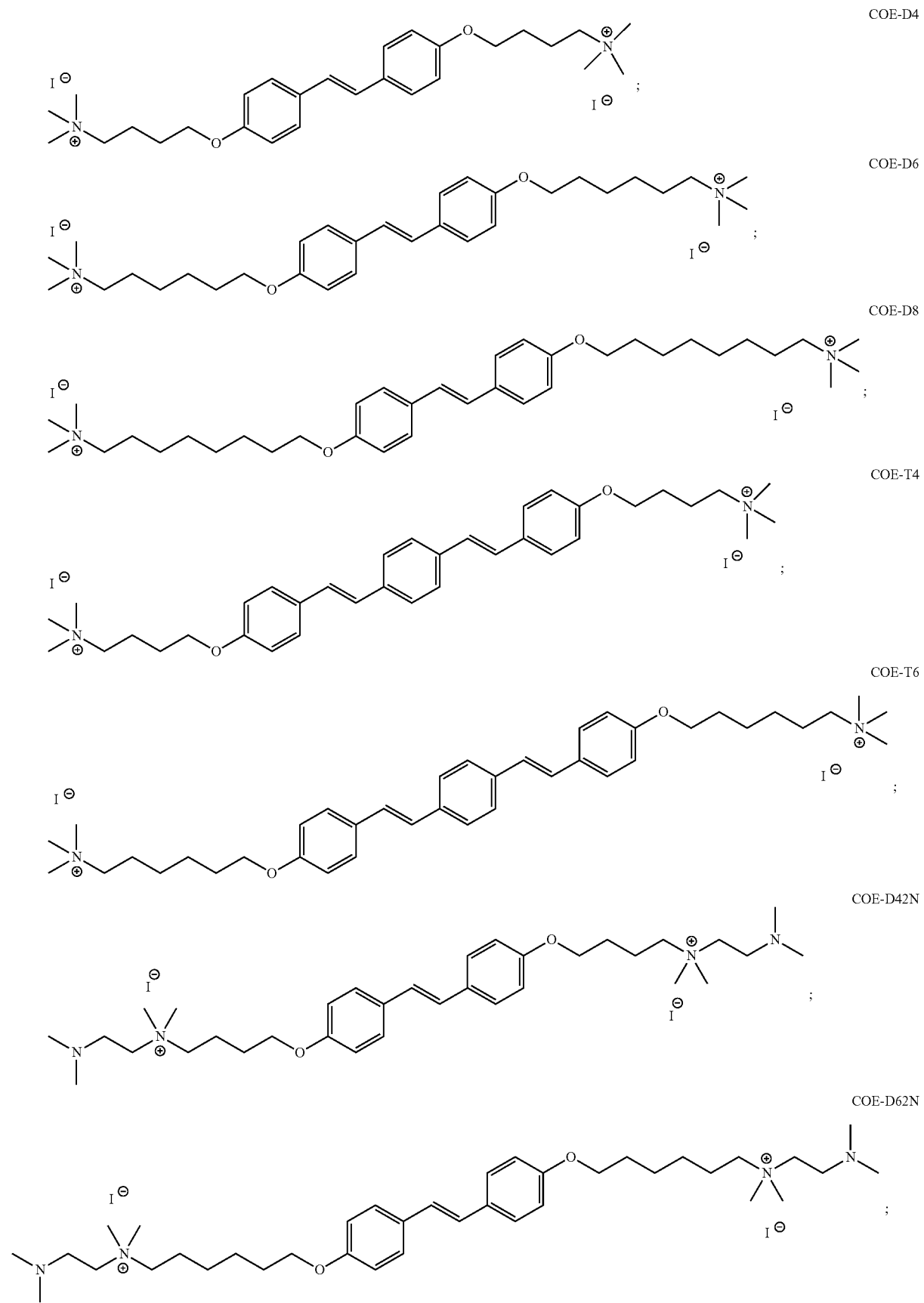

-continued
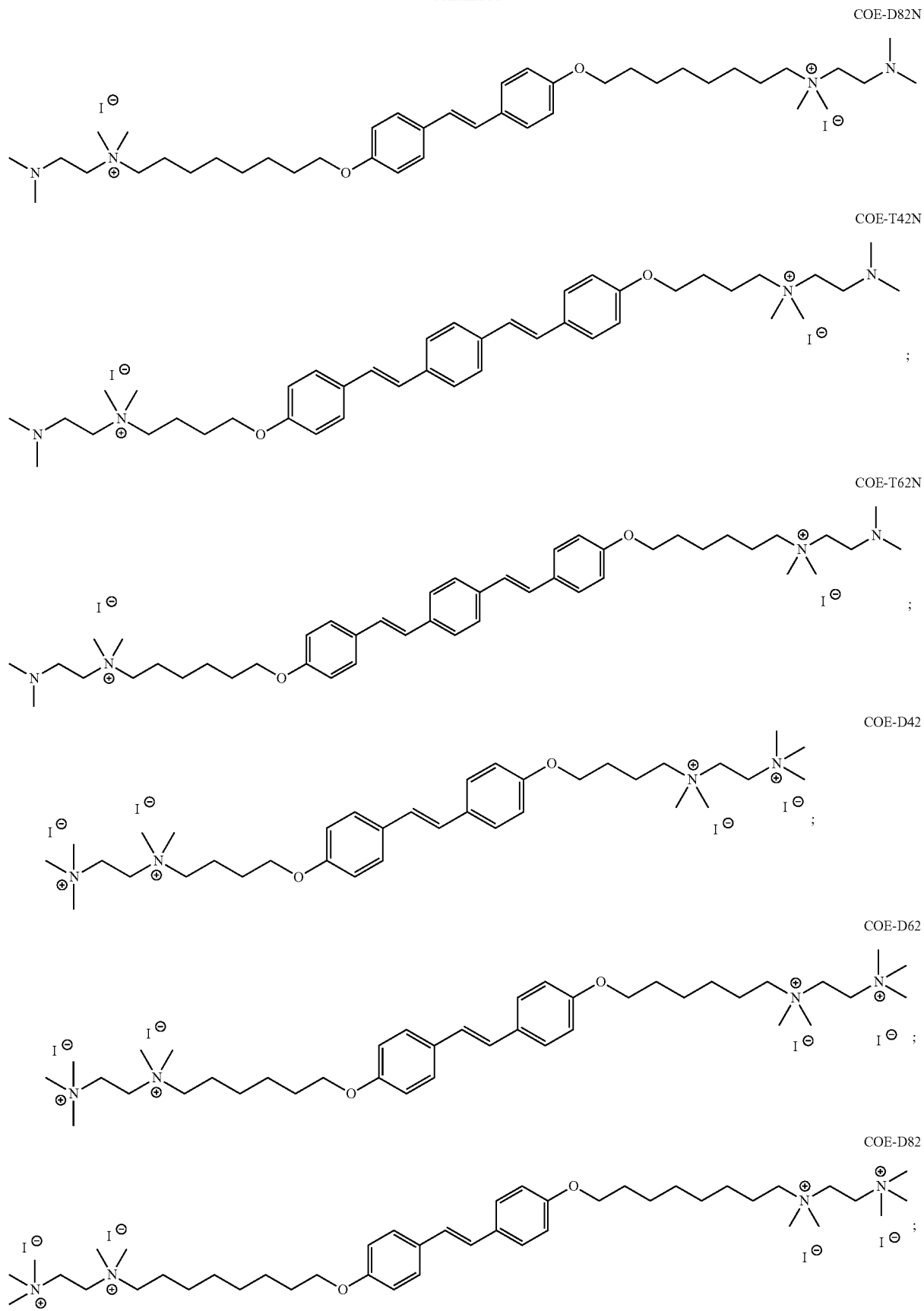

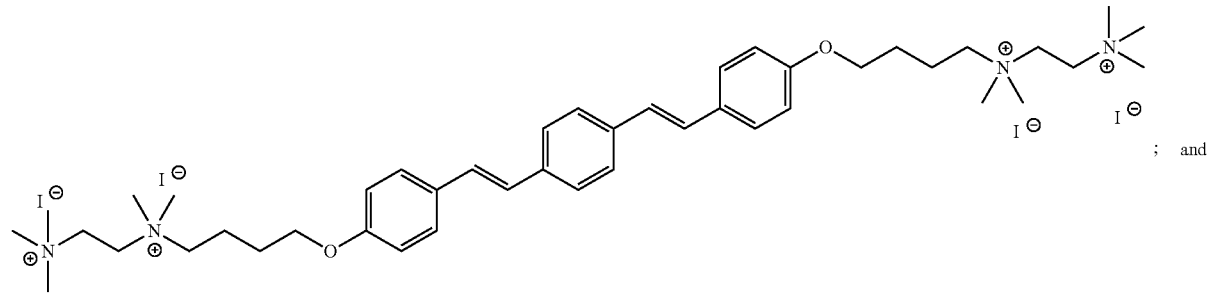
COE-T42
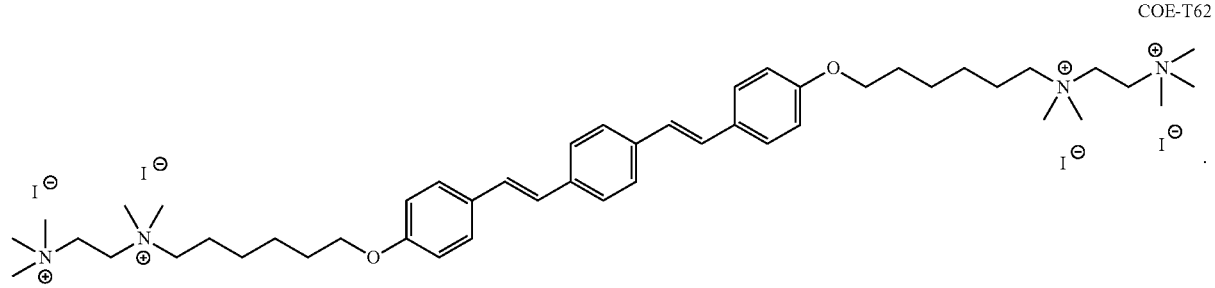
COE-T62
Embodiments of the invention that may be mentioned include those in which the compound of formula I is a compound selected from the list:
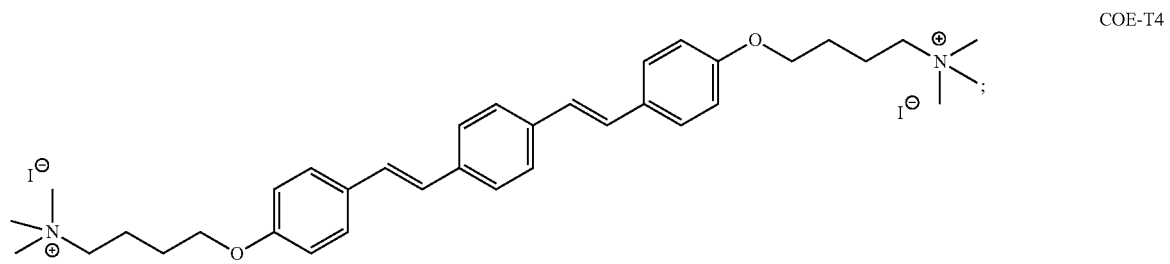
COE-T4
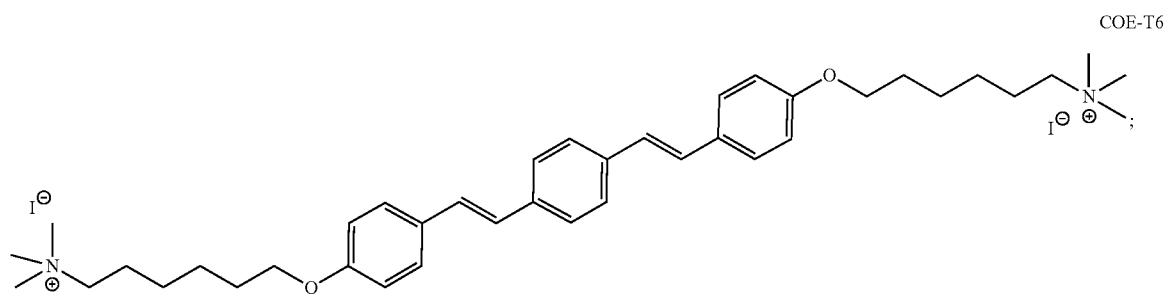
COE-T6
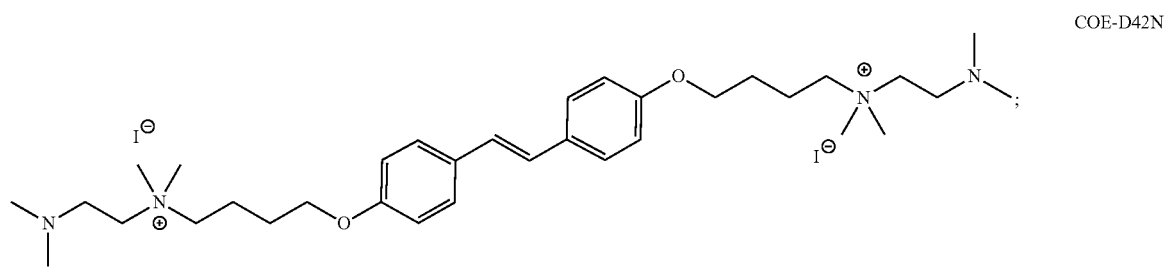
COE-D42N -continued
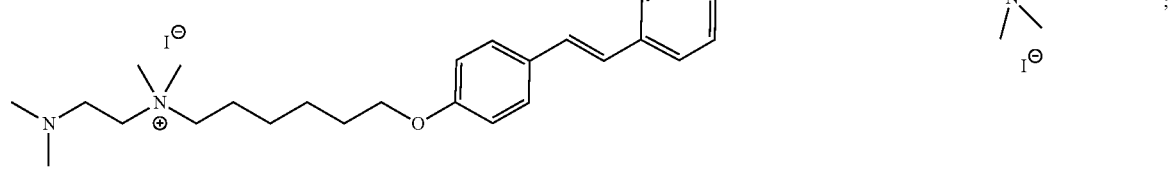
COE-D62N
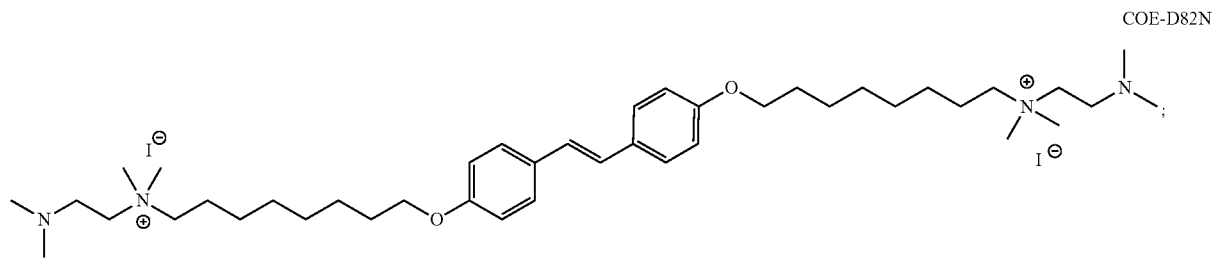
COE-D82N
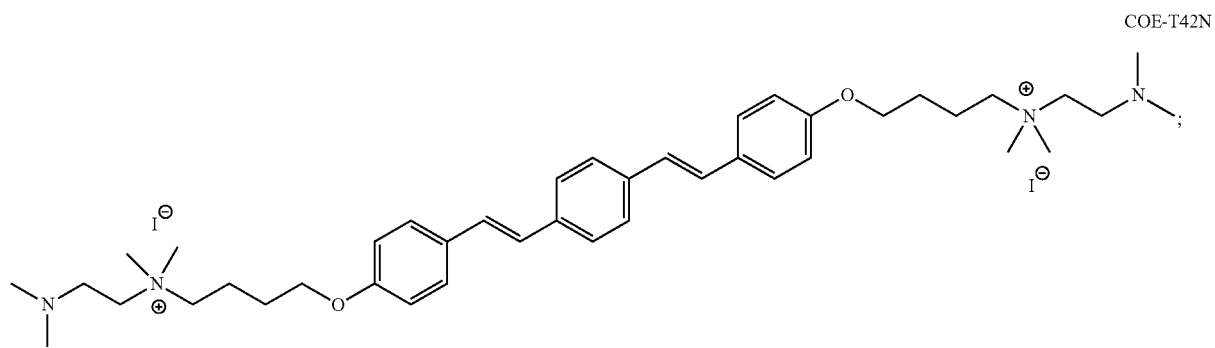
COE-T42N
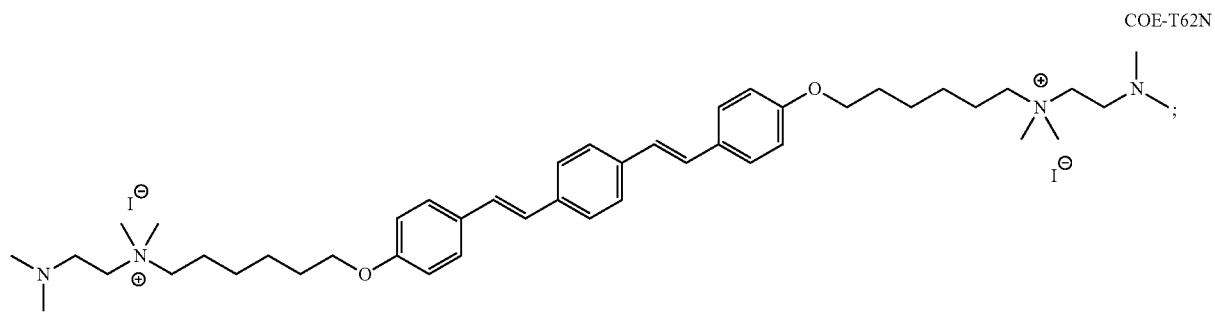
COE-T62N
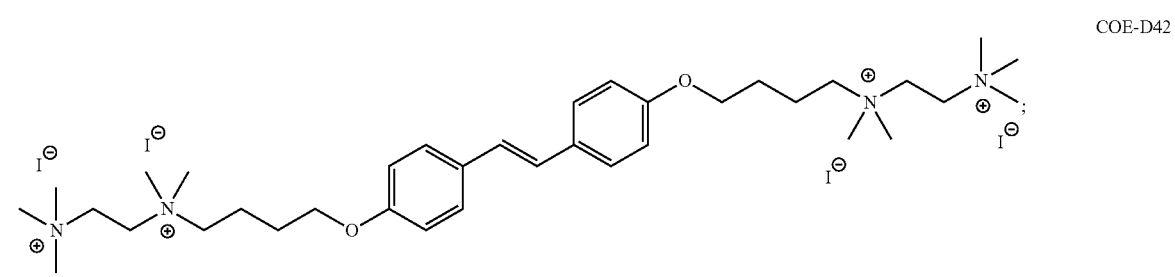
COE-D42

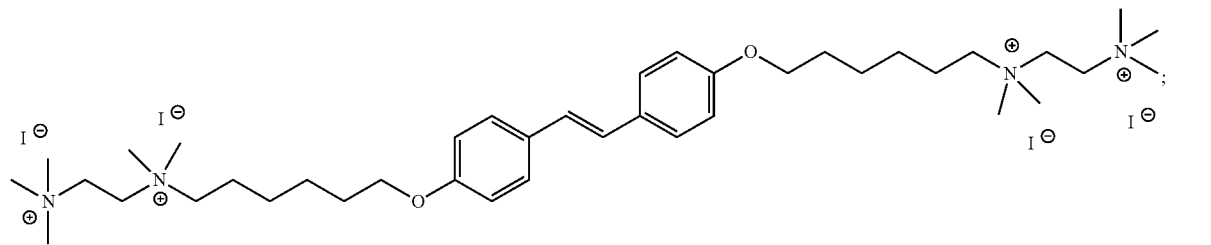
COE-D62
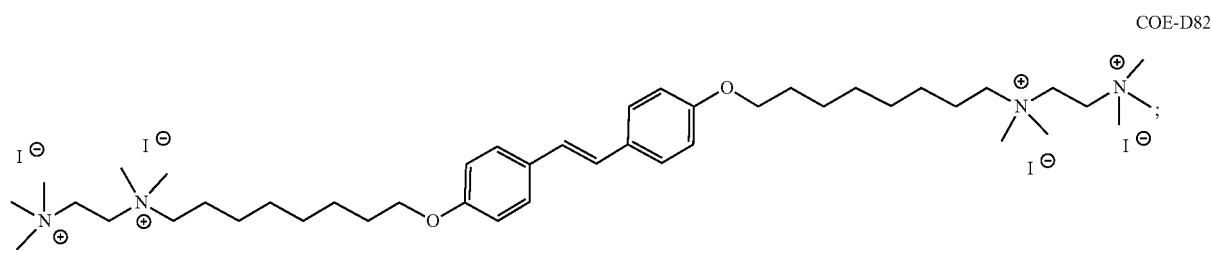
COE-D82
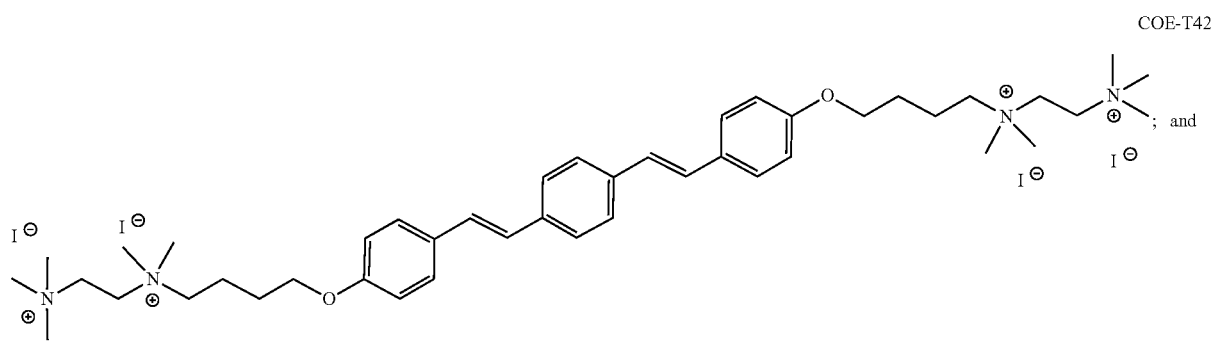
COE-T42
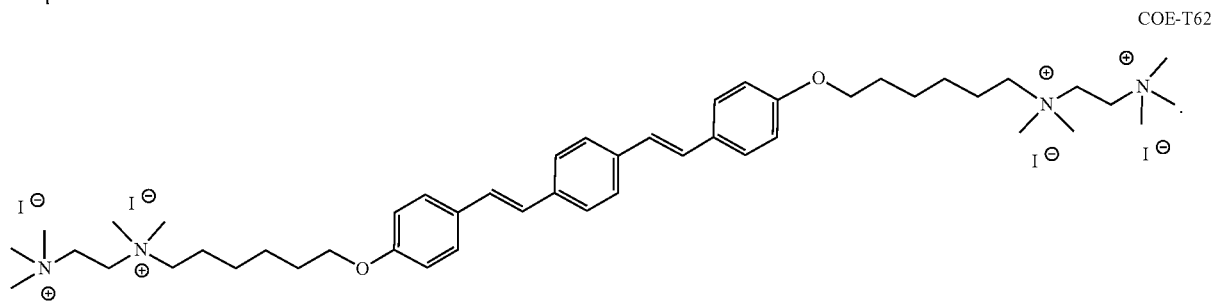
COE-T62
In yet further embodiments of the invention that may be mentioned include those in which the compound of formula I is a compound selected from the list:
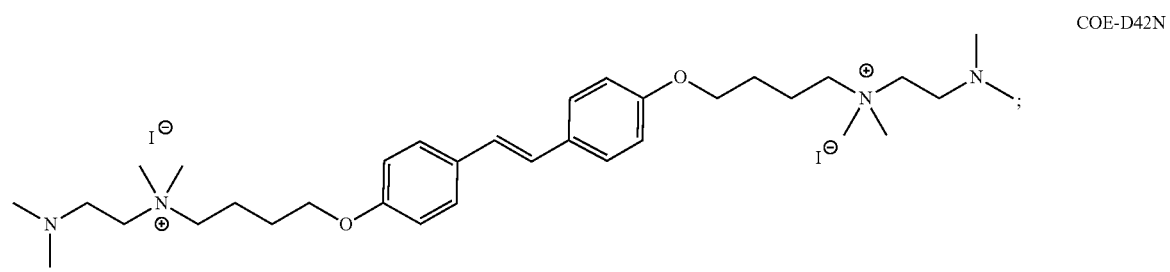
COE-D42N -continued
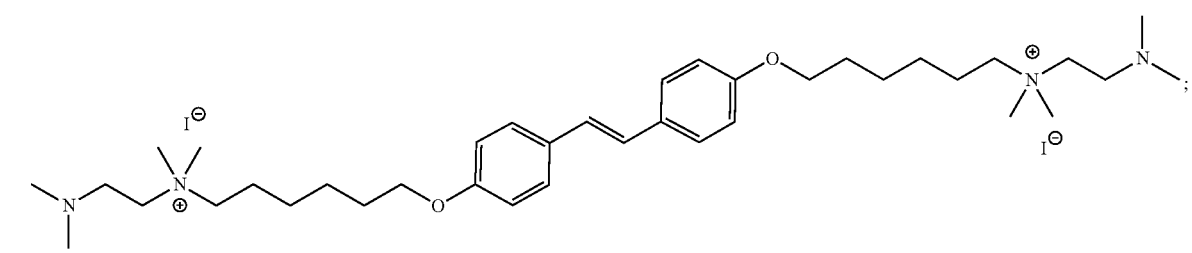
COE-D62N
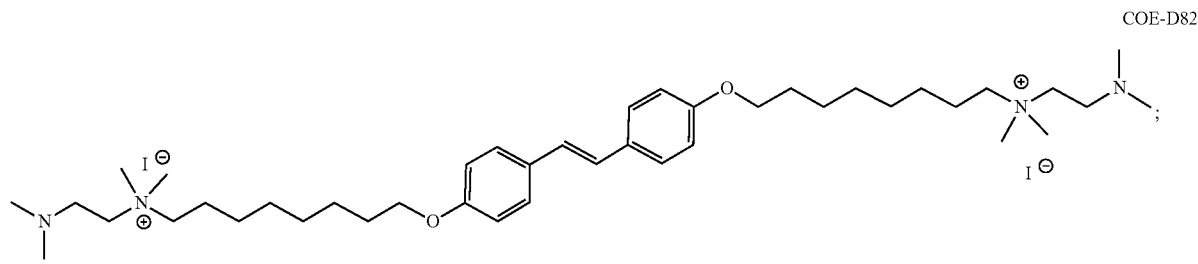
COE-D82N
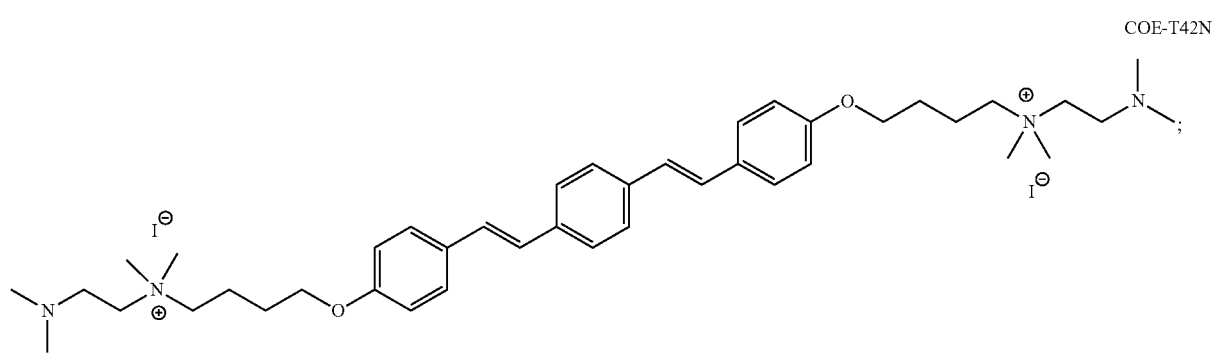
COE-T42N
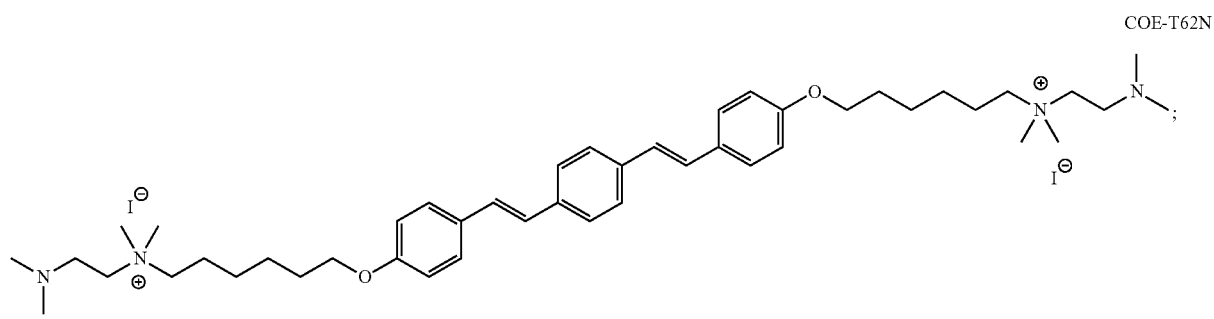
COE-T62N
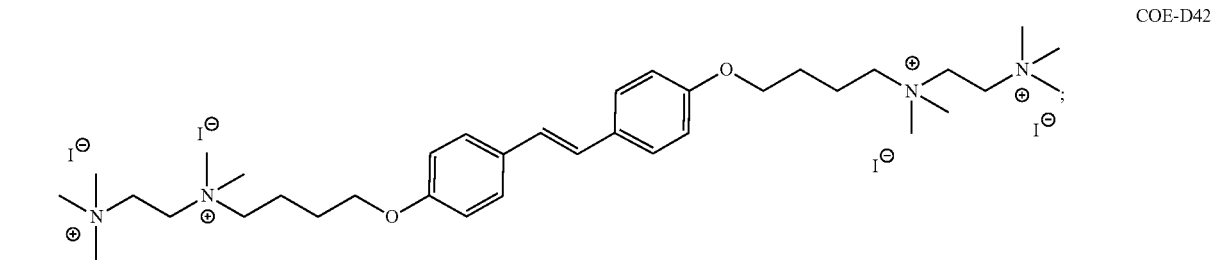
COE-D42

-continued
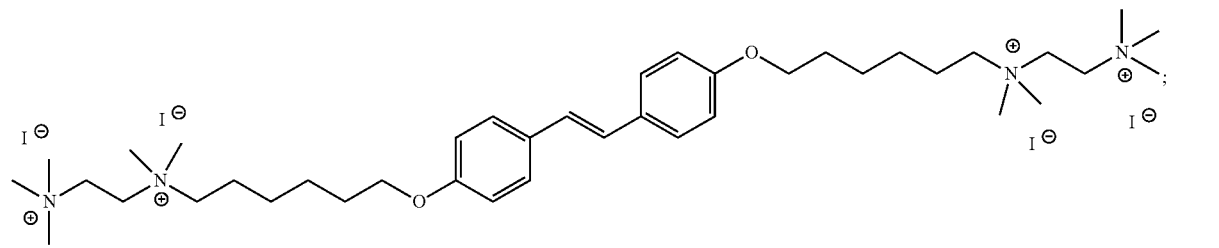
COE-D62
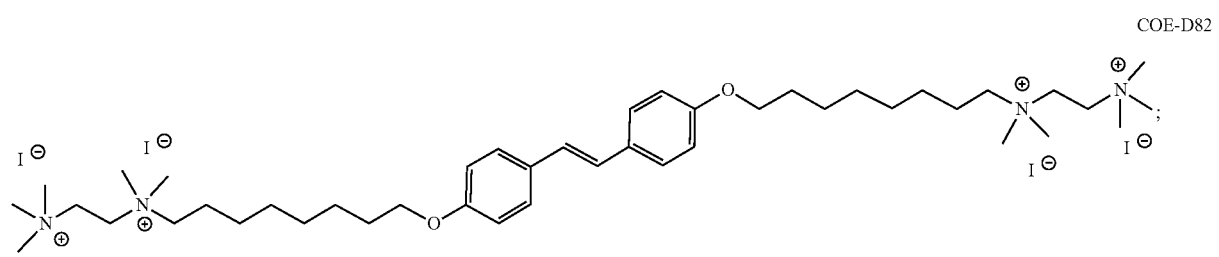
COE-D82
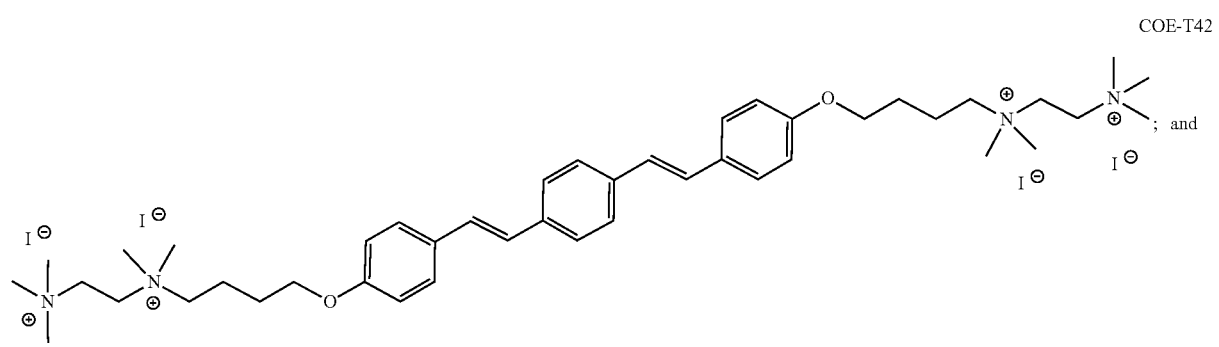
COE-T42
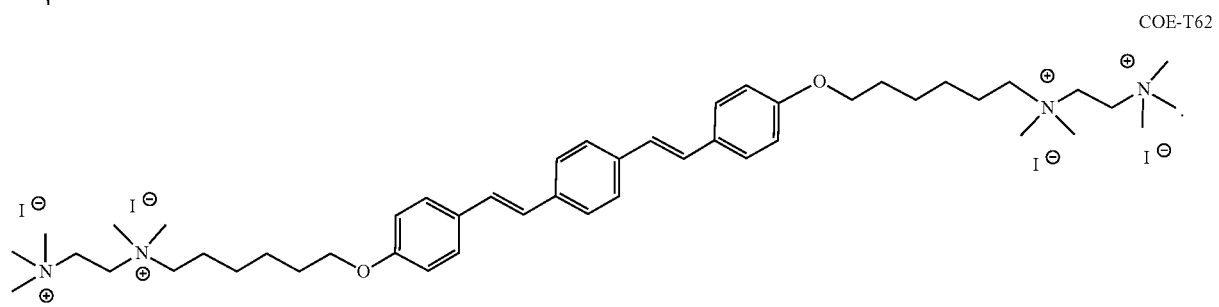
COE-T62
For example, the compound of formula I may be selected from the group consisting of:
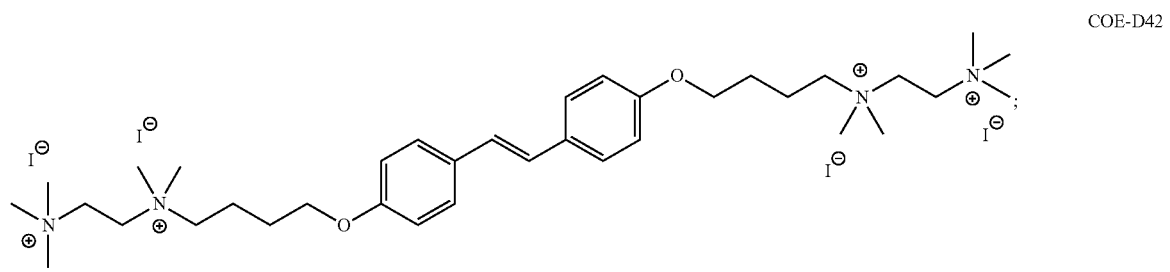
COE-D42

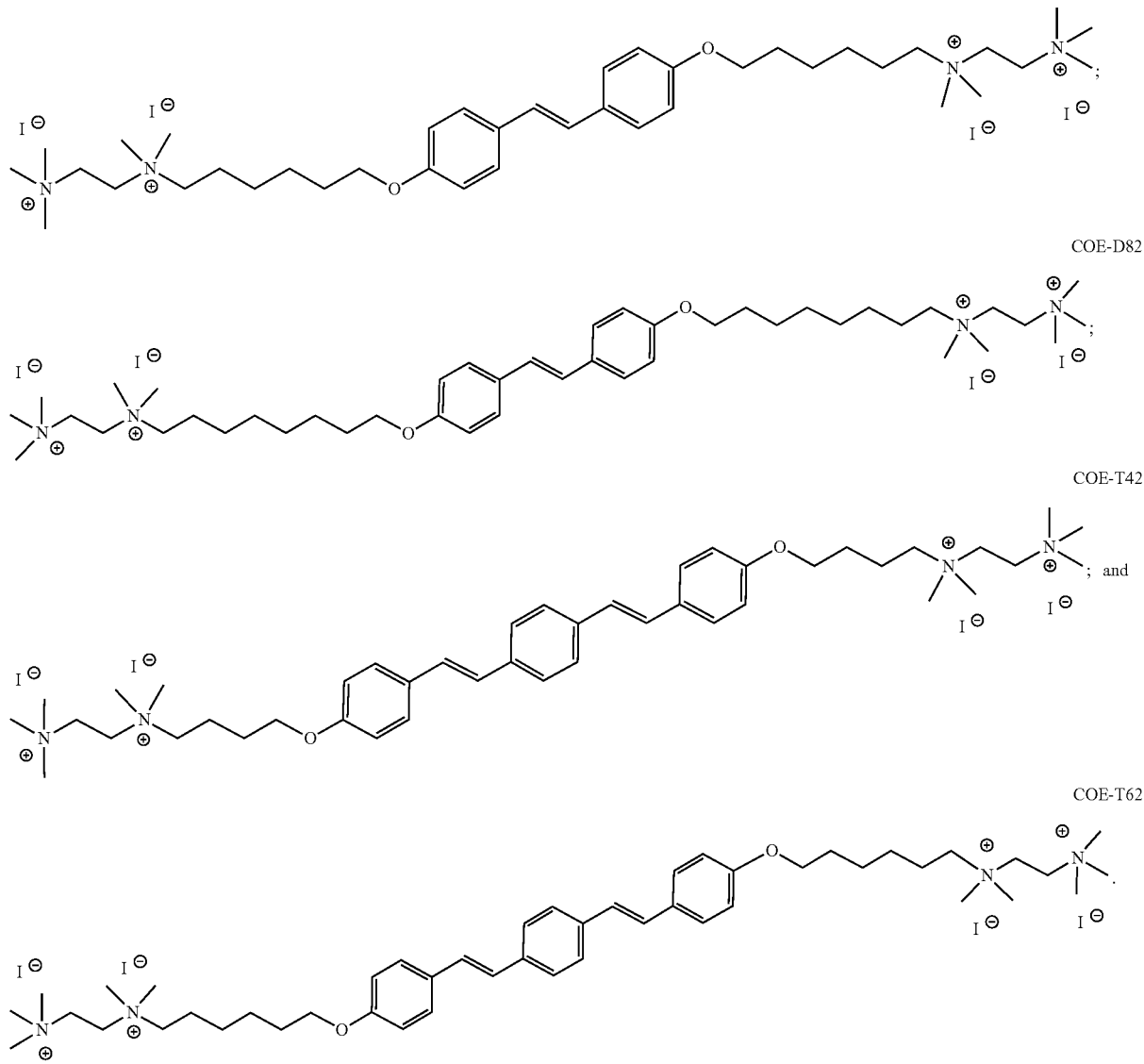

The specific compounds of formula I provided above are illustrated showing iodide as the counterion. It will be appreciated that the counterion may be selected from any suitable form of X⁻, such as chloride, bromide and fluoride, as well as iodide. However, in embodiments of the invention that may be mentioned herein iodide may be a preferred counterion.

For the avoidance of doubt, references herein to compounds of formula I include, where the context permits, references to any of compounds of formula I and Ia. Further, references to any of the compounds of formula I or Ia includes references to such compounds per se, to tautomers of such compounds, as well as to pharmaceutically acceptable salts or solvates, or pharmaceutically functional derivatives of such compounds.

Further embodiments of the invention that may be mentioned include those in which the compound of formula I is isotopically labelled. However, other, particular embodiments of the invention that may be mentioned include those in which the compound of formula I is not isotopically labelled.

The term "isotopically labelled", when used herein includes references to compounds of formula I in which there is a non-natural isotope (or a non-natural distribution of isotopes) at one or more positions in the compound. References herein to "one or more positions in the compound" will be understood by those skilled in the art to refer to one or more of the atoms of the compound of formula I. Thus, the term "isotopically labelled" includes references to compounds of formula I that are isotopically enriched at one or more positions in the compound.

The isotopic labelling or enrichment of the compound of formula I may be with a radioactive or non-radioactive isotope of any of hydrogen, carbon, nitrogen, oxygen, sulfur, fluorine, chlorine, bromine and/or iodine. Particular isotopes that may be mentioned in this respect include $^{2}H$, $^{3}H$, $^{11}C$, $^{13}C$, $^{14}C$, $^{13}N$, $^{15}N$, $^{15}O$, $^{17}O$, $^{18}O$, $^{35}S$, $^{18}F$, $^{37}Cl$, $^{77}Br$, $^{82}Br$ and $^{125}I$) When the compound of formula I is labelled or enriched with a radioactive or nonradioactive isotope, compounds of formula I that may be mentioned include those in which at least one atom in the compound displays an isotopic distribution in which a radioactive or non-radioactive isotope of the atom in question is present in levels at least 10% (e.g. from 10% to 5000%, particularly from 50% to 1000% and more particularly from 100% to 500%) above the natural level of that radioactive or non-radioactive isotope.

The compounds of formula I may be used in medicine. When used in medicine, the compounds of formula I may be provided as a pharmaceutical formulation comprising a compound of formula I as defined above and one or more of a pharmaceutically acceptable adjuvant, diluent or carrier.

The compound of formula I in the above-mentioned aspect of the invention may be utilised in a method of medical treatment. Thus, according to further aspects of the invention, there is provided:
(a) a compound of formula I for use in medicine;
(b) a compound of formula I for use in the treatment or prevention of an infection;
(c) use of a compound of formula I for the preparation of a medicament for the treatment of an infection; and
(d) a method of treatment of an infection, which method comprises the administration of an effective amount of a compound of formula I.

In the above-mentioned treatments, any compound of formula I discussed hereinbefore may be used. Particular compounds of formula I that may be mentioned in such treatment embodiments include, but are not limited to:

infectious cause through common knowledge. In other words, when there is one or more minor symptoms related to a subclinical infection, this may be sufficient for one to know that there is an infectious agent that requires treatment, without the need for identification of the exact infectious agent or a professional diagnosis.

As referred to herein, the term "microbial" refers to a microscopic organism comprising either a single cell or clusters of cells and encompasses, but is not limited to, prokaryotes such as bacteria and archaea; and forms of eukaryotes such as protozoan, fungi, algae. In particular embodiments that may be mentioned herein, the term "microbial" refers to prokaryotes and eukaryotes. The prokaryotes may refer to bacteria, such as *Staphylococcus* spp, *Streptococcus* spp, *Bacillus* spp, *Enterococcus* spp, *Listeria* spp, *Mycoplasma* spp, and includes aerobic, and anaerobic bacteria. The term "microbial" may refer to an antibiotic-sensitive strains or an antibiotic-resistant strains. In a preferred embodiment, the term may refer to MRSA. In another preferred embodiment, the term may refer to MRSP. And in another preferred embodiment includes all of the ESKAPE pathogens.

Examples of specific microbial species that may be referred to herein include, but are not limited to:
coagulase-negative staphylococci (CNS) (e.g. *Staphylococcus epidermidis. Staphylococcus simulans, Staphylococcus felis, Staphylococcus xylosus, Staphylococcus chromogenes, Staphylococcus warneri, Staphylococcus haemolyticus, Staphylococcus sciuri, Staphylococcus saprophyticus, Staphylococcus hominis, Staphylococcus caprae, Staphylococcus cohnii* subsp. *Cohnii,*

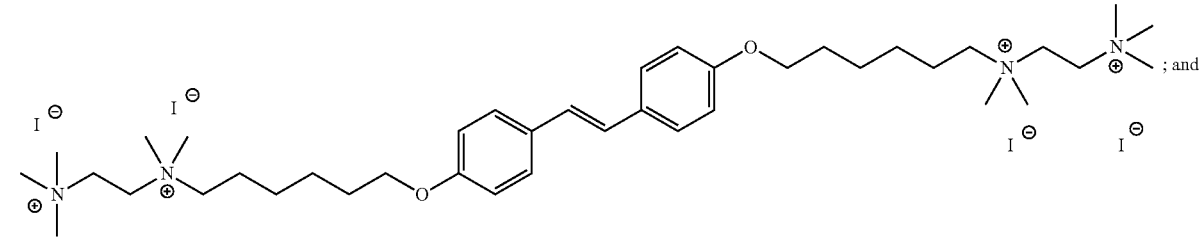

COE-D62

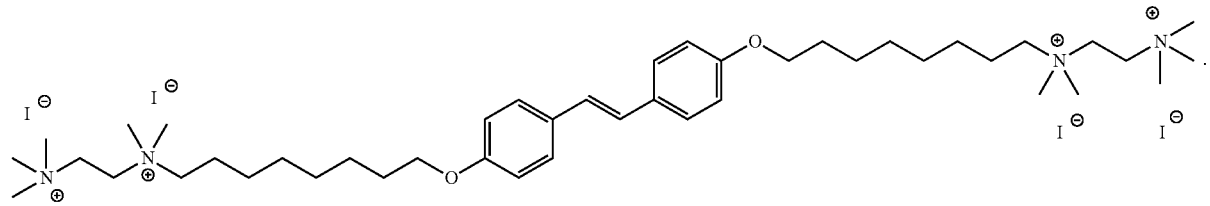

COE-D82

The term "an infection" when used herein may refer to a microbial or viral infection. The infection may present itself as a clinical infection (i.e. with obvious symptoms) or as a subclinical infection (i.e. is nearly or completely asymptomatic or when Koch's postulates are not satisfied), such that the presence of the infection may require determination by laboratory testing (e.g. microbial culture or DNA techniques such as polymerase chain reaction testing). In cases where the subclinical infection presents some symptoms (e.g. acne or dandruff), it may be assumed that there is an underlying

*Staphylococcus cohnii* subsp. *urealyticus, Staphylococcus capitis* subsp. *capitis, Staphylococcus capitis* subsp. *urealyticus, Staphylococcus hyicus*);
coagulase-positive staphylococci (e.g. *Staphylococcus aureus, Staphylococcus pseudintermedius, Staphylococcus delphini, Staphylococcus schleiferi* subsp. *Coagulans*, and *Staphylococcus aureus* subsp. *Anaerobius*);
a *Streptococcus* bacteria (e.g. *Streptococcus uberis, Streptococcus agalactiae, Streptococcus dysgalactiae,*

*Streptococcus pyogenes, Streptococcus bovis, Streptococcus equi* subsp. *Zooepidemicus*, and *Streptococcus equinus*);

a *Bacillus* bacteria (e.g. *Bacillus melaninogenicus, Bacillus pumilus, Bacillus licheniformis, Bacillus cereus, Bacillus subtilis*, and *Bacillus anthracis*);

an *Enterococcus* bacteria (e.g. *Enterococcus faecium, Enterococcus faecalis*, and *Enterococcus durans*);

a *Listeria* bacteria (e.g. *Listeria monocytogenes*);

an anaerobic bacteria (e.g. *Clostridium perfringens, Actinomyces bovis, Propionibacterium acnes, Propionibacterium granulosum, Eubacterium, Peptococcus indolicus*, and *Peptostreptococcus anaerobius*);

a *Mycoplasma* bacteria (e.g. *Mycoplasma bovis*);

a fungi of the *Malassezia* genus.

The compounds of formula I may be particularly effective against one or more of ESKAPE pathogens (Enterobacteriaceca including *E. coli, S. aureus, P. aeruginosa, Acinetobacter baumanii, Kleibsiella pneumoniae*). Such ESKAPE pathogens may include those formally designated ESKAPE pathogens and closely related species such as uropathogenic strain of *E. coli* (UTI89), a clinically-derived *E. faecalis* strain (OG1RF) and drug resistant strains of *S. aureus* (MRSA BAA-40). The compounds of formula I have also been shown to have activity against a range of gram positive and gram negative bacteria including those on the WHO priority pathogens list.

Examples of viral agents that may cause a viral infection herein include, but are not limited to, enveloped viruses that express host derived phospholipids. Specific examples that may be mentioned herein include, but are not limited to DNA viruses such as, herpesviruses, poxviruses, hepadnaviruses and RNA viruses (e.g. flavivirus, togavirus, coronavirus, hepatitis D, orthomyxovirus, paramyxovirus, rhabdovirus, bunyavirus, filovirus, and retroviruses, such as lentivirus).

In preferred embodiments of the invention, the compounds of formula I may be antimicrobial agents.

As will be appreciated, many microbial infections may be prolonged or exacerbated by the formation of biofilms. A biofilm is an aggregate of microorganisms in which bacterial cells are closely associated with other biofilm members and/or to a surface. The adherent cells found in biofilm are frequently embedded within a microbially-produced matrix of an extracellular polymeric material, which can form on living or non-living surfaces, and represent a prevalent mode of microbial life in natural, industrial and hospital settings. Biofilms form in response to many factors, which may include cellular recognition of specific or non-specific attachment sites on a surface, nutritional cues, community driven signaling, or in some cases, by exposure of planktonic cells to sub-inhibitory concentrations of antibiotics. Bacteria cells in a planktonic state (individual cells) may form into a biofilm if left untreated and individual members of a biofilm may disperse from the biofilm into a planktonic phase and may later exist in a different biofilm.

Biofilms and planktonic cells are known to be involved in a wide variety of microbial infections in the body. Infectious processes in which biofilms have been implicated include common problems such as urinary tract infections, catheter infections, middle-ear infections, formation of dental plaque, gingivitis, coating contact lenses, endocarditis, and infections in the cystic fibrosis lung. Biofilms can also be formed on the inert surfaces of implanted devices such as catheters, prosthetic cardiac valves, bone replacement prostheses, and intrauterine devices. Bacterial biofilms may also impair cutaneous wound healing and reduce topical antibacterial efficiency in healing or treating infected skin wounds.

As will be appreciated, many bacteria can form biofilms. For example, *Pseudomonas aeruginosa* is known to form biofilms and is an important opportunistic pathogen and causative agent of emerging nosocomial infections and in cystic fibrosis lung infections. Dental plaque is a biofilm on the surface of the teeth and consists of bacterial cells (mainly *Streptococcus mutans* and *Streptococcus sanguis*), salivary polymers and bacterial extracellular products. *Legionella* bacteria are known to grow under certain conditions in biofilms, in which they are protected against disinfectants. *Neisseria gonorrhoeae* is an exclusive human pathogen that has been demonstrated to form biofilms on glass surfaces and over human cells. Other types of bacteria that form biofilms include *Staphylococcus aureus* and *Enterococcus* sp.

Because of the properties provided by microorganisms in a biofilm, biofilms are typically less susceptible to antibiotics, antimicrobials, and biocides. In some cases, bacteria in a biofilm can be up to 4,000 times more resistant (i.e., less susceptible) than the same organism in a planktonic state to antimicrobial chemotherapy. Minimum inhibitory concentration (MIC) describes the amount of an active agent delivered to planktonic microorganisms necessary to inhibit biofilm formation. In contrast, minimum biofilm eradication concentration (MBEC) describes the minimum concentration of an active agent delivered to a biofilm necessary to inhibit or eradicate biofilm growth. The differential that can be seen in these amounts illustrates that biofilm-forming microorganisms are much less susceptible to antimicrobial agents at standard therapeutic concentrations.

It has been surprisingly found that the compounds of formula I disclosed herein are active against not only planktonically growing microbes, but also microbes that are essentially encased within a biofilm. Therefore, reference to the treatment of microbial infections in the current application is also explicitly intended to cover the treatment of microbial infections involving biofilms in a subject in need of treatment thereof.

Compounds of formula I may be administered by any suitable route, but may particularly be administered orally, intravenously, intramuscularly, cutaneously, subcutaneously, transmucosally (e.g. sublingually or buccally), rectally, transdermally, nasally, pulmonarily (e.g. tracheally or bronchially), topically, by any other parenteral route, in the form of a pharmaceutical preparation comprising the compound in a pharmaceutically acceptable dosage form. Particular modes of administration that may be mentioned include oral, intravenous, cutaneous, subcutaneous, nasal, intramuscular or intraperitoneal administration.

Compounds of formula I will generally be administered as a pharmaceutical formulation in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use.

Suitable pharmaceutical formulations may be found in, for example, Remington *The Science and Practice of Pharmacy,* 19th ed., Mack Printing Company, Easton, Pennsylvania (1995). For parenteral administration, a parenterally acceptable aqueous solution may be employed, which is pyrogen free and has requisite pH, isotonicity, and stability. Suitable solutions will be well known to the skilled person, with numerous methods being described in the literature. A brief review of methods of drug delivery may also be found in e.g. Langer, Science (1990) 249, 1527.

Otherwise, the preparation of suitable formulations may be achieved routinely by the skilled person using routine techniques and/or in accordance with standard and/or accepted pharmaceutical practice.

The amount of compound of formula I in any pharmaceutical formulation used in accordance with the present invention will depend on various factors, such as the severity of the condition to be treated, the particular patient to be treated, as well as the compound(s) which is/are employed. In any event, the amount of compound of formula I in the formulation may be determined routinely by the skilled person.

For example, a solid oral composition such as a tablet or capsule may contain from 1 to 99% (w/w) active ingredient; from 0 to 99% (w/w) diluent or filler; from 0 to 20% (w/w) of a disintegrant; from 0 to 5% (w/w) of a lubricant; from 0 to 5% (w/w) of a flow aid; from 0 to 50% (w/w) of a granulating agent or binder; from 0 to 5% (w/w) of an antioxidant; and from 0 to 5% (w/w) of a pigment. A controlled release tablet may in addition contain from 0 to 90% (w/w) of a release-controlling polymer.

A parenteral formulation (such as a solution or suspension for injection or a solution for infusion) may contain from 1 to 50% (w/w) active ingredient; and from 50% (w/w) to 99% (w/w) of a liquid or semisolid carrier or vehicle (e.g. a solvent such as water); and 0-20% (w/w) of one or more other excipients such as buffering agents, antioxidants, suspension stabilisers, tonicity adjusting agents and preservatives.

Depending on the disorder, and the patient, to be treated, as well as the route of administration, compounds of formula I may be administered at varying therapeutically effective doses to a patient in need thereof.

However, the dose administered to a mammal, particularly a human, in the context of the present invention should be sufficient to affect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a compound of formula I.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

The aspects of the invention described herein (e.g. the above-mentioned compounds, combinations, methods and uses) may have the advantage that, in the treatment of the conditions described herein, they may be more convenient for the physician and/or patient than, be more efficacious than, be less toxic than, have better selectivity over, have a broader range of activity than, be more potent than, produce fewer side effects than, or may have other useful pharmacological properties over, similar compounds, combinations, methods (treatments) or uses known in the prior art for use in the treatment of those conditions or otherwise.

For example, the compounds of formula I are surprisingly less toxic to mammalian cells than would have been expected, based upon other COE compounds as shown in Example 7. At the same time, such compounds have excellent antimicrobial efficacy towards a wide spectrum of microorganisms (as shown in Example 3), and are able to eradicate microorganisms more rapidly than conventional antibiotics and the microorganisms have little or no tendency to develop resistance against such compounds (as shown in Example 6).

Other compounds of formula I may be prepared in accordance with techniques that are well known to those skilled in the art, for example as described hereinafter in the examples section.

Substituents, such as $R^2$ in final compounds of formula I (or precursors thereto and other relevant intermediates) may be modified one or more times, after or during the processes described hereinafter by way of methods that are well known to those skilled in the art. Examples of such methods include substitutions, reductions (e.g. carbonyl bond reductions in the presence of suitable and, if necessary, chemoselective, reducing agents such as $LiBH_4$ or $NaBH_4$), oxidations, alkylations, acylations, hydrolyses, esterifications, and etherifications. The precursor groups can be changed to a different such group, or to the groups defined in formula I, at any time during the reaction sequence.

Compounds of the invention may be isolated from their reaction mixtures using conventional techniques (e.g. recrystallisation, column chromatography, preparative HPLC, etc.).

In the processes described hereinafter, the functional groups of intermediate compounds may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described hereinafter may be converted chemically to unprotected compounds using standard deprotection techniques.

The type of chemistry involved will dictate the need, and type, of protecting groups as well as the sequence for accomplishing the synthesis.

The use of protecting groups is fully described in "Protective Groups in Organic Chemistry", edited by J W F McOmie, Plenum Press (1973), and "Protective Groups in Organic Synthesis", $3^{rd}$ edition, T. W. Greene & P. G. M. Wutz, Wiley-Interscience (1999).

As used herein, the term "functional groups" means, in the case of unprotected functional groups, hydroxy-, thiolo-, amino function, carboxylic acid and, in the case of protected functional groups, lower alkoxy, N-, O-, S-acetyl, carboxylic acid ester.

Compounds of formula I may be useful in the removal of biofilms from any surface in need thereof. Thus, there is also disclosed herein a method of removing a biofilm from a solid substrate or preventing build-up of a biofilm on a solid substrate, or killing, inhibiting, or dispersing microbes inhabiting said biofilm in a system susceptible to biofilm formation, said biofilm being formed by at least one microorganism, the method comprising the step of contacting the system with an effective amount of a compound of formula I or a solvate thereof as defined above or a composition comprising a compound of formula I to remove the biofilm or prevent its formation.

The method directly above is explicitly intended to relate to ex-vivo uses. Such uses include, but are not limited to controlling the formation of biofilms on surfaces that may suffer corrosion, on membranes used for water treatment (e.g. reverse osmosis water membranes), and on the surfaces of medical devices where biofilms may form and which need to be removed in order to enable said devices to be sterilised effectively for initial use and for re-use.

The compounds of formula I may also be used in a variety of other applications. These include:
- (BA) as an additive for use in industrial processes, for example in oil and gas production to protect infrastructure and products from the negative consequences of microbial activity (e.g. corrosion or oil souring);
- (BB) as an additive to industrial products (such as petroleum distillates) to protect the product and the associated infrastructure (e.g. fuel tanks) from the consequences noted in (BA);
- (BC) as an additive added to: paints and other coatings; and polymeric blends. The resulting products may include antimicrobial films (such as in food packaging), fittings (such as pipe fittings used on neonatal incubators) and textiles (e.g. textiles to prevent odour such as in shoes or motorbike helmets), as well as medical devices made from polymeric materials that incorporate the additive (e.g. antimicrobial catheters and contact lenses).

When used as an additive, the compound of formula I may be supplied alone or provided as a formulation in combination with a suitable adjuvant, diluent or carrier. For the avoidance of doubt, the invention also relates to the resulting products obtained when the compound of formula I is used as an additive. When used as an additive, the amount of the compound of formula I in the resulting product or formulation may be from 0.00001 wt % to 99 wt % of the product or formulation, such as from 0.0001 wt % to 10 wt %.

The compounds of formula I may also be used for cosmetic or cleansing purposes. Therefore, there is also disclosed herein a cosmetic or cleansing formulation, comprising a compound of formula I as defined above and one or more of an adjuvant, diluent or carrier suitable for use in a cosmetic or cleansing formulation.

When used for cosmetic purposes, the compounds of formula I may be used to remove microbes so as to prevent dandruff, acne (or at least sebaceous spots) and gingivitis. When used to form a cleansing composition, the compound of formula I may aid in the sterilisation of a surface in need thereof (e.g. from microbes in the planktonic state or as a biofilm).

Given the above, the compounds of formula I may be used as antimicrobial active ingredients in personal care preparations, for example shampoos, bath additives, hair-care products, liquid and solid soaps (based on synthetic surfactants and salts of saturated and/or unsaturated fatty acids), lotions and creams and other aqueous or alcoholic solutions, e.g. cleansing solutions for the skin.

Thus, there is also provided an antimicrobial and/or antifungal detergent composition comprising a polymer or copolymer of the invention and a surfactant. It will be appreciated that the composition may also contain additional cosmetically tolerable carriers and/or adjuvants. Said composition may in particular be in the form of a shampoo or in the form of a solid or liquid soap, though other compositions as described hereinabove are also contemplated (e.g. other hair-care products, lotions and creams etc.).

The detergent composition may comprise from 0.01 to 15% by weight, such as from 0.5 to 10% by weight of a polymer or copolymer of the invention. It will be appreciated that more than one polymer and copolymer of the invention may form part of the detergent composition.

Depending upon the form of the detergent composition, it will comprise, in addition to the polymer or copolymer of the invention, further constituents, for example sequestering agents, colourings, perfume oils, thickening or solidifying (consistency regulator) agents, emollients, UV absorbers, skin-protective agents, antioxidants, additives that improve mechanical properties, such as dicarboxylic acids and/or Al, Zn, Ca and Mg salts of $C_{14}$-$C_{22}$ fatty acids, and optionally, preservatives.

The detergent composition may be formulated as a water-in-oil or oil-in-water emulsion, as an alcoholic or alcohol-containing formulation, as a vesicular dispersion of an ionic or non-ionic amphiphilic lipid, as a gel, a solid stick or as an aerosol formulation.

As a water-in-oil or oil-in-water emulsion, the detergent composition may comprise from 5 to 50 wt % of an oily phase, from 5 to 20 wt % of an emulsifier and from 30 to 90 wt % water. The oily phase may contain any oil suitable for cosmetic formulations, e.g. one or more hydrocarbon oils, a wax, a natural oil, a silicone oil, a fatty acid ester or a fatty alcohol.

Preferred mono- or poly-ols are ethanol, isopropanol, propylene glycol, hexylene glycol, glycerol and sorbitol.

Detergent compositions may be provided in a wide variety of preparations. Examples of suitable compositions include, but are not limited to skin-care preparations (e.g. skin-washing and cleansing preparations in the form of tablet-form or liquid soaps, soapless detergents or washing pastes), bath preparations, (e.g. liquid compositions such as foam baths, milks, shower preparations or solid bath preparations), shaving preparations (e.g. shaving soap, foaming shaving creams, non-foaming shaving creams, foams and gels, preshave preparations for dry shaving, aftershaves or after-shave lotions), cosmetic hair-treatment preparations (e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, hair-waving preparations for permanent waves (hot wave, mild wave, cold wave), hair-straightening preparations, liquid hair-setting preparations, foams, hairsprays, bleaching preparations; e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile).

An antimicrobial soap may have, for example, the following composition:
- 0.01 to 5% by weight of a compound of formula I;
- 0.3 to 1% by weight titanium dioxide;
- 1 to 10% by weight stearic acid; and
- the remainder being a soap base, e.g. the sodium salts of tallow fatty acid and coconut fatty acid or glycerol.

A shampoo may have, for example, the following composition:
- 0.01 to 5% by weight of a compound of formula I;
- 12.0% by weight sodium laureth-2-sulfate;
- 4.0% by weight cocamidopropyl betaine;
- 3.0% by weight NaCl; and
- water to 100 wt %.

As will be appreciated, the pharmaceutically acceptable compositions disclosed herein may also be suitable for use as encouraging growth promotion in intensive farming. Use in this field is also specifically contemplated. Such formulations may be similar to those described above for medicinal uses.

Non-limiting examples which embody certain aspects of the invention will now be described.

EXAMPLES

Materials and Instruments p-Hydroxybenzaldehyde, titanium tetrachloride, zine power, anhydrous tetrahydrofuran (THF), trimethylamine solution in methanol, 1,4-diiodobutane, 1,6-diiodohexane, 1,8-diiodooctane, anhydrous potassium carbonate, and other reagents were purchased from commercial sources (Fisher Scientific, Sigma-Aldrich and TCI chemicals) and used as received.

$^1$H and $^{13}$C NMR spectra were measured on Bruker AV 300 spectrometers in deuterated chloroform or DMSO at room temperature or 325 K. Chemical shifts were reported as 6 value (ppm) relative to an internal tetramethylsilane (TMS) standard. Mass spectra were measured on an Agilent 6530 LCMS using the ESI ion source with the liquid chromatographic column removed. UV-vis absorption spectra were recorded on a Shimadzu UV-3600 spectrophotometer. Photoluminescence spectra were measured on a FluoroMax-3 fluorescence spectrometer. Fluorescence signals were collected by excitation at the absorption maximum of COE solution. The differential scanning calorimetry curves of vesicle solutions were measured using the Nano DSC instrument (TA Instruments). The dynamic light scattering (DLS) measurements were performed using a Malvern Nano-ZS Particle Sizer.

General Methods

Determination of Minimum Inhibitory Concentration

The respective minimum inhibition concentration (MIC) of each COE molecule was determined using a broth microdilution method. Briefly, COEs were diluted via a 2-fold dilution series in 100 µL of either Muller Hinton Broth (MHB) for *E. coli* and *S. aureus* or Brain Heart Infusion Broth (BHI) for *E. faecalis* in a 96-well plate to achieve the desired final concentration. Subsequently, each well was inoculated with 100 µL of 1×10$^6$ colony forming units (CFU) mL$^{-1}$ of the respective microorganism in MHB for *E. coli* or BHI for *E. faecalis* to achieve an inoculum density of 5×10$^5$ CFU mL$^{-1}$. The plates were then incubated at 37° C. with shaking (200 rpm) for 18 hrs. MIC values were determined as the lowest COE concentration at which microbial growth was completely inhibited by comparing the final optical density at 600 nm with positive and negative growth controls at the start and end of the 18 hrs incubation period. The results were obtained in triplicate.

Cellular Uptake Experiment

The relative membrane affinity of COE-D4, COE-D6 and COE-D8 was estimated from the quantity taken up by cells using absorption spectroscopy. After cultures of *E. coli* K12 were grown in MHB at 37° C., the cells were harvested by centrifugation (6000 rpm, 5 min) and washed twice with PBS solution (pH=7.2). The cells were then resuspended in PBS and with the density adjusted to OD=1.0. Thereafter, 5 mL of this cell suspension was mixed with an equal volume of 20 µg/mL of COE in PBS to achieve a final concentration of 10 µg/mL (in triplicates). After exposure to COEs for 2 hrs at room temperature and with shaking (200 rpm), the cells were removed by centrifugation and the supernatant was collected for absorbance scans to quantify the remaining COE in the supernatant. The uptake quantity was estimated by comparing the absorbance of the supernatant to the corresponding control COE solution (i.e. 10 µg/mL in PBS). The procedure for uptake measurements at the lower temperature is similar to the one described above, but with the exposure to COEs and centrifugation occurring at 4° C. instead of room temperature SEM Characterisations

*E. coli* K-12 was grown, collected and washed according to the procedure described above (in the uptake measurements). COE solutions (in PBS) were added to a PBS suspension of *E. coli* K12 (OD$_{600}$=1.0) to achieve final COE concentrations of 32 µg/mL. After incubating for 2 hrs at room temperature under shaking (200 rpm), the microbes were immediately fixed with 2.5% glutaraldehyde solution at 4° C. overnight. 10 µL of the fixed bacteria suspension was spotted onto the SEM conducting paste and left to dry in air. The bacteria samples were dehydrated with a series of increasingly concentrated ethanol solution (20%-100%). After drying overnight, the samples were coated with platinum and imaged with FESEM (JEOL JSM-6700F) to characterise the morphology of the samples.

Epifluorescence Microscopy

*E. coli* K-12 was grown, collected and washed according to the procedure described above (in the uptake measurements). COE solutions (in PBS) were added to a PBS suspension of *E. coli* K12 (OD$_{600}$=1.0) to achieve final COE concentrations of 32 µg/mL. After incubating for 2 hrs at room temperature under shaking (200 rpm), a drop of suspension was placed on a microscope slide with a cover slip (#1.5, 0.17 mm thickness) and imaged using an inverted widefield epifluorescence microscope with Plan-Apochromat 100x/1.4 phase contrast with oil immersion lens (Carl Zeiss Axio Observer Z1 Inverted Microscope). The fluorescence microscopy images were observed by collecting the fluorescence signal of COEs using the DAPI dye channel (filter set 49 DAPI with excitation peak at 365 nm and emission at 445/50 nm). The bright field images of cells were obtained at exact same location using phase contrast transmitted light technique (Plan-Apochromat 100x/1.4 phase contrast with oil immersion lens). The cell images treated by different COEs were obtained under identical conditions with the matching irradiation frequency and exposure time.

Synthesis of trans-stilbene-4,4'-diol (2)

Trans-stilbene-4,4'-diol (2) was synthesised via the McMurry coupling as described in reported method (R. Baskin, et al., *Bioorg. Med. Chem. Lett.* 2012, 22, 1402-1407).

$^1$H NMR (300 MHz, DMSO-d$_6$) δ 9.47 (s, 2H), 7.35 (d, J=8.6 Hz, 4H), 6.89 (s, 2H), 6.74 (d, J=8.6 Hz, 4H).

Preparation of Small Unilamellar Vesicles

POPE (1-palmitoyl-2-oleoyl-phosphatidylethanolamine) and POPG (1-palmitoyl-2-oleoyl-phosphatidylglycerol) were purchased as chloroform stocks from Avanti Polar Lipids. POPE and POPG were mixed to a molar ratio of 85:15 and dried under a gentle stream of nitrogen. The lipid cake obtained was further desiccated for overnight to obtain a thin lipid film. Rehydration of the dried film was carried out by adding 25 mM Tris, 150 mM NaCl, pH 7.5, to a concentration of 4.3 mg/mL, followed by incubation at 45° C. for 2 hrs, under constant stirring using a magnetic stirrer at around 300 rpm. To prepare the unilamellar vesicles, the vesicles suspension was repeatedly extruded through a polycarbonate membrane of 100 nm pores (21 times) at 45° C. The extruded vesicle sample was kept at 4° C. till further use. The vesicle solution was diluted to 0.86 mg/mL with buffer (25 mM Tris, 150 mM NaCl, pH 7.5) or the COE solution (25 mM Tris, 150 mM NaCl, pH 7.5) before the DSC measurements.

Example 1. Synthesis of Conjugated Oligoelectrolytes of the Current Invention (COE-D4, COE-D6, COE-D8, COE-D62N and COE-D82N)

Figure 1B:
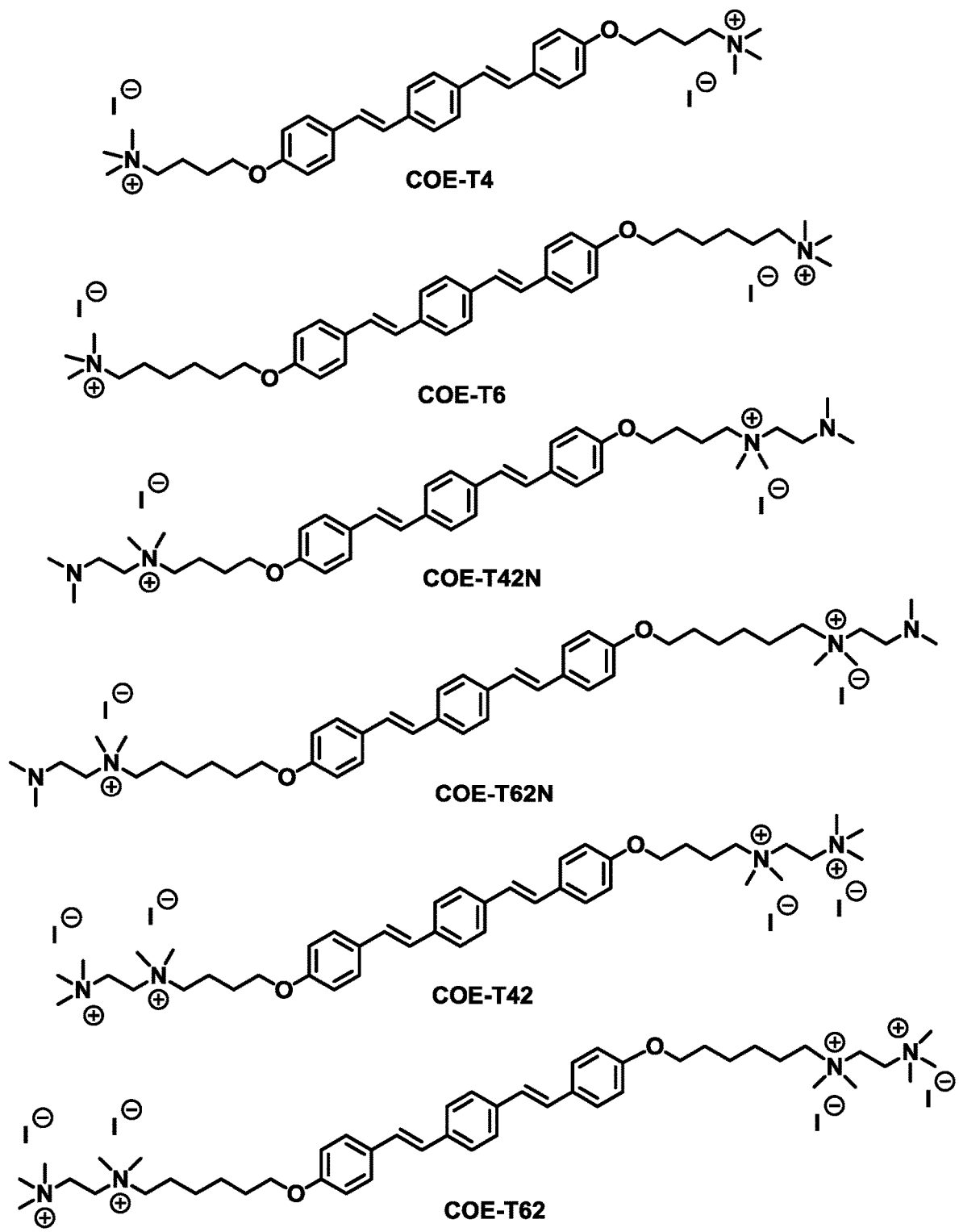

A series of COE compounds of the current invention were synthesised and their molecular structures are as shown in FIGS. 1A and 1B. These COEs vary structurally in terms of the hydrophobic conjugated backbone (phenylenevinylene), alkyl chain length and the number of amine and ammonium groups.

Figure 2:
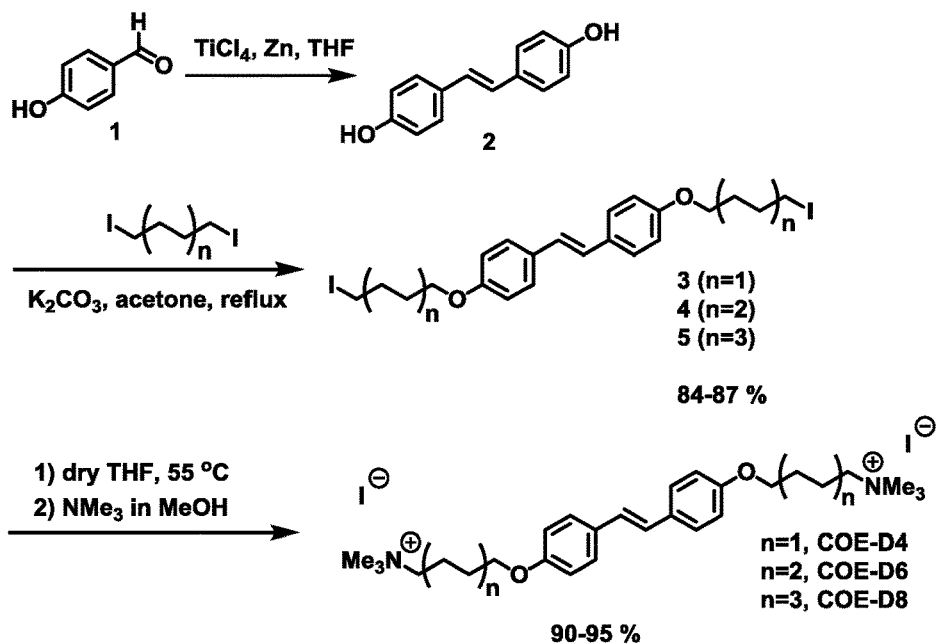
FIG. 2 Depicts the synthesis of: (a) COE-D4, COE-D6 and COE-D8; and (b) COE-D62N and COE-D82N.
Figure 2:
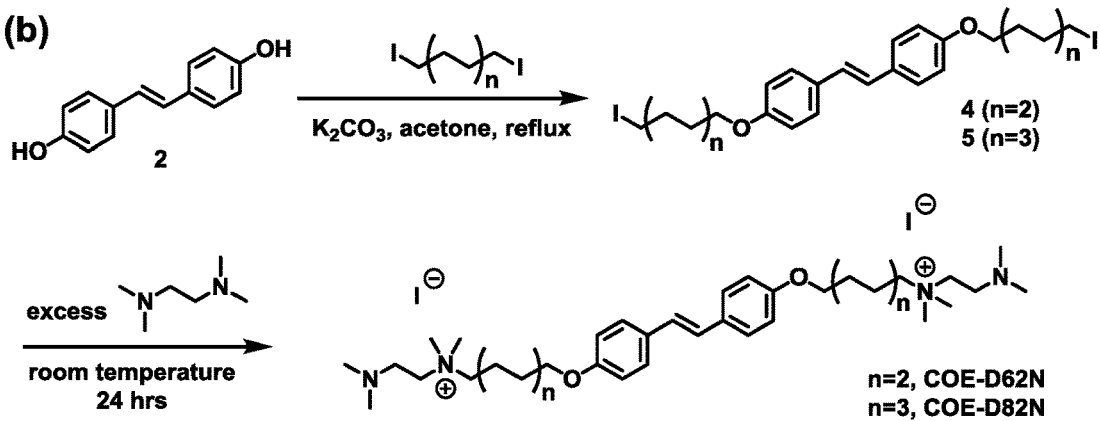

As an example, the synthetic routes for certain embodiments of the current invention (COE-D4, COE-D6 and COE-D8) are described below (FIG. 2a), with the syntheses beginning with the starting material, trans-stilbene-4,4'-diol (2) (synthesised according to the general method above). It is appreciated that the reaction conditions and synthesis method can be adapted accordingly to produce the COEs of the current invention. For example, COE-D62N and COE-D82N can also be synthesised easily, similarly starting from 2 (FIG. 2b).

In a typical reaction for the synthesis of COE-D4, COE-D6 and COE-D8, an excess of α,ω-diiodoalkane was employed in an aryl ether forming step to minimise oligomerisation reactions. The neutral precursors were precipitated from chloroform into acetone, and further purified by washing with acetone. The target COE compounds were obtained by quaternisation of the terminal alkyl iodide groups with trimethylamine, followed by solvent removal under vacuum. The simple synthesis and purification steps are advantageous as compared to peptide synthesis, demonstrating potential for low-cost production. The intermediates and products were characterised by NMR spectroscopy and mass spectrometry. Specific details of the synthesis are described below.

Synthesis of COE-D4 Via Compound 3

Synthesis of (E)-1,2-bis(4-(4-iodobutoxy)phenyl)ethane (3)

Compound 2 (0.12 g, 0.565 mmol, 1 eq), anhydrous potassium carbonate (0.39 g, 2.83 mmol, eq), and 1,4-diiodobutane (3.5 g, 11.3 mmol, 20 eq) were added to a two-neck round flask and purged with Ar. Subsequently, 50 mL acetone was injected into the mixture and then stirred at reflux for 36 hrs. Upon cooling to room temperature, the reaction mixture was poured into 100 mL water, and extracted with 200 mL heated chloroform (55° C.). The transparent organic phase was dried over $Na_2SO_4$ and then the organic solvent was removed by evaporation using a rotary evaporator. Precipitates were obtained by adding 20 mL of acetone into the mixture, and were removed by filtration and then purified by washing with acetone. The precipitates were dried in vacuum and the final product was obtained as a white solid (273 mg, 84% yield).

$^1$H NMR (300 MHz, 325K, Chloroform-d) δ 7.41 (d, J=8.4 Hz, 4H), 6.92 (s, 2H), 6.87 (d, J=8.4 Hz, 4H), 4.08-3.96 (m 4H), 3.33-3.22 (m 4H), 2.12-1.99 (m 4H), 1.97-1.85 (m 4H).

$^{13}$C NMR (75 MHz, 325K, CDCl$_3$) δ 158.8, 131.2, 127.8, 126.8, 115.3, 67.3, 30.7, 30.7, 6.3.

Synthesis of COE-D4

A single-neck round flask was charged with compound 3 (130 mg, 0.226 mmol) and THF (10 mL) under Ar atmosphere, and was heated to 55° C. to dissolve the compound 3. A large excess of trimethylamine solution in methanol (5 mL, 3.2 M) was added into the mixture. The resulting solution was stirred at 55° C. for 24 hrs. The solvent was removed via rotary evaporation and dried in vacuum. The final product was obtained as an off-white solid (149 mg, 95% yield).

$^1$H NMR (300 MHz, DMSO-d$_6$) δ 7.50 (d, J=8.8 Hz, 4H), 7.04 (s, 2H), 6.95 (d, J=8.8 Hz, 4H), 4.11-3.99 (m, 4H), 3.43-3.34 (m, 4H), 3.07 (s, 18H), 1.93-1.80 (m, 4H), 1.80-1.68 (m, 4H).

$^{13}$C NMR (75 MHz, DMSO-d$_6$) δ 158.7, 131.0, 128.3, 126.7, 115.6, 67.6, 65.9, 53.1, 26.5, 20.2.

MS (ESI) m/z: $[M-2I]^{2+}$ calcd. 220.2; found 220.2.

Synthesis of COE-D6 Via Compound 4

Synthesis of (E)-1,2-bis(4-((6-iodohexyl)oxy)phenyl)ethane (4)

Compound 4 was synthesised according to the procedure as described above for compound 3. The final product was obtained as a white solid (254 mg, 87% yield).

$^1$H NMR (300 MHz, 325K, Chloroform-d) δ 7.40 (d, J=8.7 Hz, 4H), 6.92 (s, 2H), 6.87 (d, J=8.7 Hz, 4H), 4.06-3.94 (m, 4H), 3.28-3.17 (m, 4H), 1.96-1.74 (m, 8H), 1.59-1.45 (m, 8H).

$^{13}$C NMR (75 MHz, 325K, CDCl$_3$) δ 159.0, 131.0, 127.8, 126.7, 115.3, 68.4, 33.9, 30.7, 29.5, 25.5, 6.8.

Synthesis of COE-D6

Compound 4 was used for the same quaternisation reaction as described above for the synthesis of COE-D4. The product COE-D6 was obtained as an off-white solid (122 mg, 93% yield).

$^1$H NMR (300 MHz, DMSO-d$_6$) δ 7.48 (d, J=8.8 Hz, 4H), 7.02 (s, 2H), 6.92 (d, J=8.8 Hz, 4H), 4.04-3.95 (m, 4H), 3.32-3.24 (m, 4H), 3.05 (s, 18H), 1.82-1.64 (m, 8H), 1.56-1.41 (m, 4H), 1.41-1.28 (m 4H).

$^{13}$C NMR (75 MHz, DMSO-d$_6$) δ 158.9, 130.8, 128.3, 126.6, 115.5, 68.2, 66.2, 53.1, 29.3, 26.4, 26.0, 22.9.

MS (ESI) m/z: $[M-2I]^{2+}$ calcd. 248.2; found 248.2.

Synthesis of COE-D8 Via Compound 5

Synthesis of (E)-1,2-bis(4-((8-iodooctyl)oxy)phenyl)ethene (5)

Compound 5 was synthesised according to the procedure as described above for compound 3 above. The final product was obtained as a white solid (244 mg, 87% yield).

$^1$H NMR (300 MHz, 325K, Chloroform-d) δ 7.40 (d, J=8.8 Hz, 4H), 6.91 (s, 2H), 6.87 (d, J=8.8 Hz, 4H), 4.04-3.94 (m, 4H), 3.26-3.14 (m, 4H), 1.92-1.73 (m, 8H), 1.55-1.33 (m, 16H).

$^{13}$C NMR (75 MHz, 325K, CDCl$_3$) δ 159.1, 131.0, 127.8, 126.7, 115.3, 68.5, 34.0, 30.8, 29.7, 29.5, 28.8, 26.4, 7.1.

Synthesis of COE-D8

Compound 5 was used for the same quaternisation reaction as described above for the synthesis of COE-D4. The product COE-D8 was obtained as an off-white solid (137 mg, 90% yield).

$^1$H NMR (300 MHz, DMSO-$d_6$) δ 7.48 (d, J=8.9 Hz, 4H), 7.02 (s, 2H), 6.91 (d, J=8.8 Hz, 4H), 4.03-3.93 (m, 4H), 3.31-3.22 (m, 4H), 3.04 (s, 18H), 1.79-1.60 (m, 8H), 1.49-1.22 (m, 16H).

$^{13}$C NMR (75 MHz, DMSO-$d_6$) δ 159.0, 130.8, 128.3, 126.6, 115.5, 68.3, 66.2, 53.1, 29.6, 29.4, 29.4, 26.6, 26.3, 22.9.

MS (ESI) m/z: $[M-2I]^{2+}$ calcd. 276.2; found 276.2.

Example 2. Characterisation of COE-D4, COE-D6 and COE-D8

The as-synthesised COEs of the current invention were characterised by dynamic light scattering, UV/vis absorption, photoluminescence spectroscopy.

Figure 3:
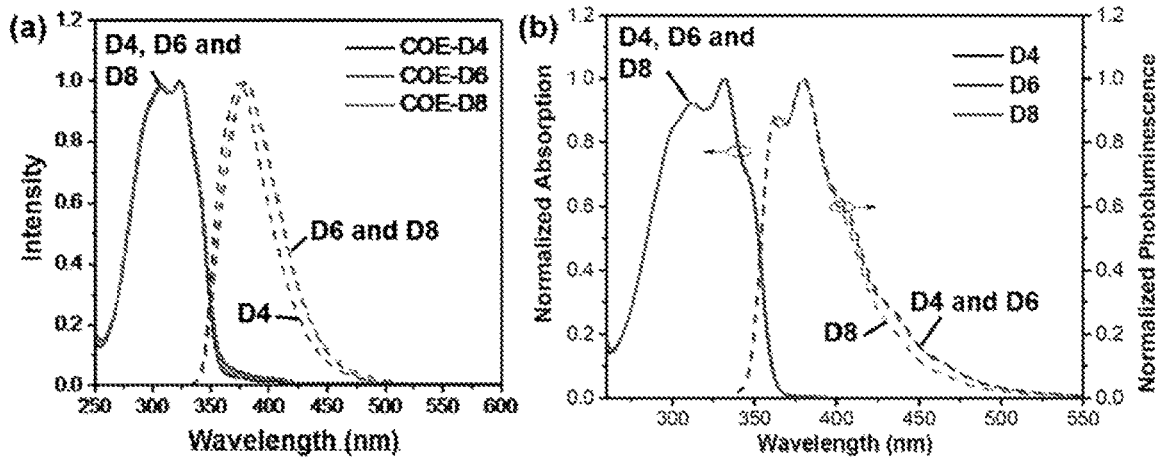
FIG. 3 Depicts the normalised absorption (solid) and photoluminescence emission (dash) spectra of COE-D4, COE-D6 and COE-D8 in: (a) PBS; and (b) DMSO. Fluorescence signals were collected at the maximum excitation wavelength (i.e. 324 nm for the PBS solutions and 332 nm for the DMSO solutions).
Figure 4:
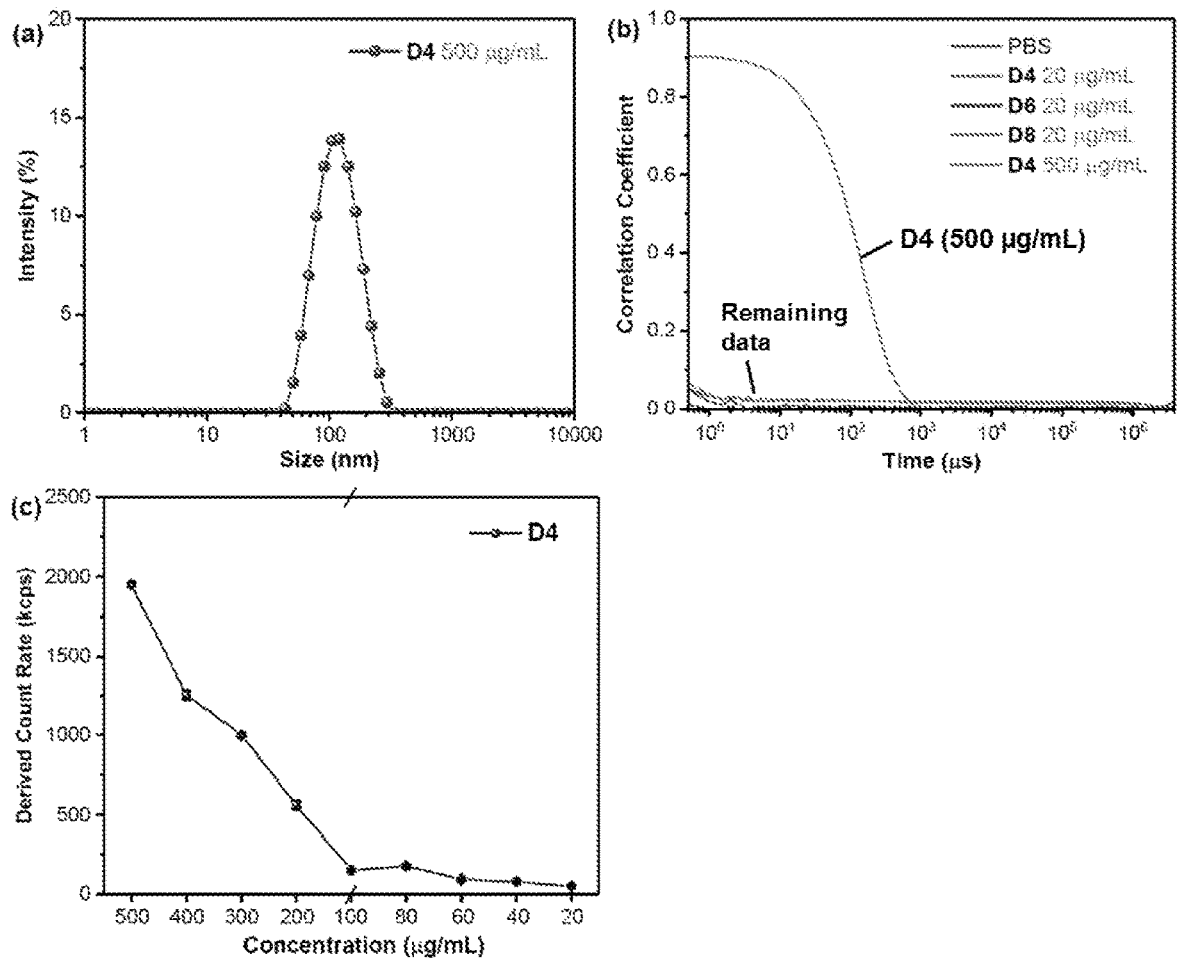
FIG. 4 Depicts: (a) size distribution profiles of COE-D4 (high concentration) as measured by dynamic light scattering (DLS); (b) the corresponding correlation curves of the various COEs in PBS solution during the DLS measurements; and (c) concentration-dependent derived count rate during the DLS measurements of COE-D4 in PBS solution.

Normalised UV/Vis absorption and photoluminescence spectra of COE-D4, COE-D6, and COE-D8 were obtained in phosphate buffered saline (PBS) and in DMSO solution (FIGS. 3a and b). As expected, the three COEs show similar absorption maxima at λ=324 nm as they contain the same photoresponsive conjugated stilbene core. The absorption coefficients decrease slightly with increasing alkyl spacer length ($2.9 \times 10^4$ $M^{-1}$ cm-1 for COE-D4, $2.6 \times 10^4$ $M^{-1}$ $cm^{-1}$ for COE-D6, and $2.4 \times 10^4$ $M^{-1}$ $cm^{-1}$ for COE-D8). The emission curves of the three COE molecules are essentially the same. After excitation at their maximum absorption (λ=324 nm), the COE-D4 emission curve displayed a maximum at λ=374 nm. Slightly red-shifted spectra were observed for COE-D6 and COE-D8, with emission maxima at λ=381 and 380 nm, respectively. The fluorescence quantum efficiencies for COE-D4, COE-D6, and COE-D8 determined relative to tryptophan as a standard were in the range of 5-6%. Dynamic light scattering (DLS) analysis indicated no obvious COE aggregation at experimentally relevant concentration for COE-D4 (FIG. 4a). The correlation curves of COEs and the concentration-dependent derived count rate of COE-D4 in PBS solution are as shown in FIGS. 4b and c respectively. The lower solubility of COE-D6 and COE-D8 preclude similar concentration-dependent measurements to be carried out. These results indicated that there is no large aggregates when COEs were used in the experimental concentration (below 20 μg/mL); the concentrations near the MIC were not enough to promote the formation of the large aggregates for the COEs.

The optical properties, solubility and *E. coli* uptake of COE-D4, COE-D6 and COE-D8 in PBS are summarised in Table 1a, while their optical properties in DMSO are summarised in Table 1b. The optical properties for COE-T4 and COE-T6 are as shown in Table 1c.

The hydrophobicity and molecular length of COE-D4, COE-D6 and COE-D8 were also calculated and summarised in Table 2. The charge density of these three COEs were kept low to decrease aqueous solubility, so as to shift the equilibrium towards membrane intercalation while keeping the LogP in a clinically acceptable range (LogP s 5). As the phenylenevinylene sequence length is a stilbene core, the molecular length and relative hydrophobicity of COE-D4, COE-D6 and COE-D8 was regulated by controlling the length of the alkyl chains that connect the stilbene fragment to the two terminal ammonium groups, from —$C_4H_8$— (C4) to —$C_8H_{16}$— (C8). Molecular simulations indicated fully extended molecular lengths of 2.6 nm for COE-D4, 3.1 nm for COE-D6, and 3.6 nm for COE-D8 (Table 2).

TABLE 1a

Summary of UV-Vis and PL spectra, solubility, and uptake of COE-D4, COE-D6 and COE-D8 in PBS.

| Compound | COE-D4 | COE-D6 | COE-D8 |
|---|---|---|---|
| $\lambda_{abs}$ (nm) | 324 | 324 | 324 |
| $\lambda_{em}$ (nm) | 374 | 381 | 380 |
| ε ($\times 10^4$ $M^{-1}$ $cm^{-1}$) | 2.9 ± 0.1 | 2.6 ± 0.1 | 2.4 ± 0.2 |
| $\Phi_F$ (%) | 6 | 5 | 5 |
| Solubility in PBS (μg/mL) | 3100 | 240 | 65 |
| Uptake by *E. coli* K12 (%) - see Example 4 | 3 ± 2 | 16 ± 3 | 72 ± 5 |

TABLE 1b

Summary of UV-Vis and PL spectra of COE-D4, COE-D6 and COE-D8 in DMSO. Molar extinction coefficients were measured at the maximum absorption peak.

| Compound | COE-D4 | COE-D6 | COE-D8 |
|---|---|---|---|
| Molecular weight (g/mol) | 694.48 | 750.59 | 806.70 |
| $\lambda_{abs}$ (nm) | 332 | 332 | 332 |
| $\lambda_{em}$ (nm) | 379 | 380 | 380 |
| ε ($\times 10^4$ $M^{-1}$ $cm^{-1}$) | 3.4 ± 0.2 | 3.3 ± 0.1 | 3.5 ± 0.2 |

TABLE 1c

Summary of UV-Vis and PL spectra, solubility of COE-T4 and COE-T6 in PBS.

| Compound | COE-T4 | COE-T6 |
|---|---|---|
| Molecular weight (g/mol) | 796.62 | 852.72 |
| $\lambda_{abs}$ (nm) | 342 | 344 |
| ε ($\times 10^4$ $M^{-1}$ $cm^{-1}$) | 3.4 | 2.8 |
| $\lambda_{em}$ (nm) | 452 | 452 |
| Solubility in PBS (μg/mL) | 210 | 76 |
| Uptake by *E. coli* K12 (%) - see Example 4 | 80 | 89 |

TABLE 2

Simulated molecular length, logP data for COE-D4, COE-D6 and COE-D8 using GaussView and Molinspiration software respectively.

| Compound | COE-D4 | COE-D6 | COE-D8 |
|---|---|---|---|
| Length (nm) | 694.48 | 750.59 | 806.70 |
| LogP | −2.2 | −0.18 | 1.8 |

Example 3. Antimicrobial Effects of the as-Synthesised COEs on Various Bacteria and Fungi The as-synthesised COEs of the current invention was investigated on various bacteria and fungi to determine their antimicrobial effect. The initial investigation was carried out on bacterial strains with the minimum inhibitory concentration (MIC) of the COEs determined. Subsequent studies were then carried out on a single dose of COEs on various bacteria and fungi to compare their extent of inhibition on these microorganisms.

Initial Studies

The MIC values of COE-D4, COE-D6 and COE-D8 against the reference strain E. coli K12, pathogenic E. coli UT189, and the Gram positive pathogen Enterococcus faecalis OG1RF were determined using a broth microdilution method as described in the general method above. The MICs for E. coli K12 were determined to be 128, 16, and 4 µg mL$^{-1}$ for COE-D4, COE-D6, and COE-D8, respectively (FIG. 5a). For all three bacteria, it was observed that the antimicrobial activity significantly increased with increasing alkyl chain length. The urinary tract pathogen E. coli UT189 was observed to be invariably more tolerant than E. coli K12. This is not surprising as these two organisms differ in the capsular polysaccharides that they expressed, which are known to hinder the uptake of antimicrobials and mitigate their potency (M. A. Campos, et al., Infect. Immun. 2004, 72, 7107-7114). A K-type capsid comprising α2-8-linked sialic acid is excreted by UT189 and is known to be an important virulence factor for this organism (C. Whitfield, et al., Mol. Microbiol. 1999, 31, 1307-1319; G. G. Anderson, et al., Infect. Immun. 2010, 78, 963-975).

The activity of COE-D8 was observed to be better than that of previously reported COEs, such as COE1-3Py, with an MIC of 4 µg mL$^{-1}$ (for COE-D8) as compared to 47 µg mL$^{-1}$ (for COE1-3Py). Additionally, the MIC of COE-D8 is comparable to those of existing cell-envelope-targeting antimicrobials. For example, the MIC of colistin against multidrug-resistant Gram-negative bacteria (in general) is determined to be ≤ 4 µg mL$^{-1}$ (M. E. Falagas, et al., Clin. Infect. Dis. 2005, 40, 1333-1341), and the MIC for the Gram-positive-specific antimicrobial daptomycin against E. faecalis in brain heart infusion media is around 3 µg mL$^{-1}$ (T. T. Tran, et al., mBio 2013, 4, e00281-00213). Interestingly, COE-D8 is equally effective against Gram-negative E. coli and the Gram-positive organism E. faecalis (MIC=4 µg mL$^{-1}$). This promising attribute is of particular importance as these two organisms are often co-indicated in urinary tract infections (D. Keogh, et al., Cell Host Microbe 2016, 20, 493-503). The antimicrobial effect of the remaining COEs was also tested and their results against E. coli K12 are summarised in Table 3 below.

TABLE 3

Antimicrobial activities of COEs of the current invention against E. coli K12.

| No. | Compound | MIC (µg/mL) |
|---|---|---|
| 1 | COE-D4 | 128 |
| 2 | COE-D6 | 16 |
| 3 | COE-D8 | 4 |
| 4 | COE-D42N | 32 |
| 5 | COE-D62N | 8 |
| 6 | COE-D82N | 8 |
| 7 | COE-D42 | 128 |
| 8 | COE-D62 | 16 |
| 9 | COE-D82 | 32 |
| 10 | COE-T4 | 32 |
| 11 | COE-T6 | >16 |
| 12 | COE-T42N | 8 |
| 13 | COE-T62N | 64 |
| 14 | COE-T42 | 16 |
| 15 | COE-T62 | 16 |

The antimicrobial effects of COE-D62N and COE-D82N were also tested on the Gram-positive Staphylococcus aureus 25923 and Methicillin-resistant Staphylococcus aureus(MRSA BAA-40), in comparison with vancomycin (FIG. 5b). It was observed that COE-D62N and COE-D82N demonstrated lower MIC than vancomycin for all three strains of bacteria, particularly for the resistant strain of Staphylococcus aureus (MRSA).

Subsequent Studies

In subsequent studies, the antimicrobial activities of the as-synthesised COEs were tested on a wider spectrum of bacteria and fungi as listed in Table 4.

TABLE 4

List of bacteria and fungi used in these studies

| Name | Abbreviation | Description | Strain | Organsim | Type |
|---|---|---|---|---|---|
| Staphylococcus aureus | Sa | MRSA | ATCC 43300 | Bacteria | Gram positive |
| Escherichia coli | Ec | FDA control | ATCC 25922 | Bacteria | Gram negative |
| Klebsiella pneumoniae | Kp | Multiple drug resistance (MDR) | ATCC 700603 | Bacteria | Gram negative |
| Acinetobacter baumannii | Ab | Type strain | ATCC 19606 | Bacteria | Gram negative |
| Pseudomonas aeruginosa | Pa | Type strain | ATCC 27853 | Bacteria | Gram negative |
| Candida albicans | Ca | Clinical & Laboratory Standards Institute (CLSI) reference | ATCC 90028 | Fungi | Yeast |
| Cryptococcus neoformans var. grubii | Cn | Type strain | H99; ATCC 208821 | Fungi | Yeast |

Method

Data Collection for Bacteria Sample

Inhibition of bacterial growth was determined by measuring the absorbance at 600 nm ($OD_{600}$), using a Tecan M1000 Pro monochromator plate reader. Growth inhibition was calculated for each well, relative to the reference growths determined from a negative control (media only) and positive control (bacteria without inhibitors) incubated in the same plate. A single dose of 32 µg/mL of COE (final concentration) was used for each test.

Data Collection for Fungi Sample

Growth inhibition of C. albicans was determined by measuring the absorbance at 530 nm ($OD_{530}$), while the growth inhibition of C. neoformans was determined by measuring the difference in absorbance between 600 and 570 nm ($OD_{600-570}$), after the addition of resazurin (0.001 wt. % final concentration) and incubation at 35° C. for additional 2 hrs. The absorbance was measured using a Biotek Synergy HTX plate reader. The relative growth inhibition was calculated for each well, relative to that determined from a negative control (media only) and positive control (bacteria without inhibitors) on the same plate as references. A single dose of 32 µg/mL of COE (final concentration) was used for each test.

Calculation of Percentage Growth Inhibition

Percentage growth inhibition of an individual sample was calculated based on growth in a reference well determined from negative controls (media only) and positive controls (bacterial/fungal media without inhibitors). Negative inhibition values indicate that the growth rate (or $OD_{600}$) is higher compared to the reference growth (bacteria/fungi only, set to 0% inhibition). The growth rates for all bacteria and fungi may vary at −/+10%, which were within the reported normal distribution of bacterial/fungal growth. Any significant variations (or outliers/hits) were identified by the modified Z-Score, and the active compounds were selected by a combination of inhibition values and Z-Score.

Z-Score Analysis

Z-Score analysis was carried out to investigate outliers or hits among the samples. The Z-Score was calculated based on the sample population using a modified Z-Score method which accounts for possible skewed sample population. The modified method uses median and MAD (median average deviation) instead of average and standard deviation, and a scaling factor (Iglewicz, B. & Hoaglin, D. C. Volume 16: How to Detect and Handle Outliers. The ASQC Basic Reference in Quality Control: Statistical Techniques, 1993). The equation to calculate the modified Z-Score value is as follow:

$$M(i) = \frac{0.6745(x_i - \bar{x})}{MAD}$$

where M(i) denotes the modified Z-Score value;
$x_i$ denotes the sample value;
$\bar{x}$ denotes the median; and
MAD denotes the median absolute deviation.

A M(i) value of >|2.5| (absolute) would classify the sample as outliers or hits. Active samples were denoted as compounds with inhibition values equal to or above 80% and absolute Z-Score above |2.5| for either replicate (n=2 on different plates). Partial active samples were denoted as compounds with inhibition values from 50% to <80%, or absolute Z-Score below |2.5|. Lastly, inactive samples were denoted as compounds with inhibition values below 50% and/or absolute Z-Score below |2.5|.

Quality Control

All screening experiments were performed in two replica (n=2), with both replicas carried out on different assay plates, but from a single plating and performed in a single screening experiment (microbial incubation). The values of the Z'-Factor and the standard antibiotic controls at different concentrations (>MIC and <MIC) were used as quality controls for individual plates. The Z'-Factor can be derived as follow:

$$Z'\text{Factor} = 1 - \frac{3(sd \text{ negative control} + sd \text{ positive control})}{\text{average of positive control} - \text{average of negative control}}$$

where sd denotes standard deviation.

The plate passes the quality control if Z'-Factor >0.4 and the antibiotic standards are active and inactive at the highest and lowest concentrations, respectively.

Results and Discussions

The results of the subsequent studies of COEs on various bacteria and fungi are as shown in Table 5 below.

TABLE 5

Summary of the antimicrobial efficacy of the COEs (32 μg/mL) of the current invention on various bacteria and fungi.

| | | | Growth inhibition[10] | | | | | | |
|---|---|---|---|---|---|---|---|---|---|
| | | | Gram-positive bacteria | | Gram-negative bacteria | | | Fungi | |
| Compound | Selection[1] | Activity[2] | Sa[3] | Kp[4] | Ec[5] | Pa[6] | Ab[7] | Ca[8] | Cn[9] |
| COE-D4 | 2 | 2 | A | NA | NA | NA | NA | NA | A |
| COE-D6 | 3 | 3 | A | NA | A | NA | NA | A | A |
| COE-D8 | 3 | 3 | A | PA | A | PA | A | A | A |
| COE-D42N | 3 | 3 | A | NA | A | NA | NA | NA | A |
| COE-D62N | 3 | 3 | A | NA | A | NA | A | A | A |
| COE-D82N | 3 | 3 | A | A | A | PA | A | A | A |
| COE-D42 | 1 | 1 | A | NA | NA | NA | NA | NA | NA |
| COE-D62 | 3 | 3 | A | A | A | NA | A | NA | A |
| COE-D82 | 3 | 3 | A | PA | A | A | PA | A | A |
| COE-T4 | 2 | 2 | A | NA | NA | NA | PA | A | A |
| COE-T6 | 2 | 2 | A | NA | NA | NA | NA | A | A |
| COE-T42N | 3 | 3 | A | NA | A | NA | A | A | A |
| COE-T62N | 3 | 2 | A | NA | NA | NA | A | A | A |
| COE-T42 | 3 | 3 | A | NA | A | NA | NA | A | A |
| COE-T62 | 3 | 3 | A | NA | A | NA | NA | A | A |

[1]Indicates the number of organism classes (Gram-negative, Gram-positive and fungi) the compound has been selected for further dose response studies and hit confirmation. The selection includes all active as well as compounds with ambiguous results requiring confirmation of activity or inactivity.
[2]Indicates the number of organism classes (Gram-negative, Gram-positive and fungi) the compound has been found active against; 0 = no activity.
[3]*Staphylococcus aureus* Gram-positive bacteria (MRSA)
[4]*Klebsiella pneumoniae* Gram-positive bacteria (MDR)
[5]*Escherichia coli* Gram-negative bacteria (FDA control)
[6]*Acinetobacter baumannii* Gram-negative bacteria (type strain)
[7]*Pseudomonas aeruginosa* Gram-negative bacteria (type strain)
[8]*Candida albicans* yeast (CLSI reference)
[9]*Cryptococcus neoformans var. grubii* yeast (type strain)
[10]Active compounds (% inhibition ≥80%), partially active compounds (% inhibition from 50% to <80%) and non-active compounds (% inhibition <50%) are denoted as "A", "PA" and "NA", respectively.

Example 4. Mechanisms of Action of the COEs on
E. coli K12

Having established the antimicrobial activity of COE-D4, COE-D6 and COE-D8, the mechanism of actions of the COEs in interacting with the bacterial membrane was investigated in greater detail. This was carried out via scanning electron microscopy, epifluorescence imaging and differential scanning calorimetry of the treated E. coli K12 or unilamellar vesicles samples. The uptake of COEs into the E. coli K12 was characterised by absorption spectroscopy.

Figure 6:
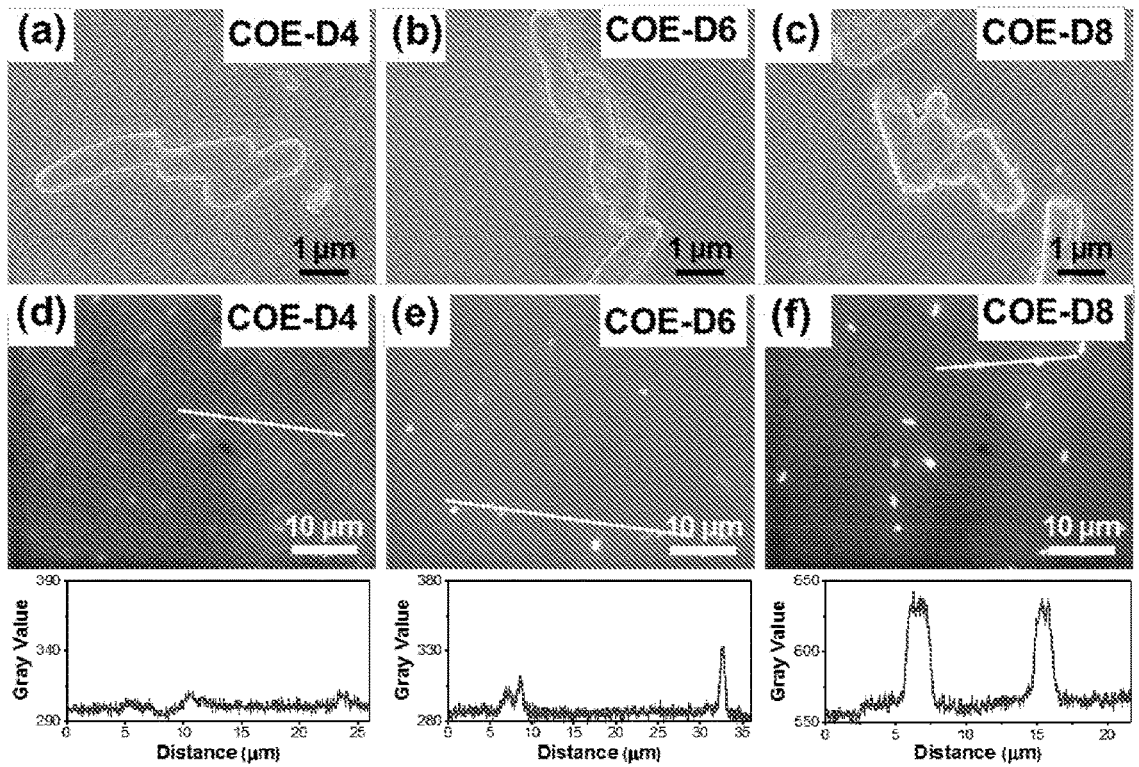
FIG. 6 Depicts: (a-c) the SEM images; and (d-f) the fluorescence images of *E. coli* K12 after treatment with 32 µg/mL of COE-D4, COE-D6 and COE-D8 in PBS, respectively. The bottom gray value curves represent fluorescence intensity and profiles to the white line in each micrograph.

Characterisation of treated E. coli K12 by scanning electron microscopy (SEM) COE-treated cells were characterised by SEM. E. coli K12 (OD=0.5) were treated with 32 μg mL$^{-1}$ of each COE. For the group treated with COE-D4, characteristic rod-shaped cells with smooth outer surfaces were observed (FIG. 6a). In contrast, after treating the bacteria with COE-D6 or COE-D8, the morphology of the bacteria was characterised by pitting and membrane rupture (FIGS. 6b and c). This is consistent with the proposal that COE insertion disrupts membrane integrity and this effect is of a greater magnitude for COE-D8.

Characterisation of Treated Unilamellar Vesicles by Differential Scanning Calorimetry (DSC)

Unilamellar vesicles composed of 1-palmitoyl-2-oleoylphosphatidylethanolamine (POPE) and 1-palmitoyl-2-oleoylphosphatidylglycero (POPG) in a molar ratio of 85:15 were prepared in accordance to the general method "Preparation of Small Unilamellar Vesicles" and were used as a generic bacterial model membrane (G. J. Gabriel, et al., Mater. Sci. Eng. R 2007, 57, 28-64).

Figure 7:
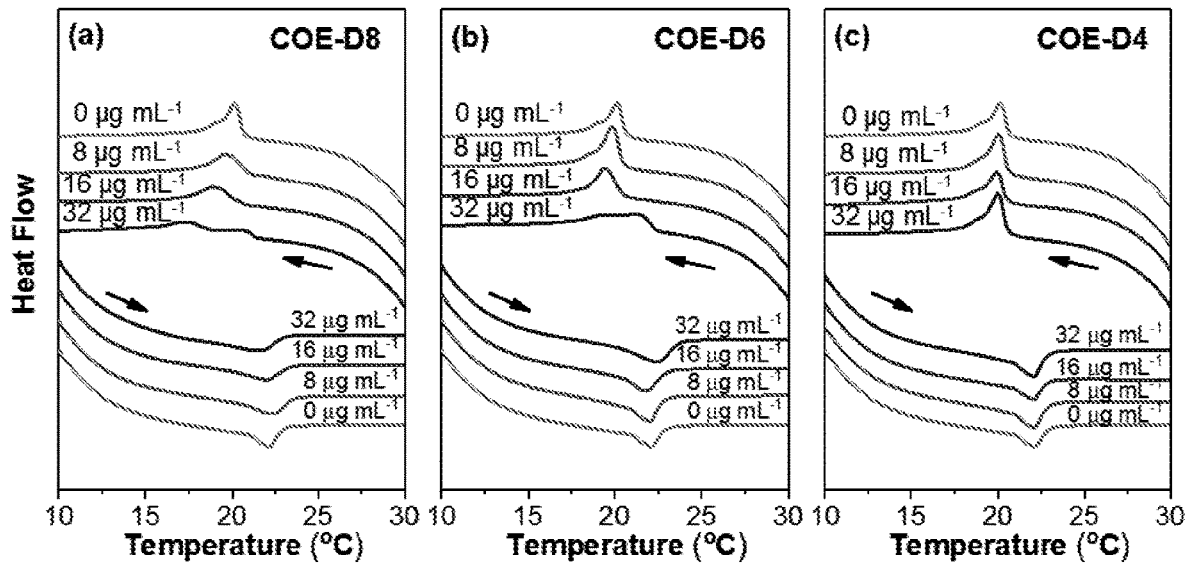
FIG. 7 Depicts the DSC curves of unilamellar vesicles (obtained at rates of 1° C. min$^{-1}$) after treatment with different concentrations of: (a) COE-D8; (b) COE-D6; and (c) COE-D4.

When subjected to DSC, the main gel-to-liquid-crystal transition peaks broadened after incubation with 8 μg mL$^{-1}$ of COE-D8 (FIG. 7a). For COE-D6, a higher concentration (16 μg mL$^{-1}$) was needed to change the initial trace (FIG. 7b). In contrast, no significant change was observed for COE-D4 up to a concentration of 32 μg mL$^{-1}$ (FIG. 7c). The perturbation to the cooperative transition of the lamellar phase reflects varying degrees of membrane intercalation. This observation correlates well with solubility and the alkyl chain length (Table 1a). Due to its lower aqueous solubility, COE-D8 is likely to partition more readily into hydrophobic domains of the lipid bilayer, leading to the weakened phase transition observed in the vesicles. Therefore, the DSC data suggests that the antimicrobial activities of COE-D4, COE-D6 and COE-D8 likely reflect their differences in interacting with the cell membrane.

Characterisation of Treated E. coli K12 by Absorption Spectroscopy

Figure 8:
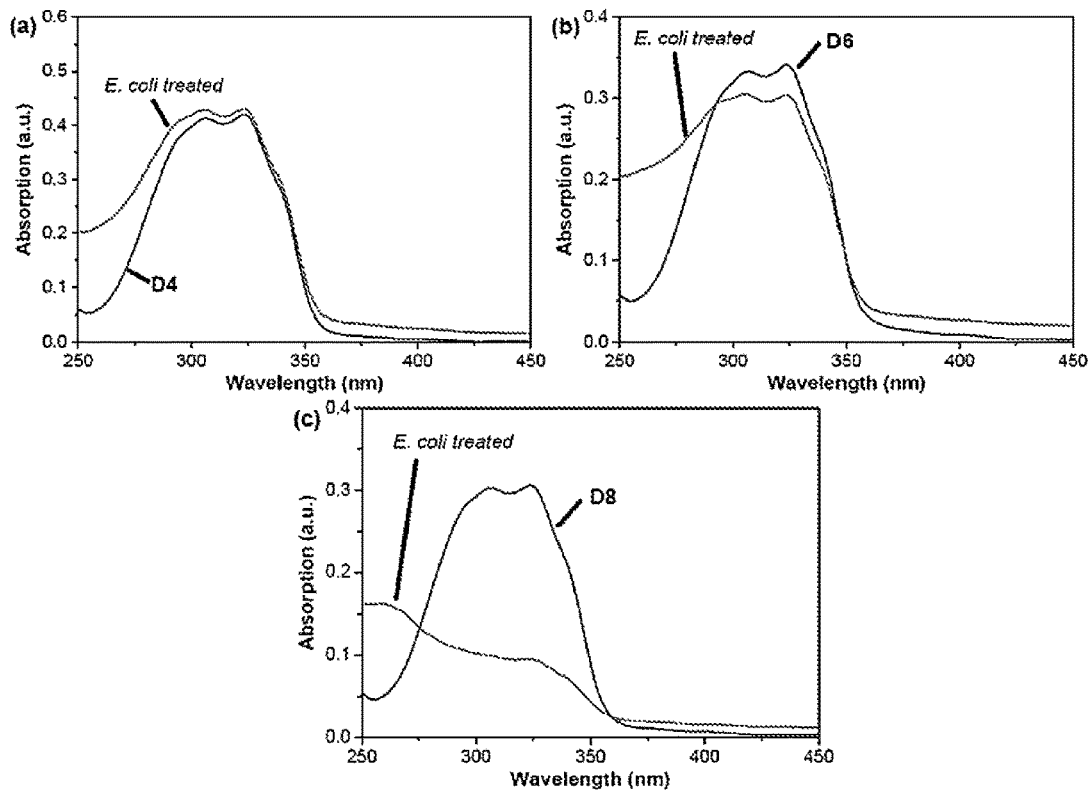
FIG. 8 Depicts the absorbance spectra of: (a) COE-D4, (b) COE-D6, (c) COE-D8 in PBS (10 µg mL$^{-1}$), in comparison with the supernatants obtained from the samples after being treated with *E. coli* K12 cells for 2 hrs and centrifuged at room temperature (25° C.).

The effect of molecular structures of the COEs on relative membrane affinity, estimated from the amount taken up by E. coli K12, was measured by absorption spectroscopy (FIG. 8a-c). These experiments utilised cell suspensions (OD=0.5) incubated for 2 hrs with 10 μg mL$^{-1}$ of various COE. Cells were removed by centrifugation, and the amount of uncomplexed COE was determined from the optical absorption spectra. The longest molecule, COE-D8, achieved the highest uptake in bacteria (72%). In contrast, only 3% of COE-D4 was absorbed while the uptake for COE-D6 was 16% (Table 1a).

Figure 9:
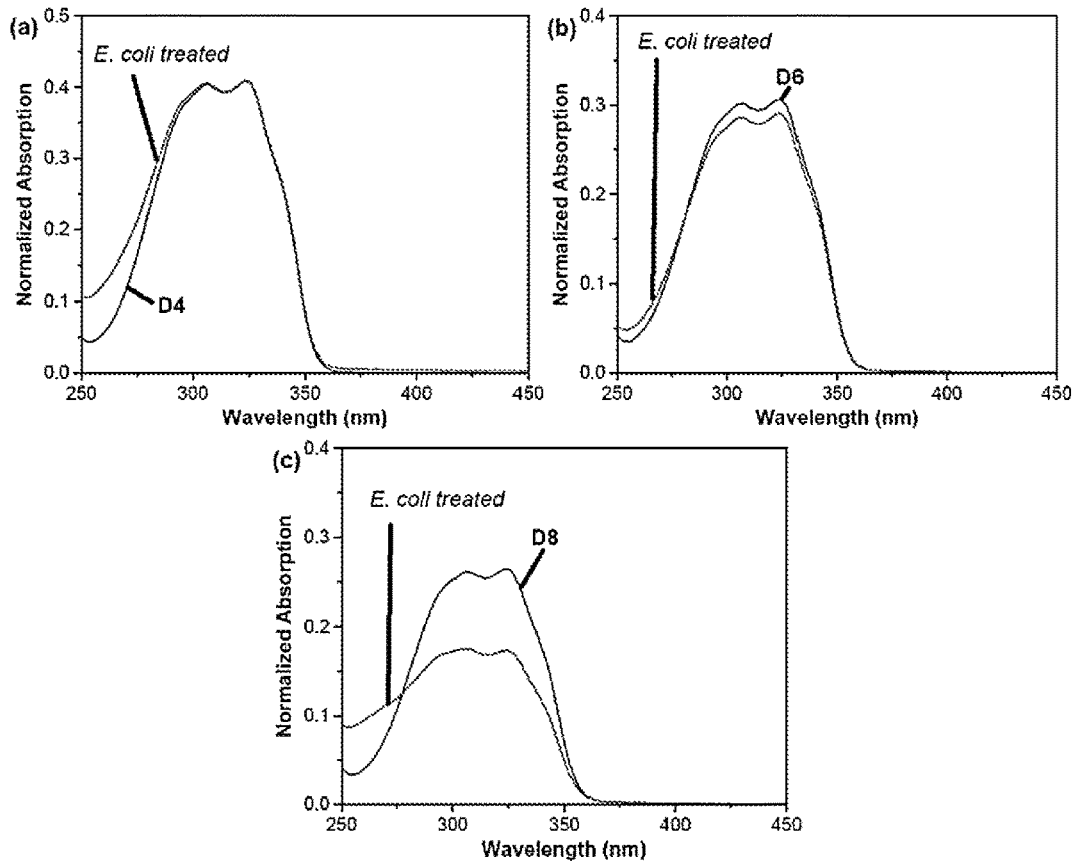
FIG. 9 Depicts the absorbance spectra of: (a) COE-D4, (b) COE-D6, (c) COE-D8 in PBS (10 µg mL$^{-1}$), in comparison with the supernatants obtained from the samples after being treated with *E. coli* K12 cells for 2 hrs and centrifuged at 4° C. (below the membrane phase transition temperature).

Parallel experiments were carried out at 4° C. (below the membrane phase transition temperature) and the results indicated that the COEs preferentially intercalated the membrane at room temperature (FIG. 9a-c). As a result of the reduced fluidity of cellular membrane at lower temperature, the uptake decreased to around 1% for COE-D4, 5% for COE-D6, and 34% for COE-D8. The large reduction in cellular uptake suggests that most COEs were incorporated into the bacteria, rather than mere physical adhesion on the membrane surface (such as electrostatic interactions).

Characterisation of Treated E. coli K12 by Epifluorescence Imaging

Figure 10:
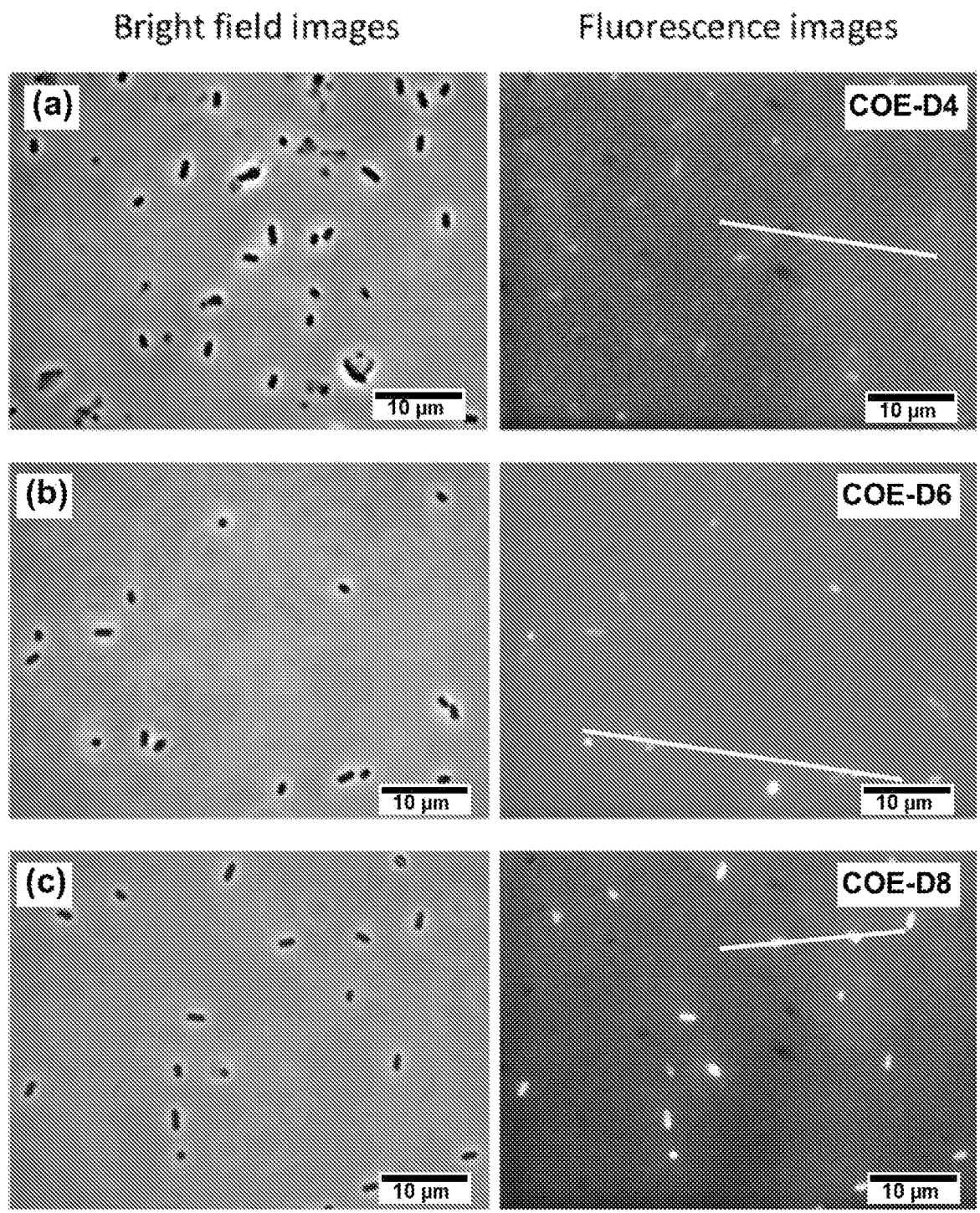
FIG. 10 Depicts the bright field (left) and fluorescence (right) microscopy images of *E. coli* K12 cells observed at the same location using the TL phase channel or DAPI dye channel respectively after being treated with 32 µg/mL of: (a) COE-D4; (b) COE-D6; and (c) COE-D8 in PBS.

Epi-fluorescence images of the COE-treated E. coli K12 cells were acquired by excitation at λ=365 nm and collecting emission at λ=445/50 nm. E. coli K12 treated with COE-D8 had the highest fluorescence intensities relative to background whereas COE-D4 treated cells showed an indistinct image (FIGS. 6d and f). Cells treated with COE-D6 showed intermediate fluorescence intensity (FIG. 6e), which can be clearly seen in the gray value profiles (bottom of FIG. 6d-f). The bright field and fluorescence images of the E. coli K12 treated with 32 μg/mL of the COEs are as shown in FIG. 10.

The epi-fluorescence microscopy results, in agreement with the uptake measurements, provided strong evidence of differential membrane accumulation. The results are also consistent with the MIC results (i.e. the lowest MIC value correlates with the greatest degree of association). The different cellular uptake of COE-D4, COE-D6, and COE-D8 was likely driven by differences in the hydrophobicity and solubility of the COEs. The shortest molecule, COE-D4, is hydrophilic and highly soluble in water and therefore has a lower driving force for partitioning into lipid membranes. For the longest molecule, COE-D8, association with the membrane is more favourable likely due to its increased hydrophobicity.

Figure 5:
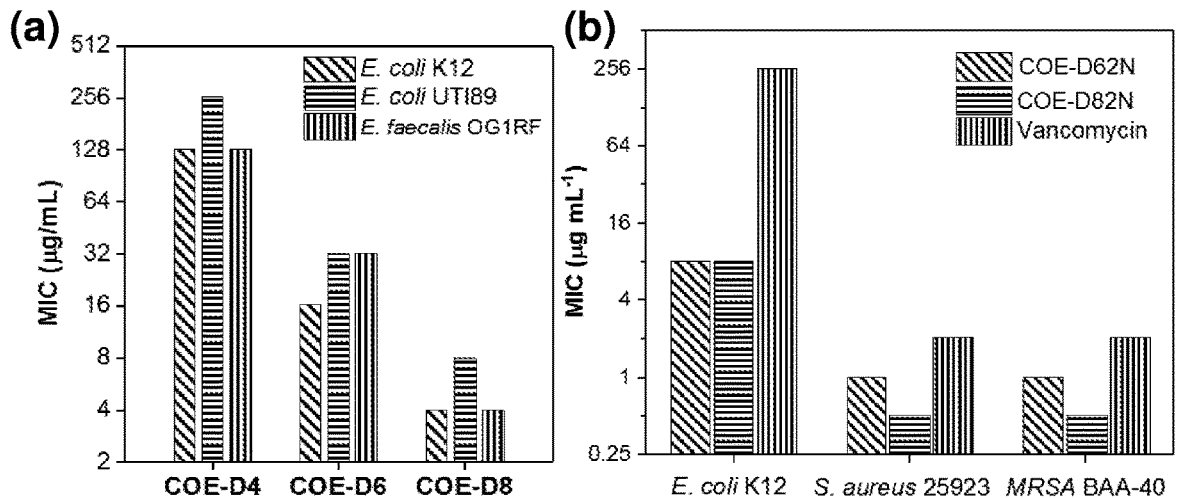
FIG. 5 Depicts the antimicrobial efficacy of the COEs of the current invention: (a) MIC values of COE-D4, COE-D6 and COE-D8 against *E. coli* K12, *E. coli* UT189, and *E. faecalis* OG1RF; and (b) MIC values of COE-D62N and COE-D82N (in comparison with vancomycin) against *E. coli* K12, *S. aureus* 25923 and MRSA BAA-40.

Another possible explanation is the dimension mismatch between the COEs and the lipid bilayer (E. Strandberg, et al., Biochim. Biophys. Acta Biomembr. 2012, 1818, 1242-1249). The length of COE-D4 is approximately 2.6 nm, and it is shorter than the thickness of the lipid bilayer (ca. 4 nm). Therefore, greater conformational reordering of the lipid bilayer is likely to be needed for COE-D4 incorporation as compared to that of COE-D8 (ca. 3.6 nm). A high degree of dimensional mismatch between the COE and the membrane would result in greater membrane disruption, however, cellular uptake limits the antimicrobial activity of COE-D4. It is interesting to note that the cell affinity of COE-D8 is 30 times larger than that of COE-D4, while the MIC values for COE-D8 and COE-D4 on E. coli K12 were 4 μg mL$^{-1}$ and 128 μg mL$^{-1}$, respectively (FIG. 5). Assuming a similar uptake percentage (U %) at MIC concentrations when OD=0.5, [COE]=10 μg mL$^{-1}$ (Table 1a), MIC$_{eff}$ is defined as MIC×U %. MIC$_{eff}$ reflects the number of molecules interacting with the cells as modulated by differences in affinity. While there are uncertainties in the determination of MIC$_{eff}$, values of 3.8 μg mL$^{-1}$ for COE-D4, 2.6 μg mL$^{-1}$ for COE-D6, and COE-2.9 μg mL$^{-1}$ for COE-D8 were obtained. These values are close to each other, revealing opportunities for designing COEs with greater antimicrobial activity on a per-inserted-molecule basis.

Relationship of Solubility of COEs on Cellular Uptake and on the MIC

Based on the solubility of the COEs, it appears that there is no obvious correlation between the solubility with the cellular uptake and antimicrobial effect (MIC values). From the MICs values obtained for COE-D4, COE-D6 and COE-D8, it was observed that COE-D6 has an aqueous solubility of 240 μg/mL with a MIC value of 16 μg/mL against the reference strain E. coli K12. On the other hand, the diaminoethyl analogue COE-D62N achieves an aqueous solubility more than 4000 μg/mL, and obtains an even better MIC of 8 μg/mL under the same condition.

While it may be appreciated that a higher cellular uptake may a critical factor for better antimicrobial efficacy. This does not apply to the diaminoalky COE analogues. For example, COE-D62N has a cellular uptake of 11±2% for *E. coli* K12, but its counterpart COE-D82N achieves an uptake ratio of 76±3% under the same condition. However, these two COEs show the same MIC value of 8 µg/mL against the *E. coli* K12.

In addition, it appears that solubility of the COEs may not necessary correlate with the cellular uptake. For example, COE-T4 has an aqueous solubility of 210 µg/mL with a cellular uptake ratio 75±5% based on *E. coli* K12. On the other hand, its diaminoethyl analogue COE-T42 has a better aqueous solubility of more than 1000 µg/mL, but has better uptake of 82±5% under the same condition.

Example 5. Anti-Biofilm Activity of COEs in Comparison to Various Conventional Antibiotics The formation of biofilm by bacteria poses a serious problem for public health because of the increased resistance to antimicrobial agents and general recalcitrance. A key step to eradicate them is to first disperse the biofilm structure and expose the bacteria to antimicrobial agents. With that, two COEs (COE-T42 and COE-T62) of the current invention were tested for their anti-biofilm activity, in comparison to various conventional antibiotics.

Experimental Procedure for Anti-Biofilm Protocol

*Pseudomonas aeruginosa* (PAO1) was grown in Luria-Bertani (LB) broth under shaking (200 rpm) at 37° C. for 16-18 hours. The overnight culture was diluted to 1:200 in M9GC media (M9 medium supplemented with glucose and casamino acids), and 200 µL of diluted culture was added to each well of MBEC plate (Innovotech, Canada). After incubating at 37° C. for 5 hours under shaking (200 rpm), biofilm was formed on the pegs of the MBEC plate. The pegs were then rinsed with 1× phosphate buffered saline (PBS) solution (200 µL per well), and exposed to a two-fold dilution series of COE in M9GC media (200 µL per well). The challenge plate was incubated at 37° C. for 1 hour under shaking (200 rpm), and then the pegs were washed using 200 µL PBS before being dipped into 180 µL 0.1 wt. % crystal violet aqueous solution. After incubating at room temperature for 15 minutes, the pegs were rinsed with PBS twice and transferred to a plate containing 200 µL absolute ethanol in each well for 15 minutes. The biofilm mass was quantified by measuring the absorption of crystal violet/ethanol solution at 550 nm. The minimum biofilm dispersal concentration (MBDC) values were determined as the lowest COE concentration at which biofilm attached on the peg was completely dispersed. The results were repeated in triplicate.

Results and Discussions

It was observed that some COEs exhibited anti-biofilm properties as shown in Table 6. COE-T62 can disperse *P. aeruginosa* biofilms at 8 µg/mL, similar to the "last resort" antibiotic colistin (4 µg/mL) under the same test condition, while COE-T42 can disperse the biofilm at a higher concentration of 16 µg/mL Notably, COE-T62 has a much lower manufacturing costs than colistin, which is produced by certain strains of *Paenibacillus polymyxa*.

As it will be appreciated, these COEs which are effective in dispersing biofilm can be used in tandem with the ones that are effective against planktonic bacterial cells (in Example 3) to further enhance the antimicrobial efficacy of the COEs.

TABLE 6

Anti-biofilm activities of COE-T42 and COE-T62, in comparison to other conventional antibiotics.

| Compound | Minimum biofilm dispersal concentration (µg/mL) |
|---|---|
| COE-T42 | 16 |
| COE-T62 | 8 |
| Colistin | 4 |
| AminoPIP1-Cefta | 512 |
| AminoPIP2-Cefta | 512 |
| Ceftazidime | >512 |
| Gentamicin | >512 |
| Tobramycin | >512 |
| Ciprofloxacin | >512 |

Example 6. Antimicrobial Efficacy (Time-Kill Assay), Bacterial Resistance-Inducing Effect and Skin Model Studies of COE-D62N and COE-D82N To investigate the antimicrobial efficacy and bacterial resistance-inducing of the COEs of the current invention, time-kill assays and resistance evolution experiments of COE-D62N and COE-D82N on methicillin-resistant *Staphylococcus aureus* (MRSA BAA-40) were carried out. In addition, the efficacy of the COEs was also investigated using a skin model inoculated with MRSA BAA-40.

Experimental Procedures

Time-Kill Assays

A stationary-phase culture of MRSA BAA-40 was diluted to $2 \times 10^8$ CFU/mL in fresh MHB. 500 µL of this suspension was then mixed with another 500 µL of MHB containing twice the desired final concentrations of COEs and vancomycin (32 µg/mL). The tube was incubated at 37° C. with 200 rpm shaking. Aliquots were removed at various time points and were serially diluted in PBS, and plated on MHB plates to enumerate CFU/mL.

Resistance Evolution Experiment

To evaluate the propensity of COE to induce resistance, a serial passage of MRSA BAA-40 in MHB medium containing 100-fold diluted stationary-phase culture with increasing concentrations of COE was performed. After incubation for 24 hrs at 37° C., with the initial MIC determined, bacterial suspension from the well showing ½ MIC was used to generate the inoculum for the current day's assay. Serial passaging was continued over 17 days to ensure further resistance did not occur.

Results and Discussions

Figure 11:
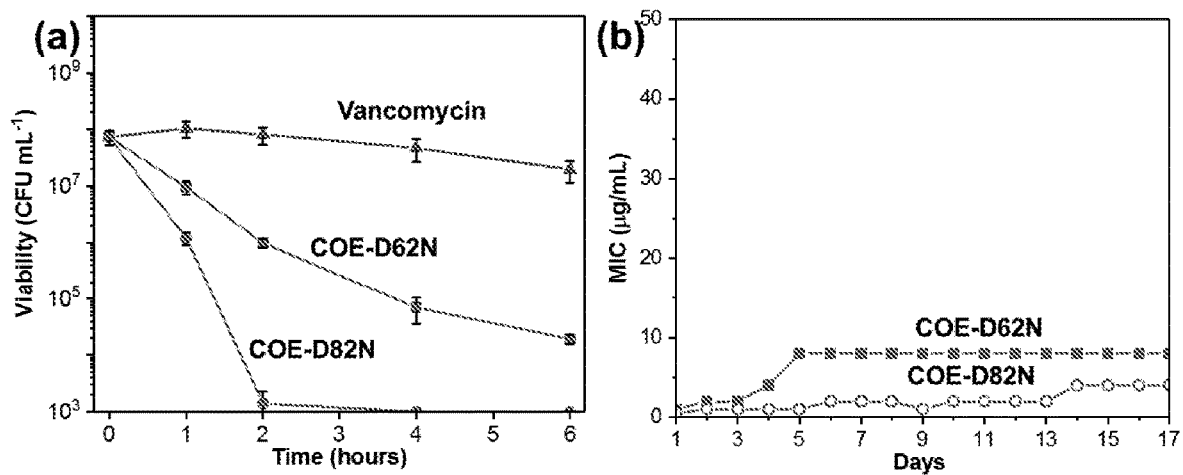
FIG. 11 Depicts: (a) the time-kill assay of COE-D62N, COE-D82N and vancomycin against MRSA BAA-40; and (b) the MIC of COE-D62N and COE-D82N on MRSA BAA-40 from the resistance evolution experiments conducted over 17 days.

From the time-kill assays as shown in FIG. 11a, it was observed that both COE-D62N and COE-D82N reduced the viability of MRSA BAA-40 much faster than that of vancomycin. Specifically, COE-D82N was able to reduce the viability of MRSA close to the minimum by 2 hrs. This demonstrated that the COE-D62N and COE-D82N have a higher antimicrobial efficacy that commercial antibiotics like vancomycin.

In addition, both COE-D62N and COE-D82N show low tendency to cause resistance in the bacteria as shown in serial passage in the presence of the respective COEs for 17 days (FIG. 11b). It was observed that the MIC for each of COE-D62N and COE-D82N remained relatively constant from the 5th day onwards, indicating that resistance of MRSA BAA-40 towards the COEs were not developed.

Figure 12:
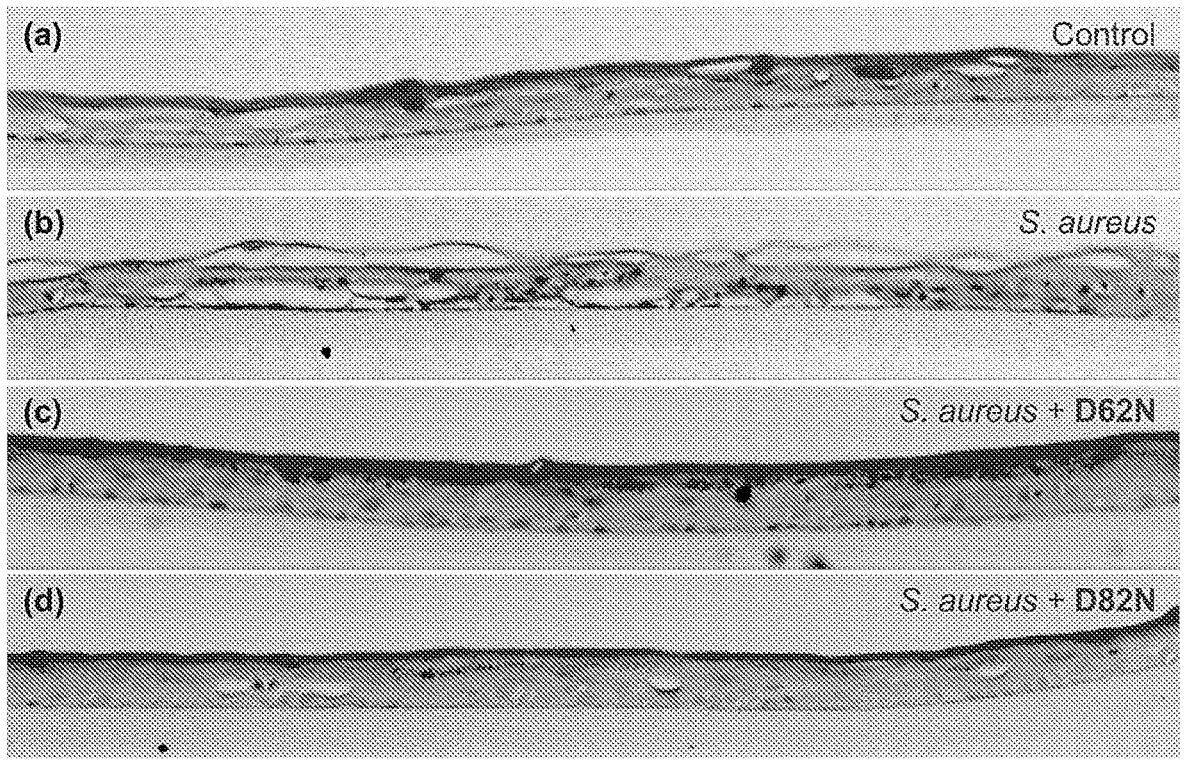
FIG. 12 Depicts the fluorescence micrographs of reconstituted human epidermis skin models (inoculated with *S. aureus*) treated with: (c) COE-D62N; and (d) COE-D82N.

Reconstituted human epidermis (RHE) was cultured in multiwell plates on polymer membrane inserts (0.5 cm² surface area) using immortalized human keratinocytes (250,000 NTERTS) in CnT prime media (from CellnTec) for 48 hours after which they were transferred to CnT 3D prime media for 24 hours before air lifting. The media was changed every 48 hours thereafter and RHE was grown for at least 7 days. After the stratified layers of the RHE were formed, a standardised inoculum of Staphylococcus aureus was added to RHEs (with the exception of the negative control), followed by the addition of 10× the MIC of S. aureus of antimicrobial COEs. It was observed that the models treated with COE-D62N and COE-D82N demonstrated intact skin structure as compared to the one not treated with COEs (FIG. 12). This demonstrated that the COEs are effective in eliminating MRSA BAA-40, as well as the adverse effects of the bacteria on the skin, and that there are no adverse effects from the COEs even when applied at 10× the MIC for S. aureus.

Example 7. Toxicity of COE-D62N, COE-T42 and COE-T62 on Mammalian Cells

For a compound to be safe for use as an antimicrobial agent, it must also demonstrate low toxicity towards mammalian cells. With that, toxicity studies were carried out for selected COEs of the current invention (COE-D62N, COE-T42 and COE-T62) using haemolysis assay.

Haemolysis Assay 1 mL of mammalian blood, collected from a healthy donor (age 29, Male), was mixed with 9 mL of PBS and centrifuged at 1,000 rpm for 5 min. Red blood cell pellet was collected and subsequently washed with PBS three times and diluted to a final concentration of 5% v/v. The various COEs were dissolved in PBS and two folds serial diluted in a 96-well microplate. 50 µL of red blood cell stock was mixed with 50 µL of COE solution in each well and incubated for 1 hr at 37° C. under shaking. The microplate was centrifuged at 1,000 rpm for 10 min. 80 µL aliquots of the supernatant were then transferred to a new 96-well microplate and diluted with another 80 µL of PBS. Haemolytic activity was calculated by measuring absorbance at 540 nm using a 96-well plate spectrophotometer. Triton X-100 (0.1% in PBS), which is able to lyse red blood cells, completely was used as positive control, while PBS was used as negative control. The haemolysis percentage was calculated using the following formula:

$$\text{Haemolysis \%} = \frac{O_p - O_b}{O_t - O_b} \times 100\%$$

where $O_p$ is the absorbance of the COE-treated sample, $O_b$ is the absorbance of negative control and $O_t$ is the absorbance of positive control.

Results and Discussions

The selectivity of COEs towards bacteria or mammalian cells can be quantified using the ratio between the concentrations leading to 50% lysis of human erythrocytes ($HC_{50}$) and the MIC value.

Figure 13:
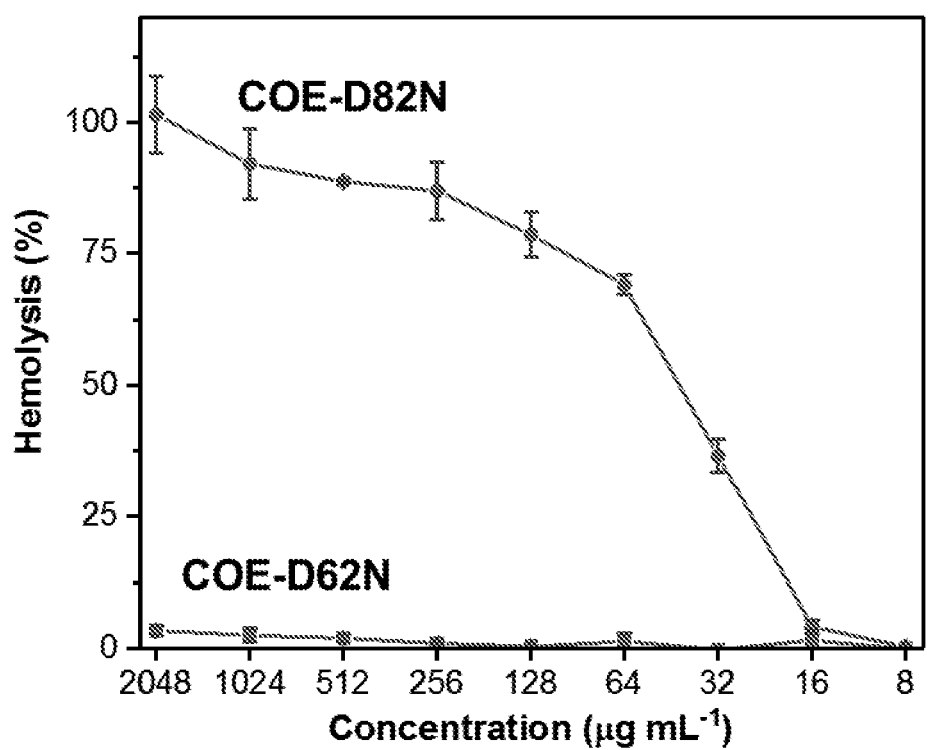
FIG. 13 Depicts a plot of the haemolytic properties of COE-D62N and COE-D82N, as a function of concentrations.

It was observed from preliminary haemolytic studies of COE-D62N, COE-T42 and COE-T62 that these COEs exhibited desirable non-toxicity or low-toxicity on erythrocytes with $HC_{50}$ higher than 16384 µg/mL (Table 7). Therefore, the ratios between $HC_{50}$ and MIC (against E. coli K12) for these COEs were determined to be higher than 1000, suggesting the excellent selectivity of COEs in targeting the membrane of bacteria cells over erythrocytes. A comparison of the haemolytic properties of COE-D62N and COE-D82N, as a function of concentrations is as shown in FIG. 13.

In addition, the COEs exhibited even greater antimicrobial efficacy against S. aureus 25923, which therefore further increased the $HC_{50}$/MIC ratio to over 4000. Notably, COE-D62N was observed to be non-toxic towards erythrocytes and showed an effective antimicrobial activity against the methicillin-resistant S. aureus (MRSA BAA-40) with a MIC value of 1 µg/mL. These findings demonstrated the potential applications of COEs as potent and low-toxicity antimicrobial agents. Further tests were also carried out on COE-D62N and it showed a high aqueous solubility (>200 µM), low toxicity on HepG2 cells ($IC_{50}$>30 µM), good intrinsic hepatic clearance in mice and good intrinsic clearance in human.

TABLE 7

Membrane selectivity ($HC_{50}$, MIC and $HC_{50}$/MIC values) of COEs towards erythrocytes and bacterial cells.

| Compound | COE-D62N | COE-T42 | COE-T62 |
| --- | --- | --- | --- |
| $HC_{50}$ based on erythrocytes (µg/mL) | >32768 | >16384 | >16384 |
| MIC against E. coli K12 (µg/mL) | 8 | 16 | 16 |
| $HC_{50}$/MIC (E. coli) ratio | >4096 | >1024 | >1024 |
| MIC against S. aureus 25923 (µg/mL) | 1 | 4 | 2 |
| $HC_{50}$/MIC (S. aureus) ratio | >32768 | >4096 | >8192 |

The invention claimed is:

1. A compound of formula I:

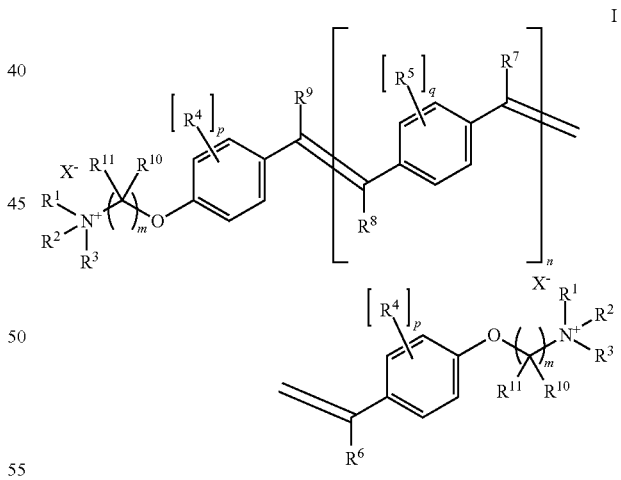

wherein:
n is 0 or 1;
m, at each occurrence, independently represents is 1 to 12;
p and q, at each occurrence, independently represents 0;
$R^1$, at each occurrence, independently represents a —$(CH_2)_o$—$NR^{1'}R^{2'}$ group or a —$(CH_2)_o'$—$N^+R^{1'}R^{2'}R^{3'}$ group, the latter group's charge being balanced by an $X^−$;
each $R^{1'}$, $R^2$, $R^3$, $R^{2'}$ and $R^{3'}$ are independently a $C_{1-12}$ alkyl group;
o and o' are 1 to 12;

$R^4$ to $R^5$, at each occurrence, independently represents:
(a) H;
(b) halo;
(c) CN;
(d) $C_{1-6}$ alkyl, $C_{2-6}$ alkenyl, $C_{2-6}$ alkynyl (which latter three groups are unsubstituted or substituted by one or more substituents selected from F, Cl, Br, nitro, CN, $C_{1-6}$ alkyl, $C_{2-6}$ alkenyl, $C_{2-6}$ alkynyl (which latter three groups are unsubstituted or substituted by one or more substituents selected from OH, =O, F, Cl, Br, $C_{1-4}$ alkyl and $C_{1-4}$ alkoxy), $Cy^1$ (which $Cy^1$ group is unsubstituted or is substituted by one or more substituents selected from F, Cl, Br, nitro, CN, $C_{1-6}$ alkyl, $C_{2-6}$ alkenyl, $C_{2-6}$ alkynyl (which latter three groups are optionally substituted by one or more substituents selected from OH, =O, F, Cl, Br, $C_{1-4}$ alkyl and $C_{1-4}$ alkoxy), $OR^{12a}$, $S(O)_rR^{12b}$, $S(O)^2NR^{12c}R^{12d}$, $NR^{12e}S(O)_2R^{12f}$, $NR^{12g}R^{12h}$, aryl and $Het^1$);
(e) $Cy^2$ (which $Cy^2$ group is unsubstituted or is substituted by one or more substituents selected from F, Cl, Br, nitro, CN, $C_{1-6}$ alkyl, $C_{2-6}$ alkenyl, $C_{2-6}$ alkynyl (which latter three groups are optionally substituted by one or more substituents selected from OH, =O, F, Cl, Br, $C_{1-4}$ alkyl and $C_{1-4}$ alkoxy), $OR^{13a}$ $S(O)_rR^{13b}$, $S(O)_2NR^{13c}R^{13d}$, $NR^{13e}S(O)_2R^{13f}$, $NR^{13g}R^{13h}$, aryl and $Het^2$),
(f) $Het^a$ (which $Het^a$ group is unsubstituted or substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, F, Cl, Br, $C_{1-4}$ alkyl and $C_{1-4}$ alkoxy), $OR^{14a}$, $S(O)_rR^{14b}$, $S(O)_2NR^{14c}R^{14d}$, $NR^{14e}S(O)_2R^{14f}$, $NR^{14g}R^{14h}$, aryl and $Het^3$);
(g) $OR^{15a}$;
(h) $S(O)_rR^{15b}$;
(i) $S(O)_2NR^{15c}R^{15d}$;
(j) $NR^{15e}S(O)_2R^{15f}$, and
(k) $NR^{15g}R^{15h}$;
$R^6$ to $R^{11}$, at each occurrence, independently represents:
(i) H;
$R^{12a}$ to $R^{12h}$, $R^{13a}$ to $R^{13h}$, $R^{14a}$ to $R^{14h}$, $R^{15a}$ to $R^{15h}$, independently represent, at each occurrence, H, $C_{1-6}$ alkyl, $C_{2-6}$ alkenyl, $C_{2-6}$ alkynyl (which latter three groups are optionally substituted by one or more substituents selected from F, Cl, Br, nitro, =O, C(O)O$C_{1-4}$ alkyl, CN, $C_{1-6}$ alkyl, $C_{2-6}$ alkenyl, $C_{2-6}$ alkynyl, $C_{3-6}$ cycloalkyl (which latter three groups are optionally substituted by one or more substituents selected from OH, =O, F, Cl, Br, $C_{1-4}$ alkyl and $C_{1-4}$ alkoxy), $OR^{16a}$, $S(O)_rR^{16b}$, $S(O)_2NR^{16c}R^{16d}$, $NR^{16e}S(O)_2R^{16f}$, $NR^{16g}R^{16h}$, aryl and $Het^4$), $C_{3-10}$ cycloalkyl, or $C_{4-10}$ cycloalkenyl (which latter two groups are optionally substituted by one or more substituents selected from F, Cl, Br, OH, =O, $C_{1-6}$ alkyl and $C_{1-6}$ alkoxy) or $Het^b$;
$R^{16a}$ to $R^{16h}$ independently represent at each occurrence, H, $C_{1-4}$ alkyl, $C_{2-4}$ alkenyl, $C_{2-4}$ alkynyl which latter three groups are optionally substituted by one or more substituents selected from F, Cl, Br, nitro, CN, $C_{1-4}$ alkyl, $C_{2-4}$ alkenyl, $C_{2-4}$ alkynyl (which latter three groups are optionally substituted by one or more substituents selected from OH, =O, F, Cl, Br, $C_{1-4}$ alkyl and $C_{1-4}$ alkoxy), $C_{3-6}$ cycloalkyl, or $C_{4-6}$ cycloalkenyl (which latter two groups are optionally substituted by one or more substituents selected from F, Cl, Br, OH, =O, $C_{1-4}$ alkyl and $C_{1-4}$ alkoxy),
$Het^1$ to $Het^4$, $Het^a$, and $Het^b$ independently represent a 4- to 14-membered heterocyclic groups containing one or more heteroatoms selected from O, S and N, which heterocyclic groups may comprise one, two or three rings and may be substituted by one or more substituents selected from =O, or halo, $C_{1-6}$ alkyl, which latter group is optionally substituted by one or more substituents selected from F, Cl, Br, $-OR^{17a}$, $-NR^{17b}R^{17c}$, $-C(O)OR^{17d}$ and $-C(O)NR^{17e}R^{17f}$,
$R^{17a}$ to $R^{17f}$ independently represent at each occurrence, H, $C_{1-4}$ alkyl, $C_{2-4}$ alkenyl, $C_{2-4}$ alkynyl which latter three groups are optionally substituted by one or more substituents selected from F, Cl, Br, nitro, CN, $C_{1-4}$ alkyl, $C_{2-4}$ alkenyl, $C_{2-4}$ alkynyl (which latter three groups are optionally substituted by one or more substituents selected from OH, =O, F, Cl, Br, $C_{1-4}$ alkyl and $C_{1-4}$ alkoxy), $C_{3-6}$ cycloalkyl, or $C_{4-6}$ cycloalkenyl (which latter two groups are optionally substituted by one or more substituents selected from F, Cl, Br, OH, =O, $C_{1-4}$ alkyl and $C_{1-4}$ alkoxy),
$Cy^1$, $Cy^2$, $Cy^{1'}$ and $Cy^{2'}$, at each occurrence, independently represents a 3- to 10-membered aromatic, fully saturated or partially unsaturated carbocyclic ring;
each r independently represents 0, 1 or 2; and
each $X^-$ is a pharmaceutically acceptable anion, or pharmaceutically acceptable salts and solvates thereof.

2. The compound according to claim 1, wherein:
m is 4 to 8.
3. The compound according to claim 1, wherein o, when present, is 2 to 4.
4. The compound according to claim 1, wherein o', when present, is 2 to 4.
5. The compound according to claim 1, wherein each of $R^2$ to $R^3$ is methyl.
6. The compound according to claim 1, wherein $R^1$ is a $-(CH_2)_{o'}-N+R^{1'}R^{2'}R^{3'}$ group.
7. The compound according to claim 1, wherein $R^{1'}$, $R^{2'}$ and $R^{3'}$ is a $C_1$ to $C_4$ alkyl.
8. The compound according to claim 1, wherein:
m is 4, 6 or 8;
each $R^{1'}$, $R^2$, $R^3$, $R^{2'}$ and $R^{3'}$ are independently a $C_{1-4}$ alkyl group; and o and o' are 2 to 3.
9. The compound according to claim 1, wherein the compound of formula I is selected from the group consisting of:

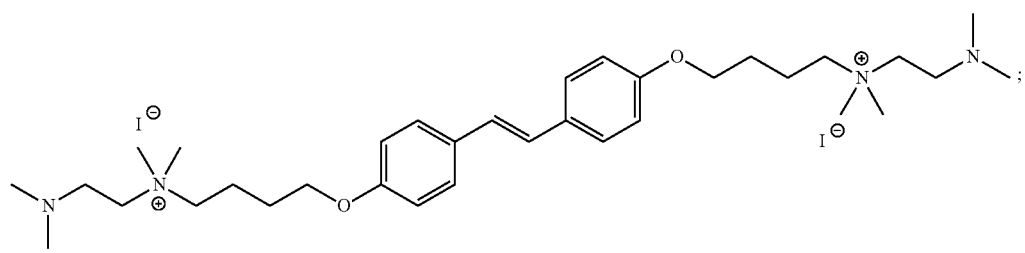

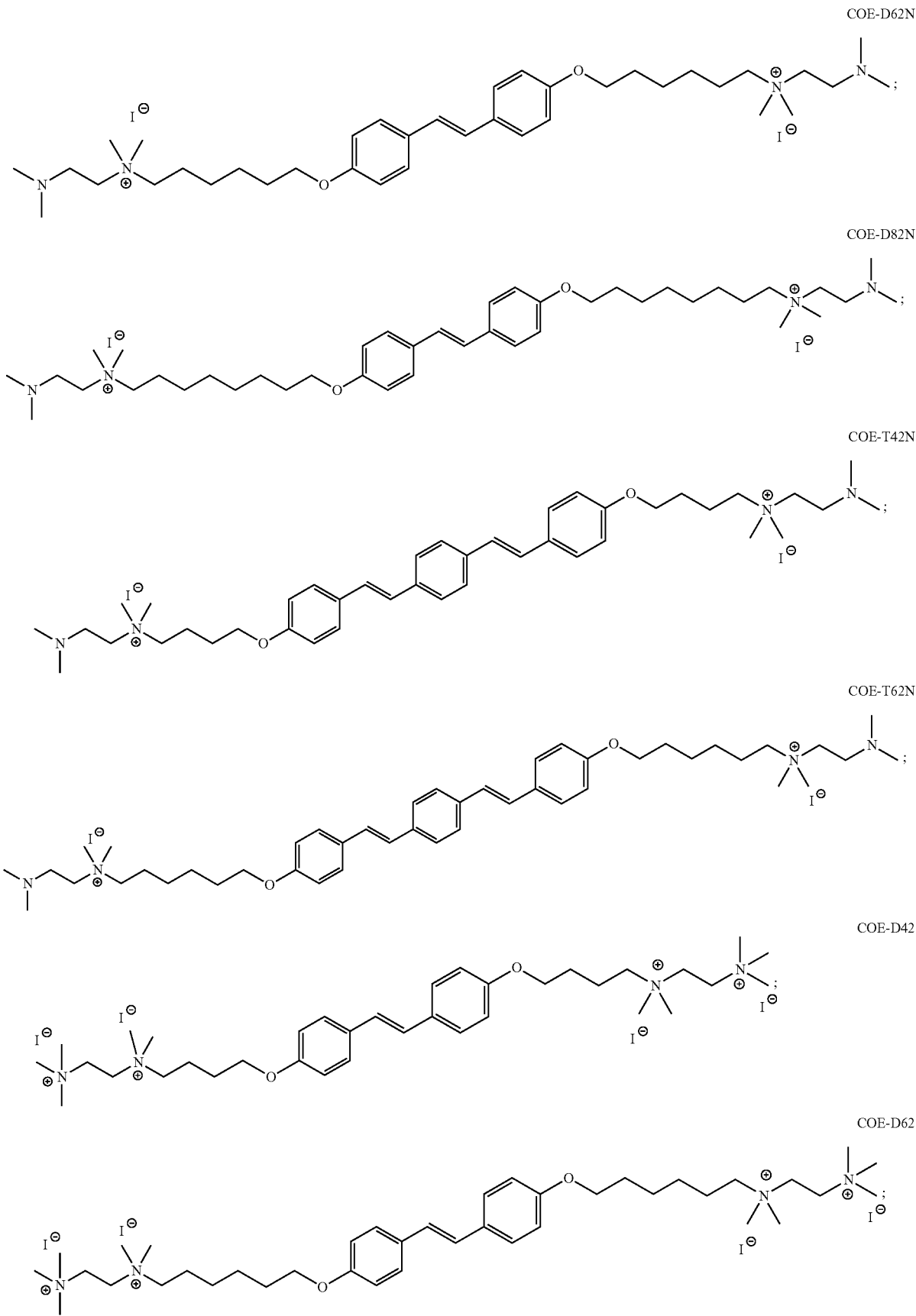

-continued
COE-D82
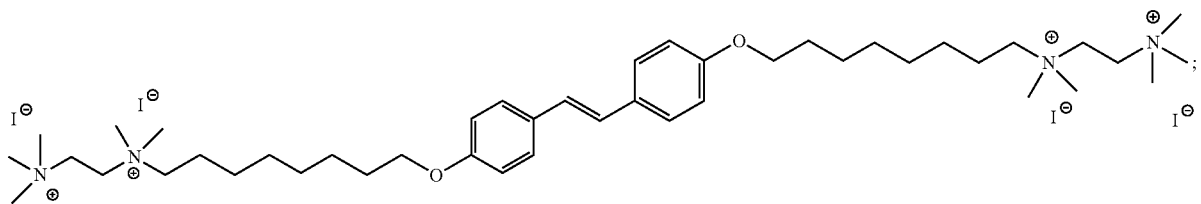
COE-T42
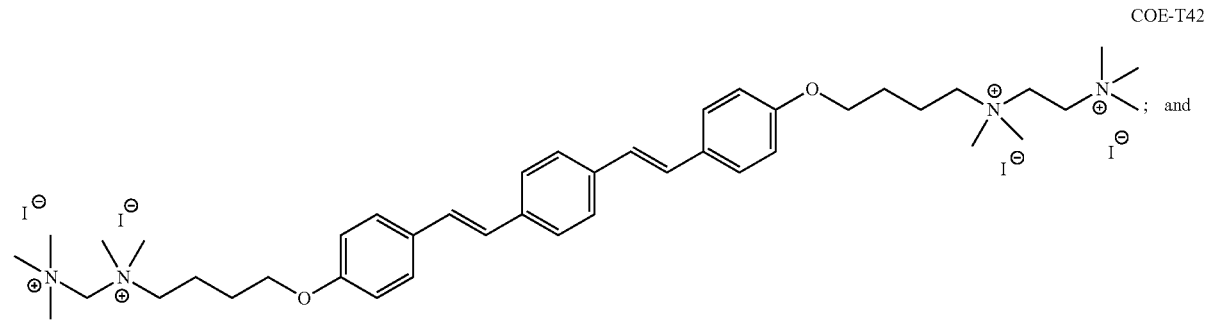
and
COE-T62
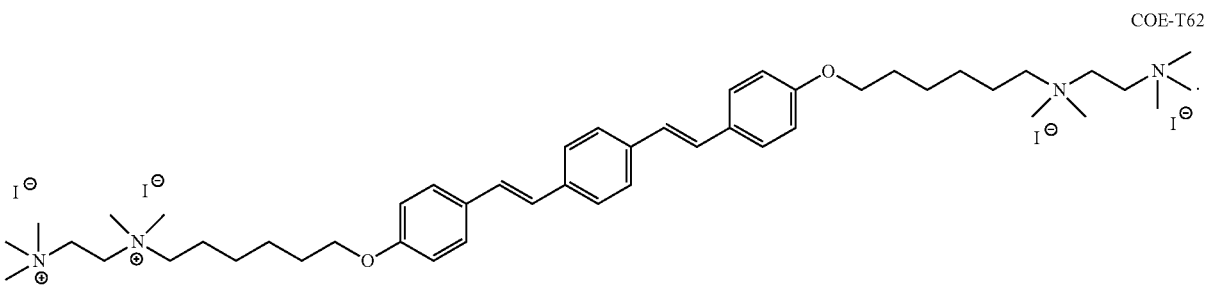
10. The compound according to claim 9, wherein the compound of formula I is selected from the group consisting of:
COE-D42
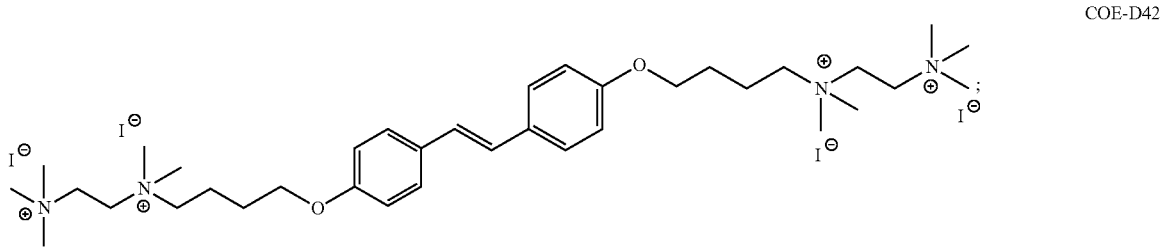
COE-D62
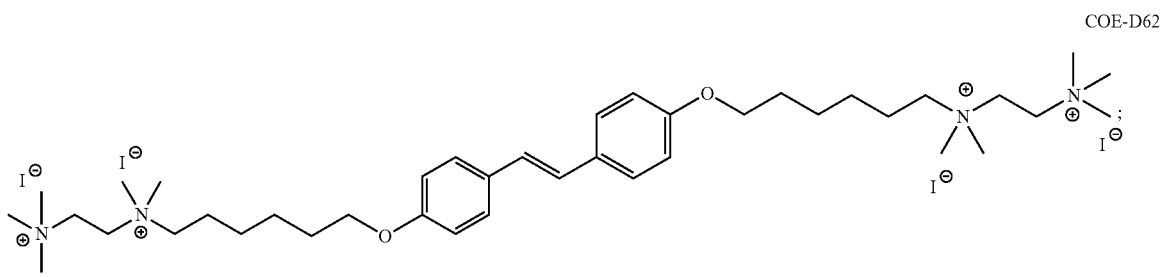

-continued

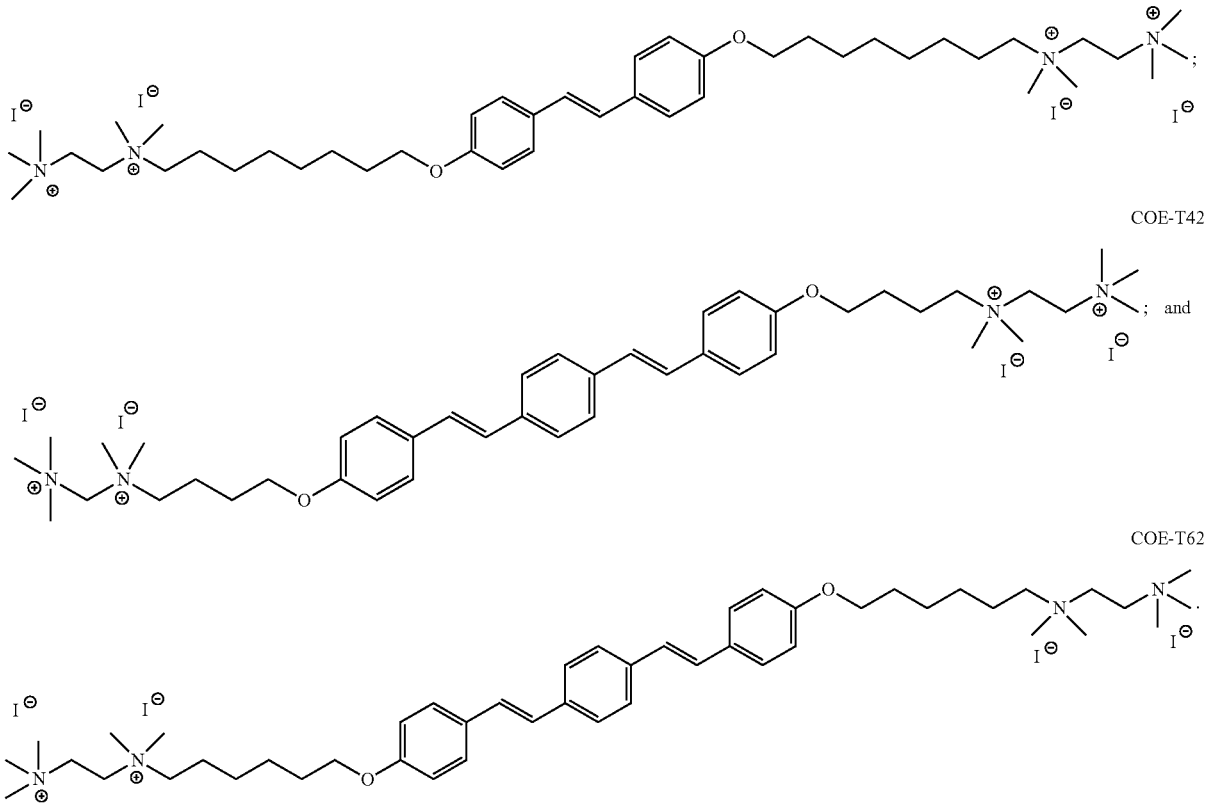

COE-D82

COE-T42

COE-T62

11. The compound according to claim 1, wherein each X— is a halide selected from the group consisting of Br—, Cl—, F— and I—.

12. A pharmaceutical formulation comprising a compound of formula I as defined in claim 1 and one or more of a pharmaceutically acceptable adjuvant, diluent or carrier.

13. A method of treating an infection, the method including the step of administering a therapeutically effective amount of a compound of formula I or a salt or solvate thereof as defined in claim 1 to a subject in need thereof.

14. The method according to claim 13, wherein the compound of formula I is selected from the group consisting of:

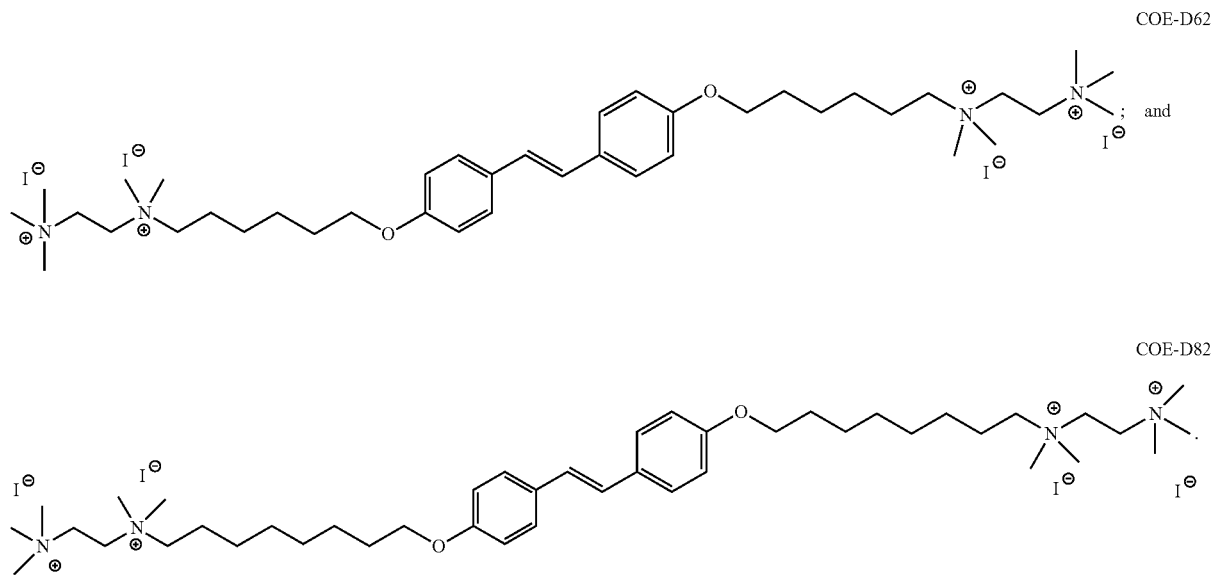

COE-D62

COE-D82

15. A method of removing a biofilm from a solid substrate or preventing build-up of a biofilm on a solid substrate, or killing, inhibiting, or dispersing microbes inhabiting said biofilm in a system susceptible to biofilm formation, said biofilm being formed by at least one microorganism, the method comprising the step of contacting the system with an effective amount of a compound of formula I or a salt or solvate thereof as defined in claim 1 or a composition comprising a compound of formula I to remove the biofilm or prevent its formation.

16. A cosmetic or cleansing formulation, comprising a compound of formula I as defined in claim 1 and one or more of an adjuvant, diluent or carrier suitable for use in a cosmetic or cleansing formulation.

* * * * *